(12) United States Patent
Kluge

(10) Patent No.: US 10,434,105 B2
(45) Date of Patent: *Oct. 8, 2019

(54) THERAPEUTICALLY ACTIVE COMPOUNDS AND THEIR METHODS OF USE

(71) Applicant: Agios Pharmaceuticals, Inc., Cambridge, MA (US)

(72) Inventor: Stefan Kluge, Riehen (CH)

(73) Assignee: Agios Pharmaceuticals, Inc., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/230,090

(22) Filed: Dec. 21, 2018

(65) Prior Publication Data

US 2019/0117662 A1 Apr. 25, 2019

Related U.S. Application Data

(63) Continuation of application No. 15/548,737, filed as application No. PCT/US2016/016335 on Feb. 3, 2016, now Pat. No. 10,201,543.

(60) Provisional application No. 62/112,127, filed on Feb. 4, 2015.

(51) Int. Cl.
| | | |
|---|---|---|
| *A61K 31/53* | (2006.01) | |
| *C07D 401/14* | (2006.01) | |
| *G01N 23/20* | (2018.01) | |
| *G01N 25/48* | (2006.01) | |

(52) U.S. Cl.
CPC ............ *A61K 31/53* (2013.01); *C07D 401/14* (2013.01); *C07B 2200/13* (2013.01); *G01N 23/20075* (2013.01); *G01N 25/4866* (2013.01)

(58) Field of Classification Search
CPC .............................. A61K 31/53; C07D 401/14
USPC ......................................................... 514/246
See application file for complete search history.

(56) References Cited

U.S. PATENT DOCUMENTS

| | | | |
|---|---|---|---|
| 9,512,107 B2 | 12/2016 | Cianchetta et al. | |
| 9,656,999 B2 | 5/2017 | Cianchetta et al. | |
| 9,694,013 B2 | 7/2017 | Agresta | |
| 9,724,350 B2 | 8/2017 | Travins et al. | |
| 9,732,062 B2 | 8/2017 | Cianchetta et al. | |
| 9,738,625 B2 | 8/2017 | Agresta et al. | |
| 9,751,863 B2 | 9/2017 | Zhang | |
| 9,889,137 B2 | 2/2018 | Agresta | |
| 10,201,543 B2* | 2/2019 | Kluge | A61K 31/53 |
| 2013/0190287 A1 | 7/2013 | Cianchetta et al. | |
| 2017/0157132 A1 | 6/2017 | Wu et al. | |
| 2017/0246174 A1 | 8/2017 | Amatangelo et al. | |
| 2017/0298045 A1 | 10/2017 | Cianchetta et al. | |
| 2017/0305885 A1 | 10/2017 | Agresta et al. | |
| 2017/0348318 A1 | 12/2017 | Travins et al. | |
| 2018/0042930 A1 | 2/2018 | Amatangelo et al. | |
| 2018/0064715 A1 | 3/2018 | Bhat et al. | |

FOREIGN PATENT DOCUMENTS

| | | |
|---|---|---|
| WO | WO 2013/102431 A1 | 7/2013 |
| WO | WO 2015/018060 A1 | 2/2015 |
| WO | WO 2016/126798 A1 | 2/2016 |
| WO | WO 2016/053850 A1 | 4/2016 |
| WO | WO 2017/066599 A1 | 4/2017 |

OTHER PUBLICATIONS

Cheson et al., "Clinical application and proposal for modification of the International Working Group (IWG) response criteria in myelodysplasia," *Blood*, 108(2):419-425 (2006).
Cheson et al., "Revised recommendations of the International Working Group for Diagnosis, Standardization of Response Criteria, Treatment Outcomes, and Reporting Standards for Therapeutic Trials in Acute Myeloid Leukemia," *J. Clin. Oncol.*, 21(24):4642-4649 (2003).
Dang et al., "Cancer-associated IDH1 mutations produce 2-hydroxyglutarate," *Nature* 462:739-744 (2009).
Genbank Accession No. NM_002168.2 (Feb. 22, 2014).
Genbank Accession No. NP_002159.2 (Apr. 30, 2016).
Gerhard et al., "The status, quality, and expansion of the NIH full-length cDNA project: the Mammalian Gene Collection (MGC)," *Genome Res.*,14(10B):2121-2127 (2004).
Greenberg et. al. "Revised international prognostic scoring system for myelodysplastic syndromes," *Blood*, 120(12):2454-2465 (2012).
Lee et al., "ICSH guidelines for the standardization of bone marrow specimens and reports," *Int. J. Lab. Hematol.*, 30(5):349-364 (2008).
Rizzo et al., "American Society of Hematology/American Society of Clinical Oncology clinical practice guideline update on the use of epoetin and darbepoetin in adult patients with cancer," *Blood*, 116(20):4045-4059 (2010).
Greenberg et al., "International scoring system for evaluating prognosis in myelodysplastic syndromes," *Blood*, 89(6):2079-2088 (1997).
Greenberg et al., Erratum, *Blood*, 91(3):1100 (1998).
Schanz et al., "Coalesced multicentric analysis of 2,351 patients with myelodysplastic syndromes indicates an underestimation of poor-risk cytogenetics of myelodysplastic syndromes in the international prognostic scoring system," *J. Clin. Oncol.*, 29(15):1963-1970 (2011).
U.S. Appl. No. 14/909,451, Non-final Office Action dated Aug. 8, 2016 (10 pages).
U.S. Appl. No. 14/909,451, Final Office Action dated Feb. 8, 2017 (12 pages).
U.S. Appl. No. 14/909,451, Notice of Allowance dated Apr. 14, 2017 (5 pages).
U.S. Appl. No. 15/649,551, Non-final Office Action dated Aug. 8, 2017 (11 pages).

(Continued)

*Primary Examiner* — Kahsay Habte
(74) *Attorney, Agent, or Firm* — Jones Day

(57) ABSTRACT

Provided are compounds useful for treating cancer and methods of treating cancer, comprising administering to a subject in need thereof a compound described herein.

12 Claims, 46 Drawing Sheets

(56) References Cited

OTHER PUBLICATIONS

U.S. Appl. No. 15/649,551, Final Office Action dated Nov. 24, 2017 (13 pages).
U.S. Appl. No. 15/649,551, Non-final Office Action dated Feb. 12, 2018 (20 pages).
Anonymous, "New Agios clinical data from ongoing phase 1 trial of AG-221 continue to show complete and durable remissions in patients with difficult to treat hematologic maligancies," (Jun. 14, 2014) retrieved from the internet: URL:http://investor.agios.com/phoenix.zhtml?c=251862&p=irol-newsArticle_Print&ID=1939863, retrieved on Dec. 21, 2015, pp. 1-4.
Caira, "Crystalline polymorphism of organic compounds," *Topics Current Chem.*, 198(1):163-208 (1998).
Thomson Reuters Inegrity—PROUS Science, Database Accession No. 876972, Jul. 18, 2015, 1 page.

* cited by examiner

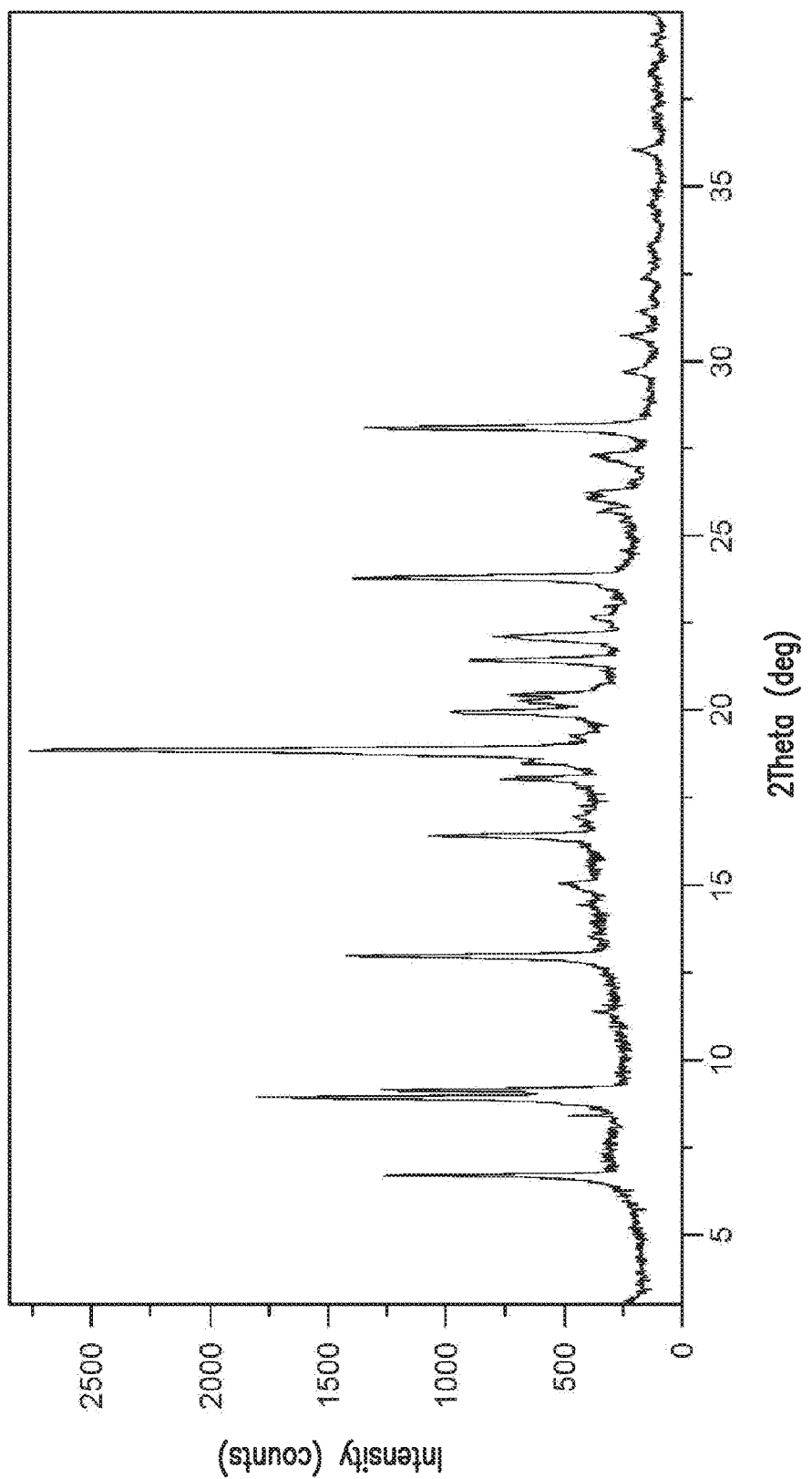
FIG. 1. XRPD pattern of Form 1

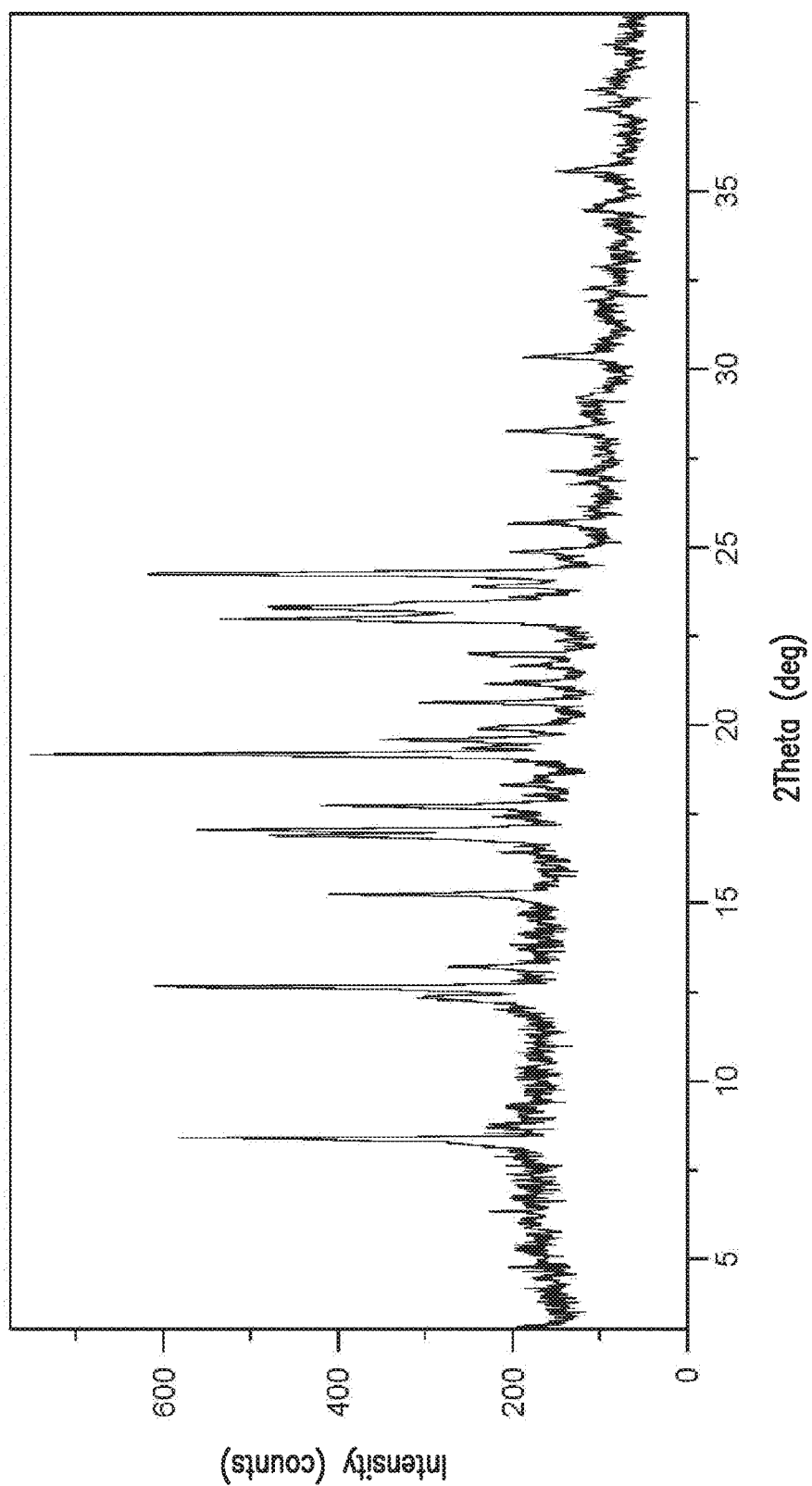
FIG. 2. XRPD pattern of Form 2

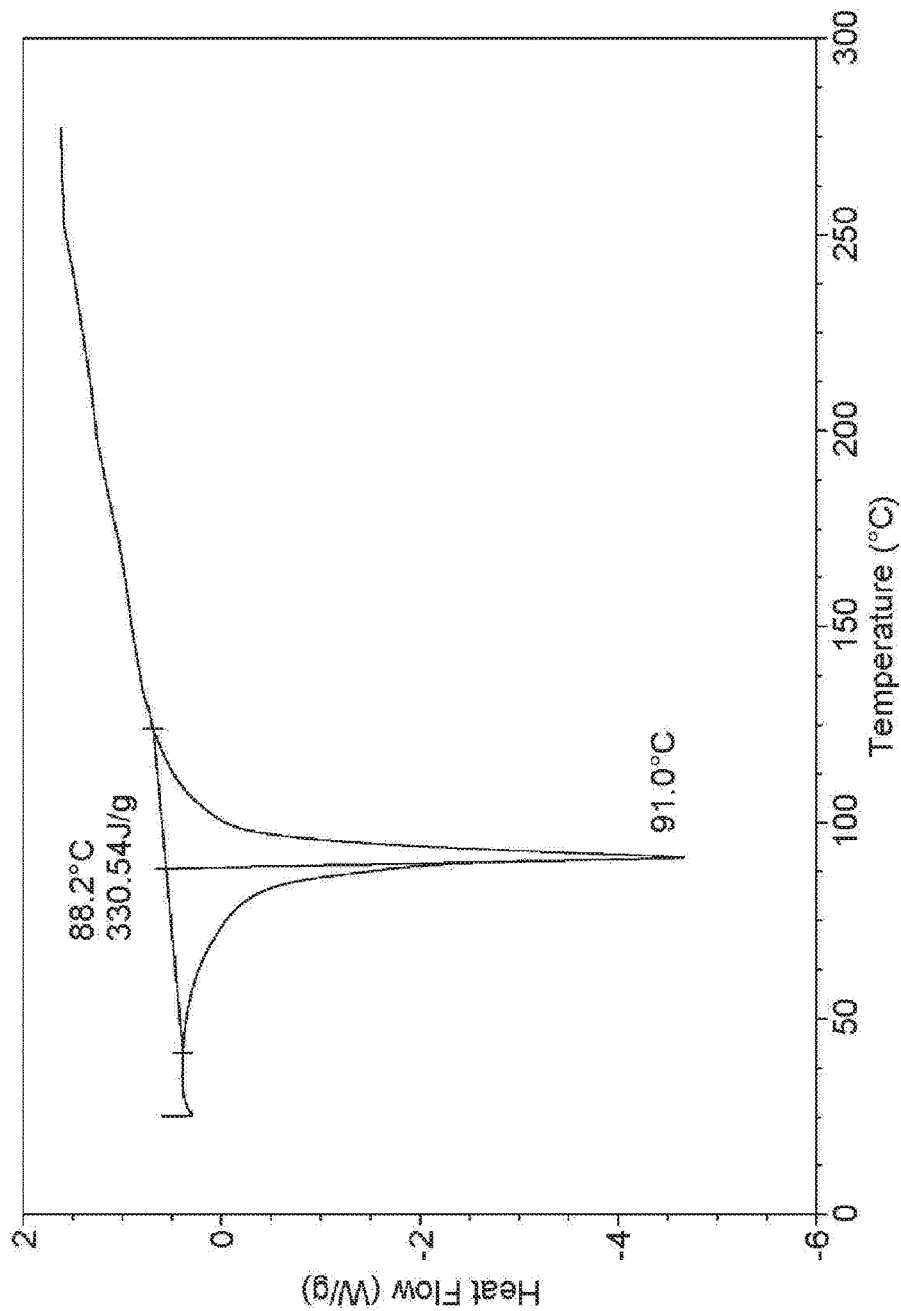
FIG. 3. DSC profile of Form 2

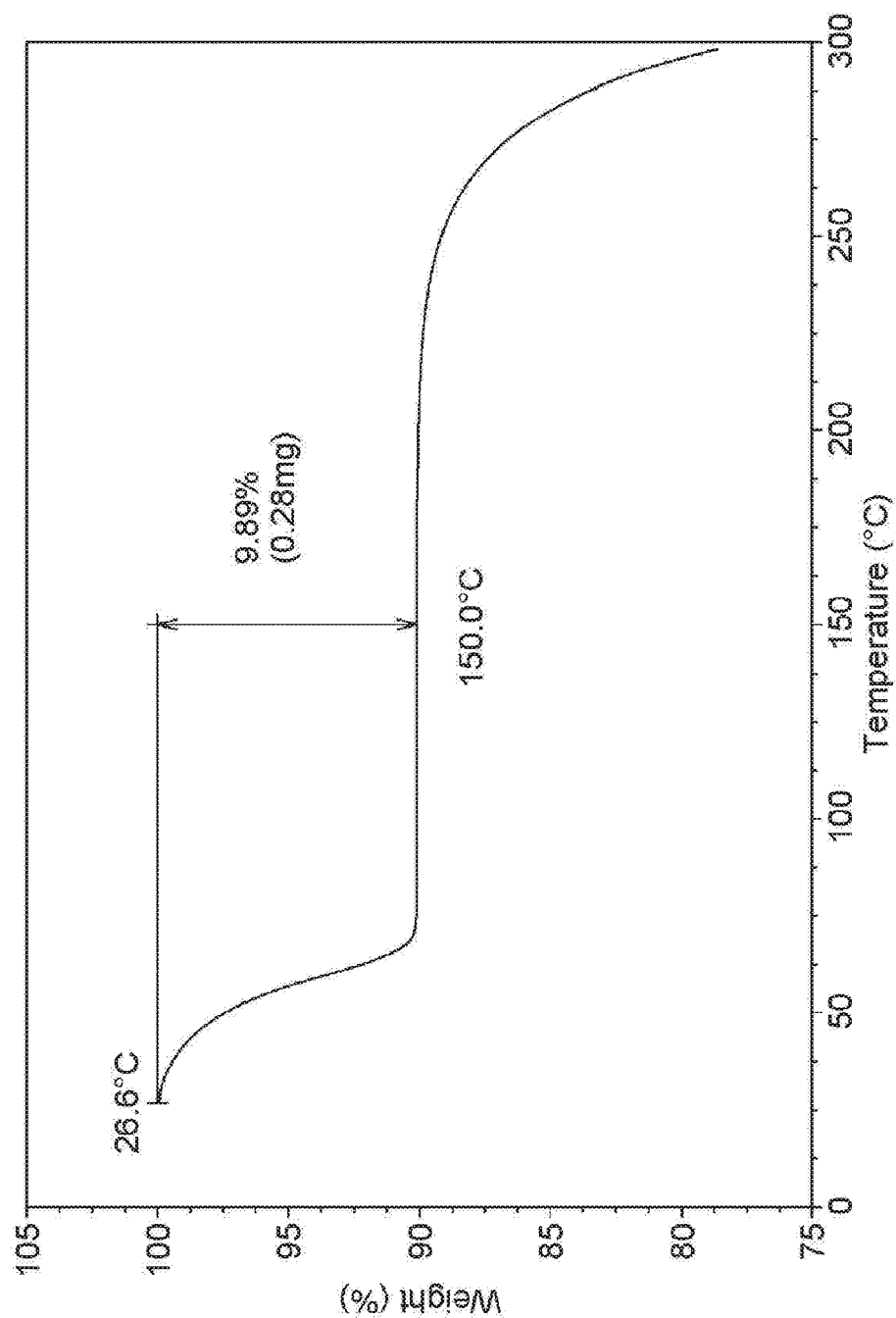
FIG. 4. TGA profile of Form 2

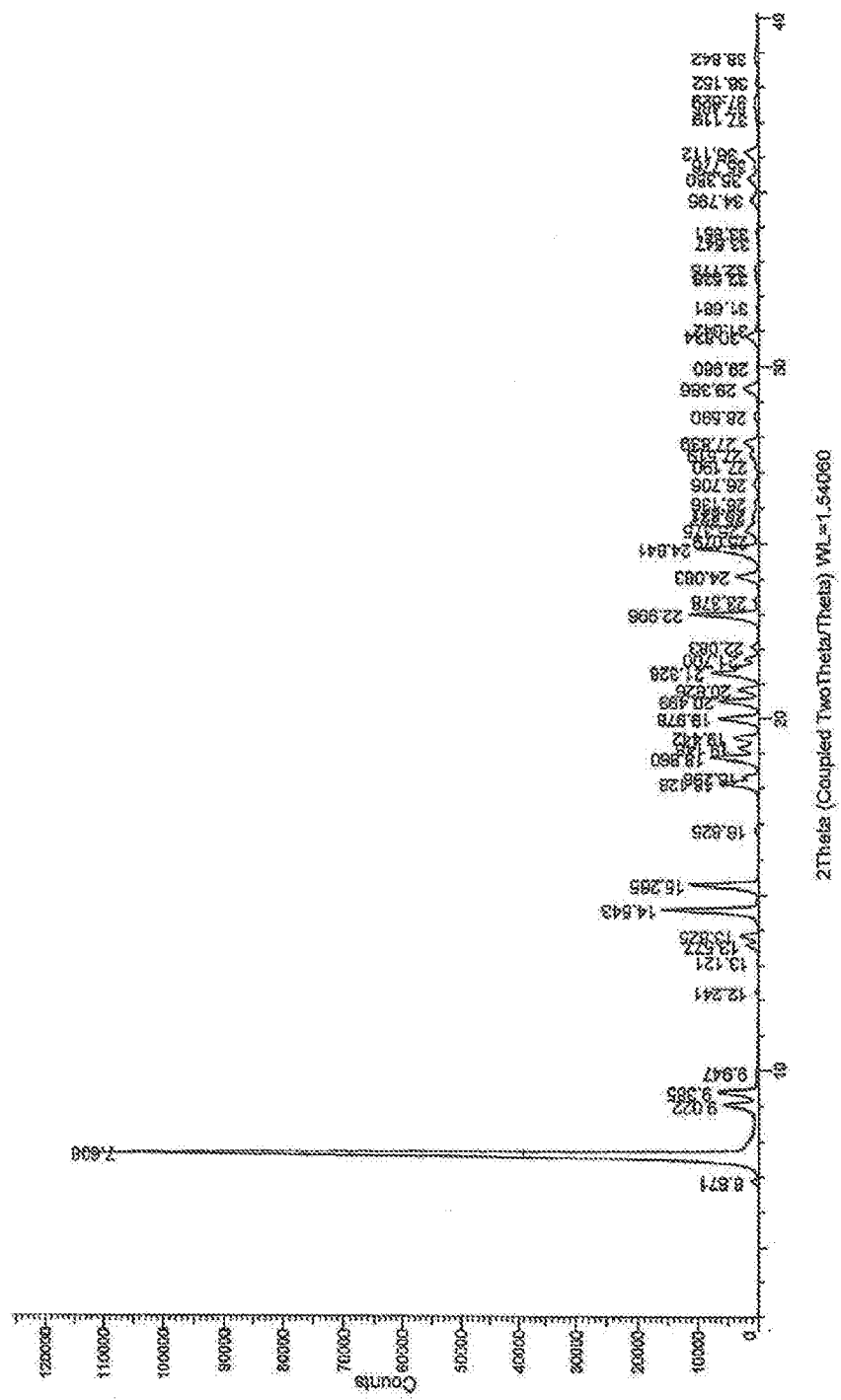
FIG. 5. XRPD pattern of Form 3

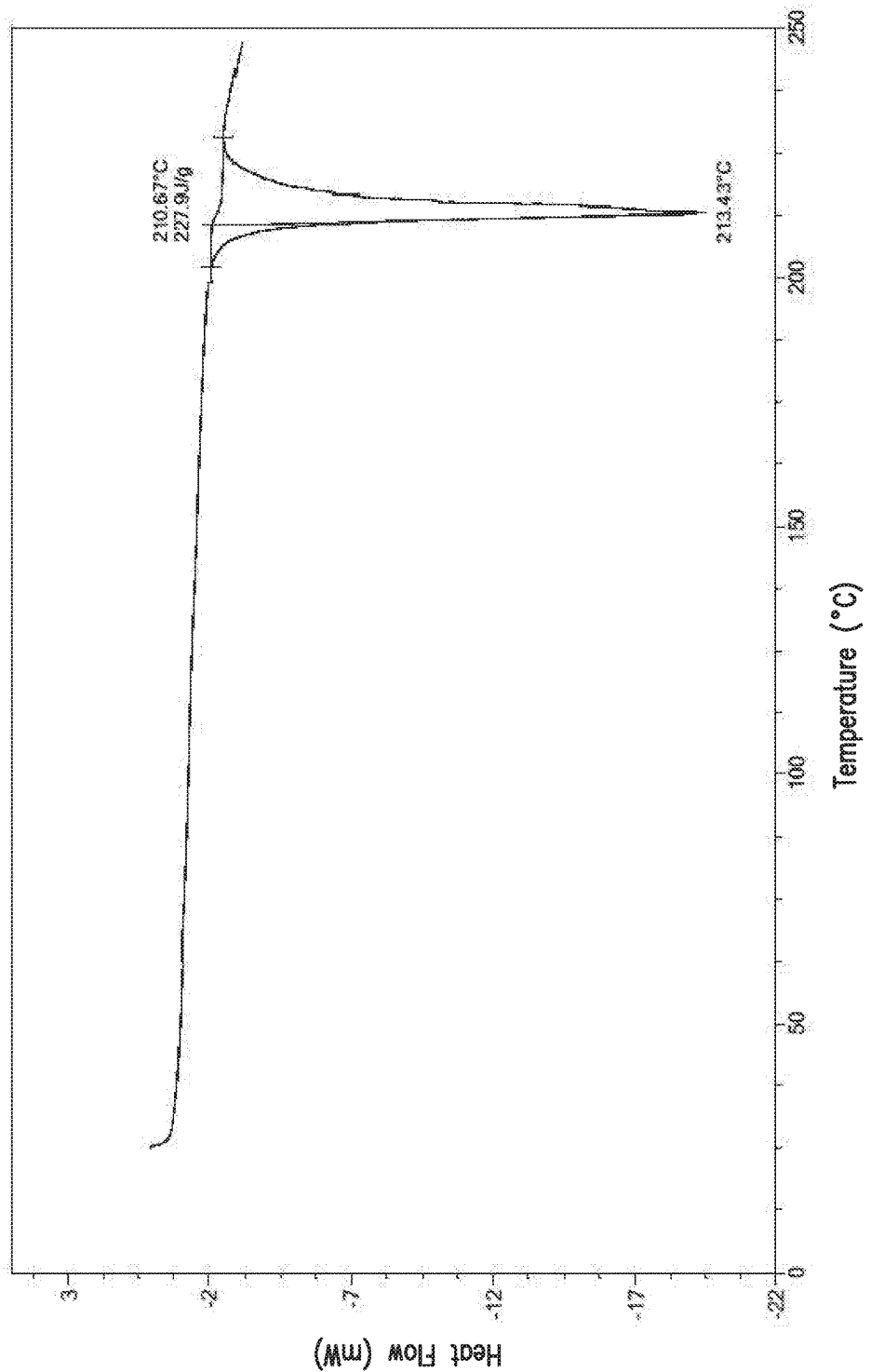
FIG. 6. DSC profile of Form 3

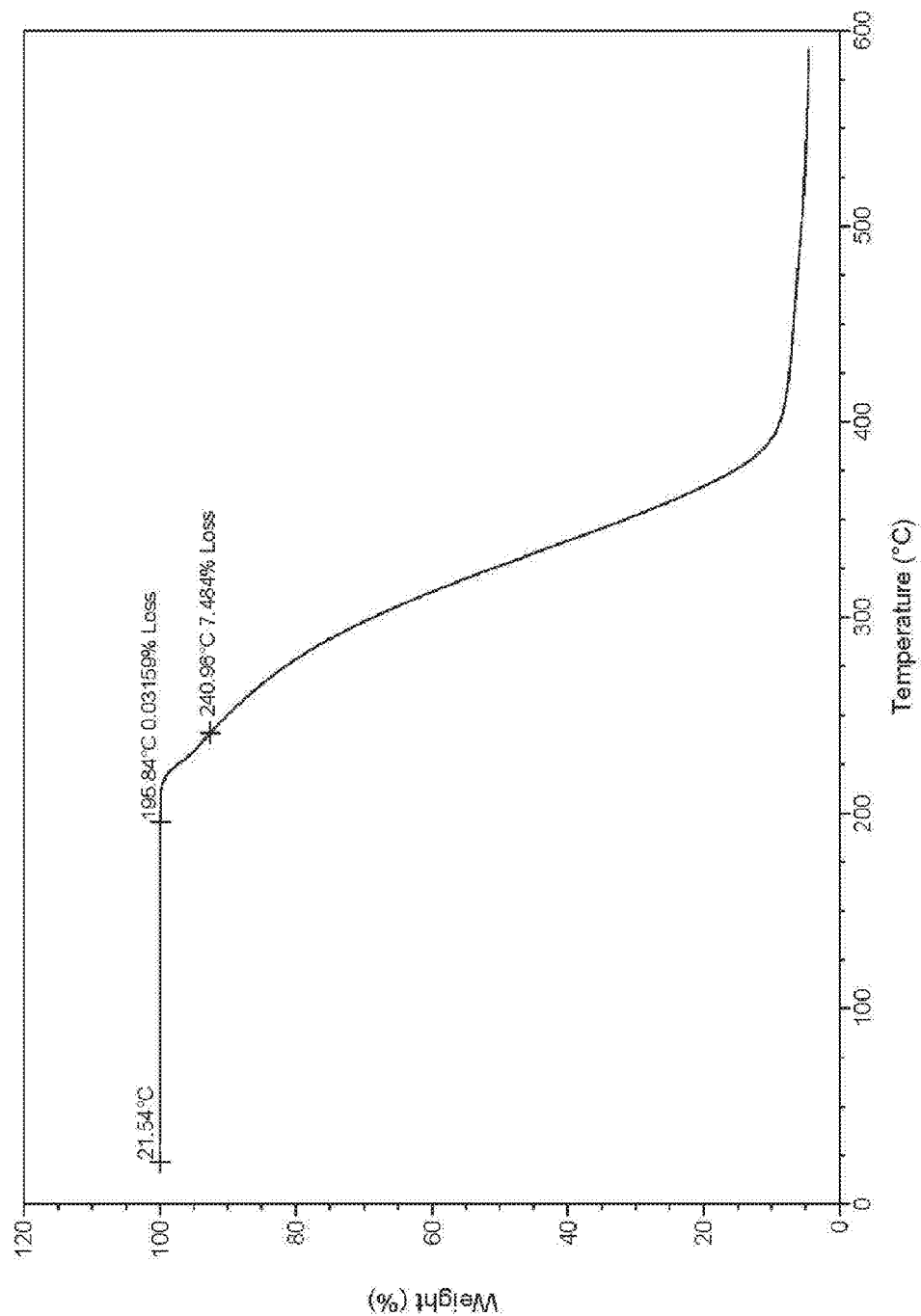
FIG. 7. TGA profile of Form 3

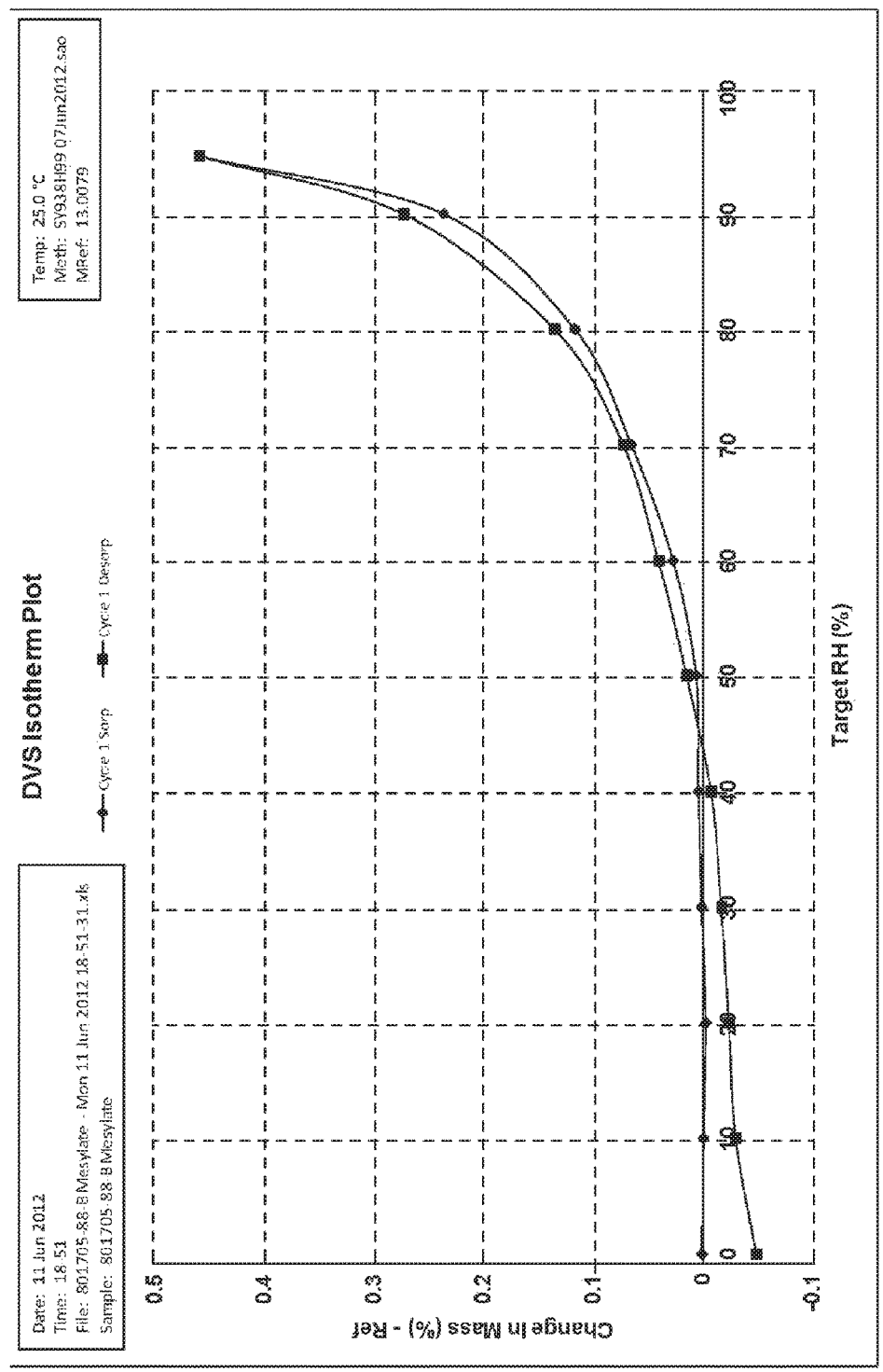
FIG. 8. DVS profile of Form 3

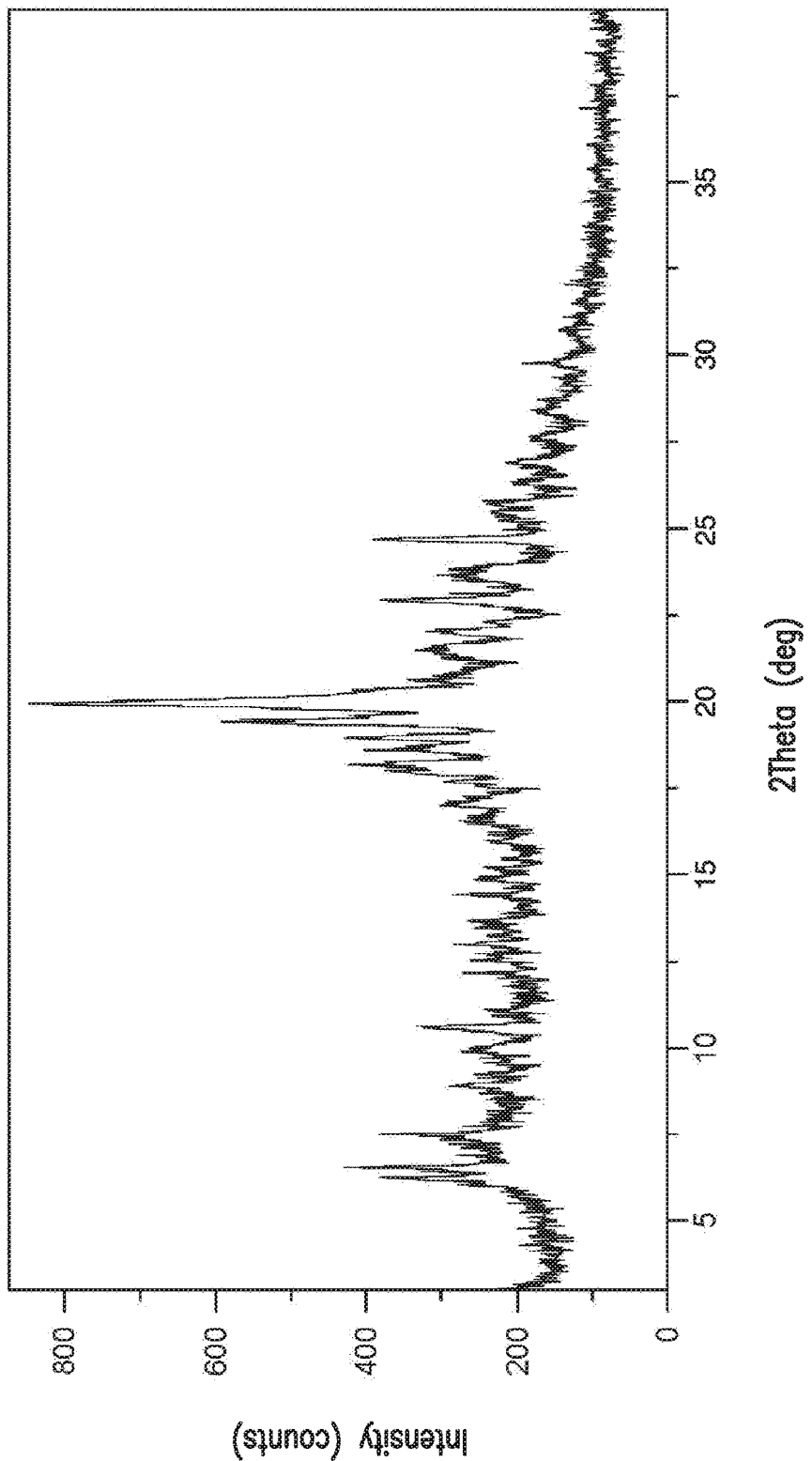
FIG. 9. XRPD pattern of Form 4

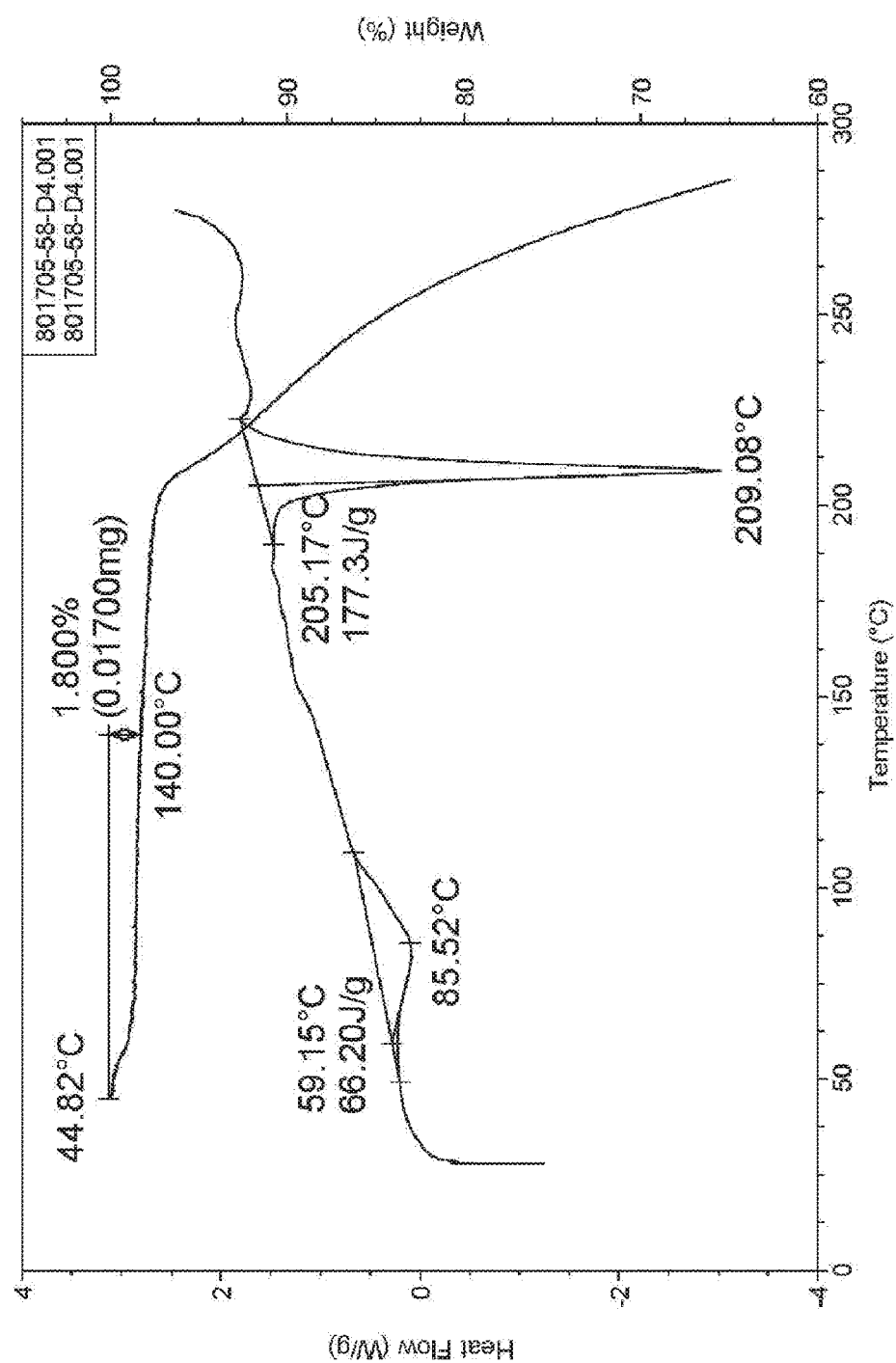
FIG. 10. DSC and TGA profile of Form 4

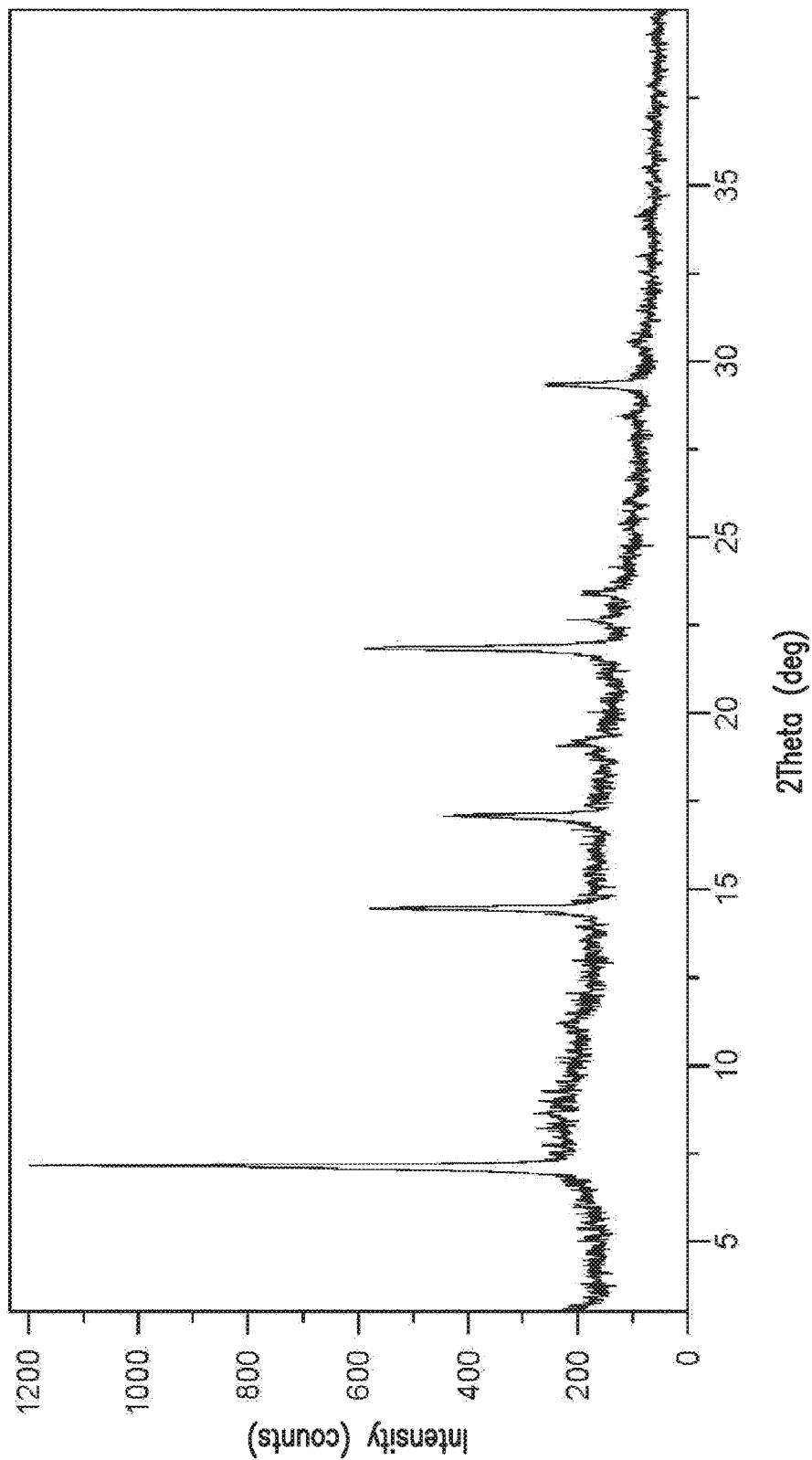
FIG. 11. XRPD pattern of Form 5

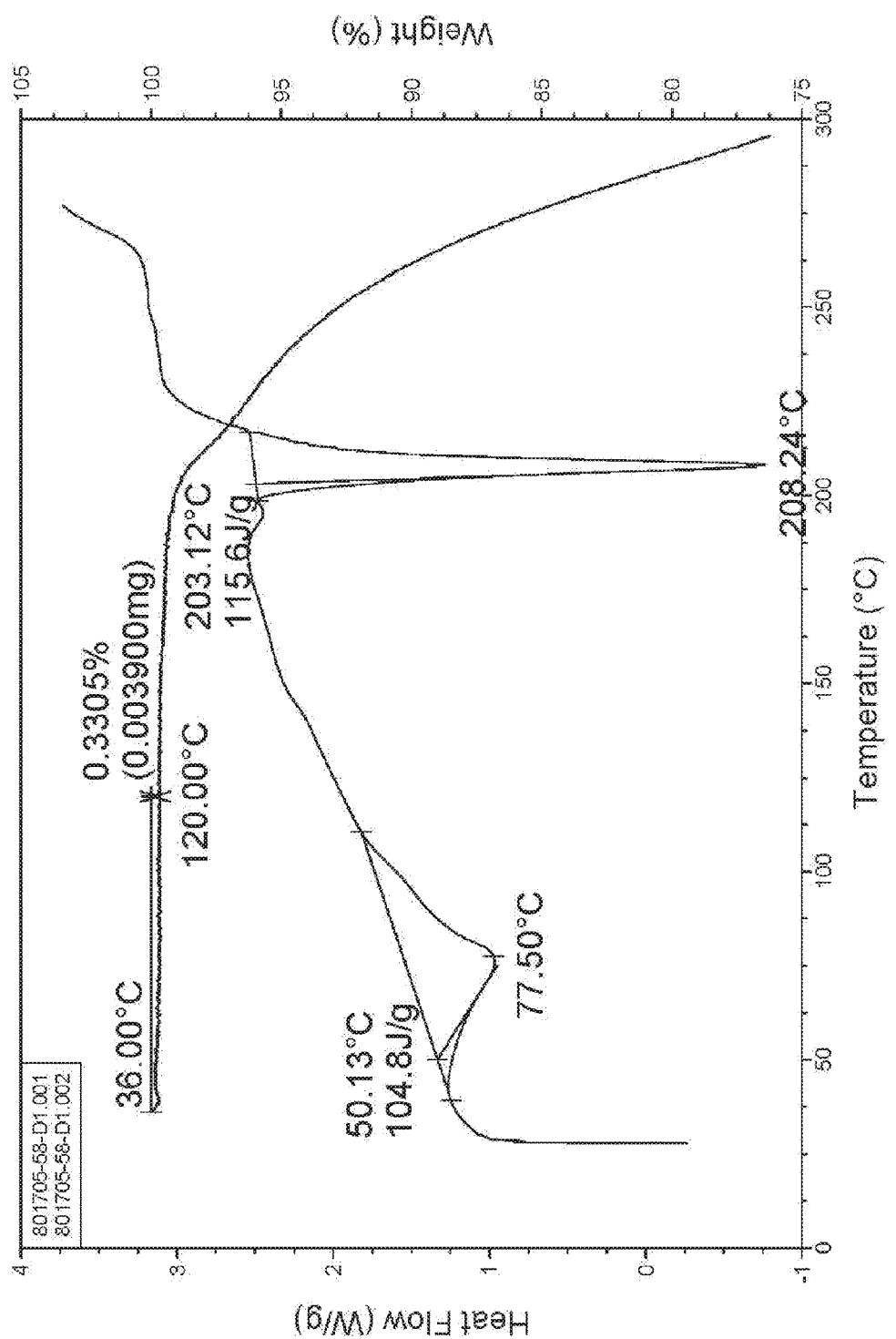
FIG. 12. DSC and TGA profile of Form 5

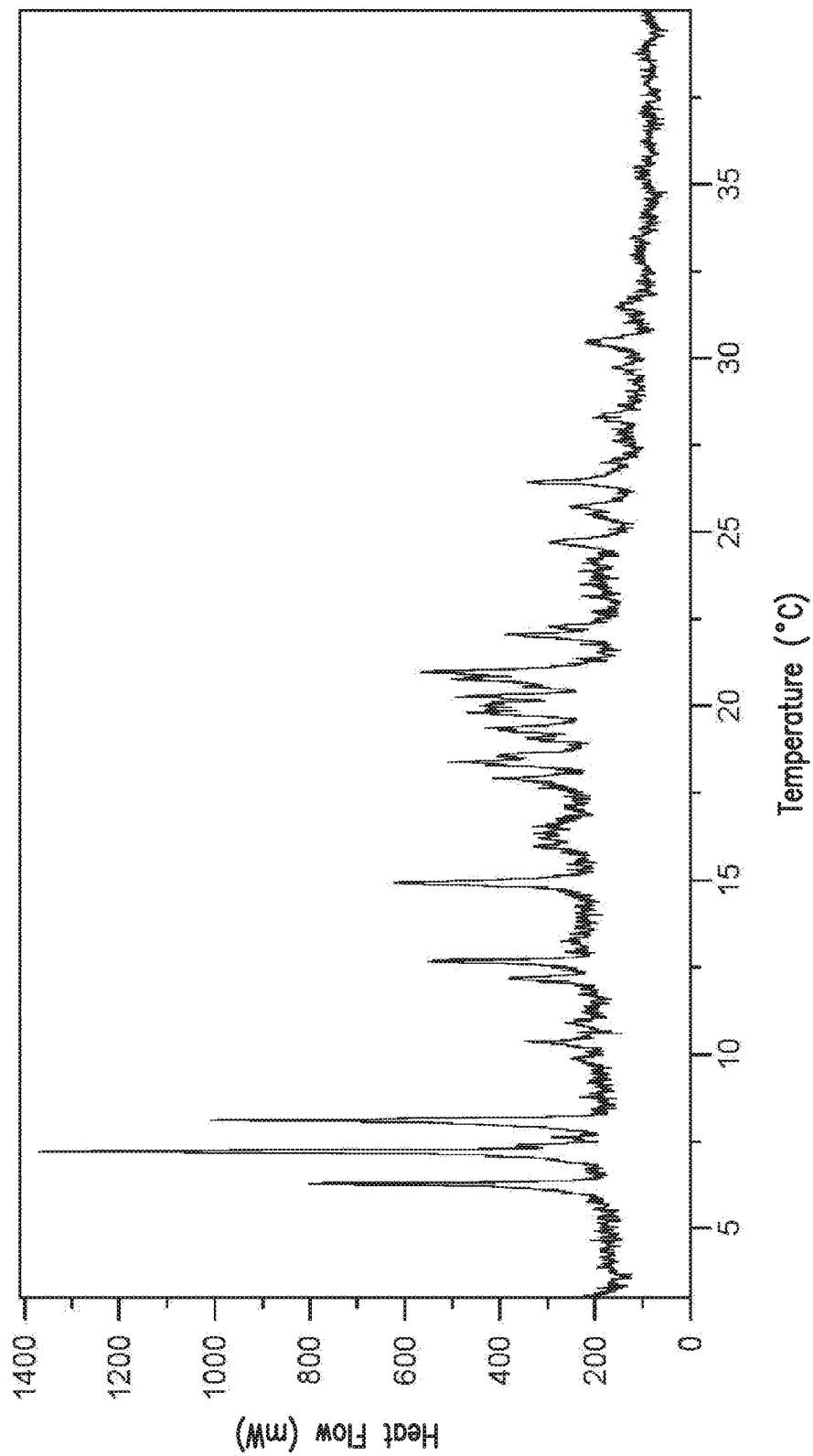
FIG. 13. XRPD pattern of Form 6

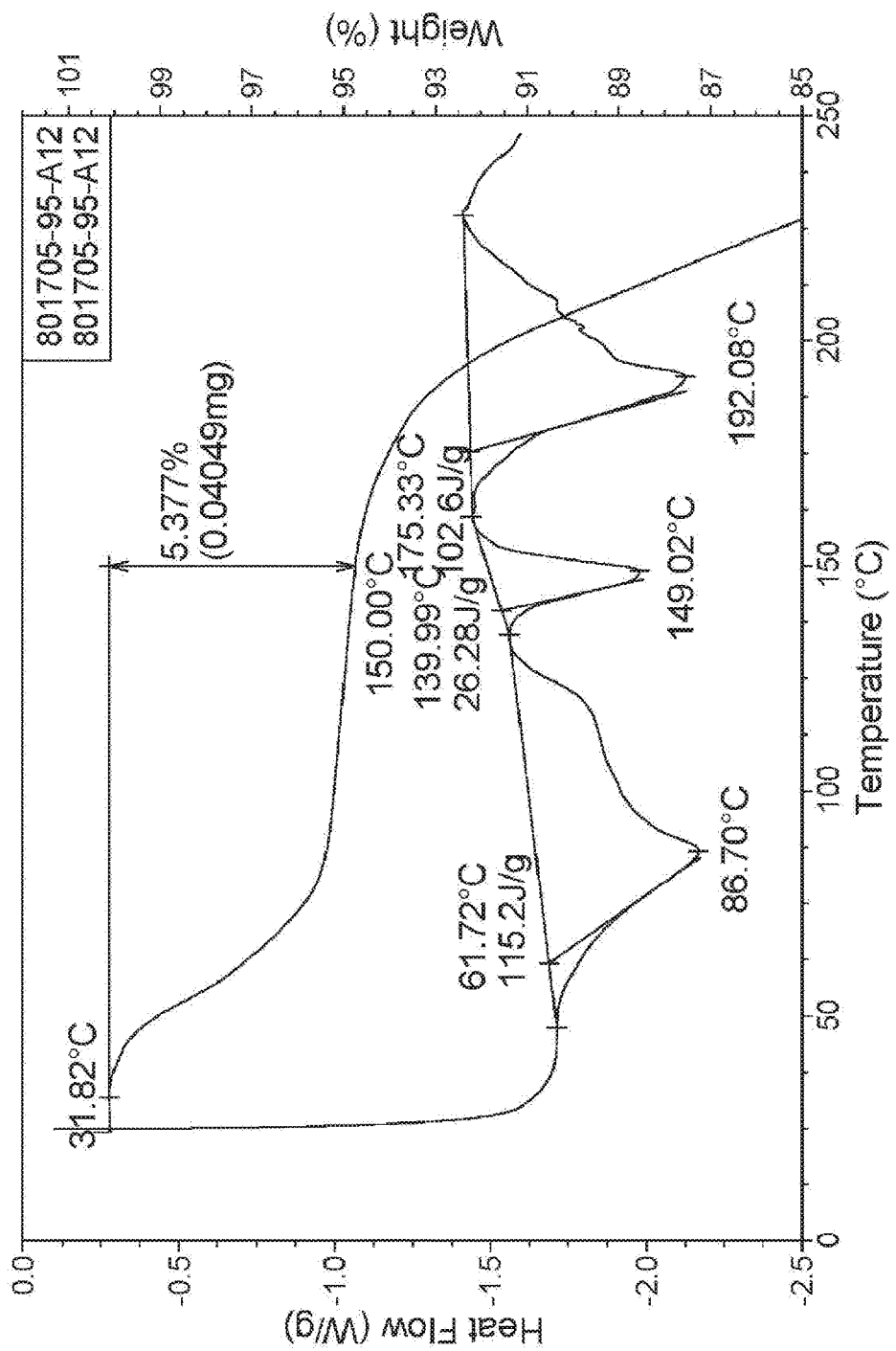
FIG. 14. DSC and TGA profile of Form 6

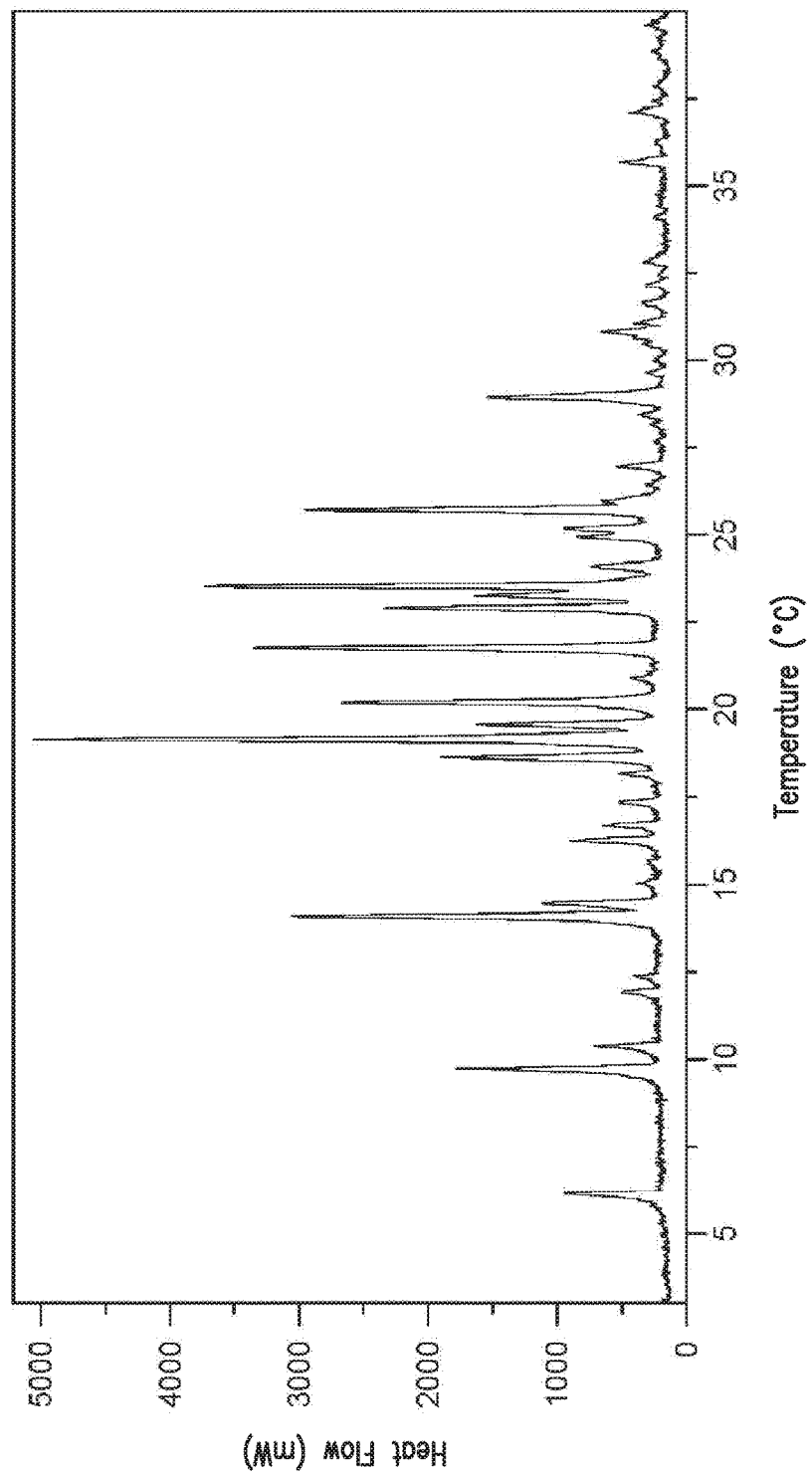
FIG. 15. XRPD pattern of Form 7

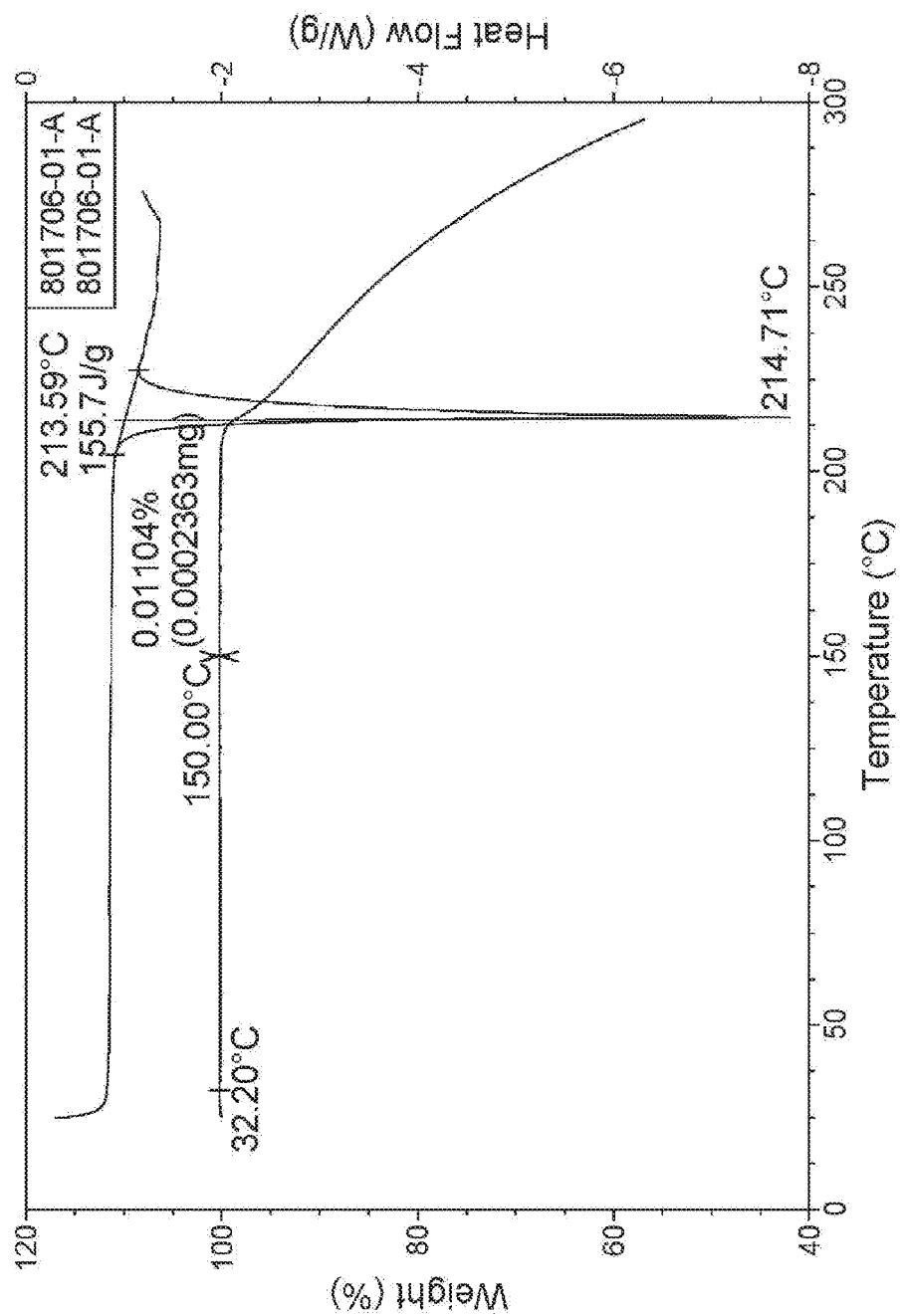
FIG. 16. DSC and TGA profile of Form 7

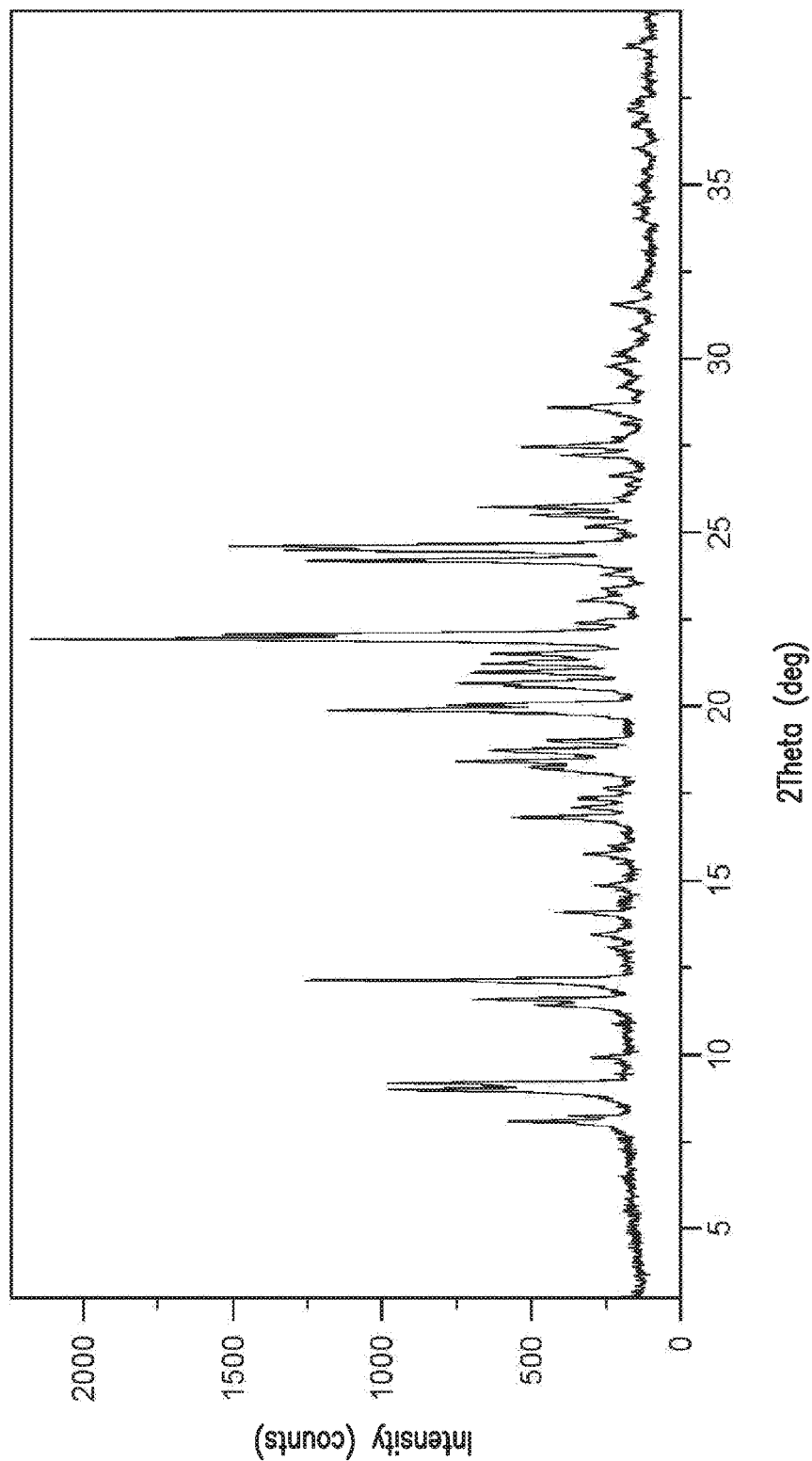
FIG. 17. XRPD pattern of Form 8

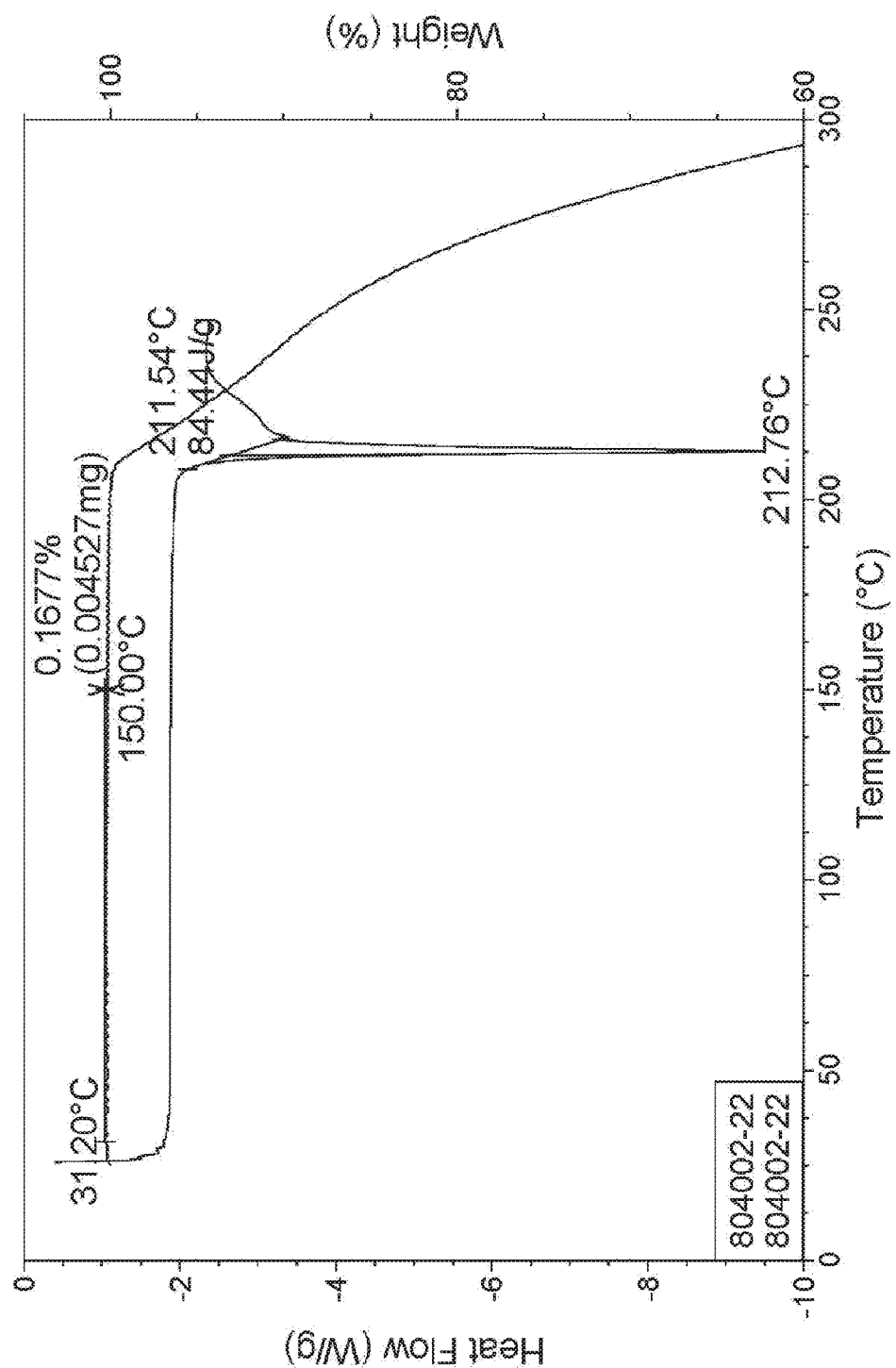
FIG. 18. DSC and TGA profile of Form 8

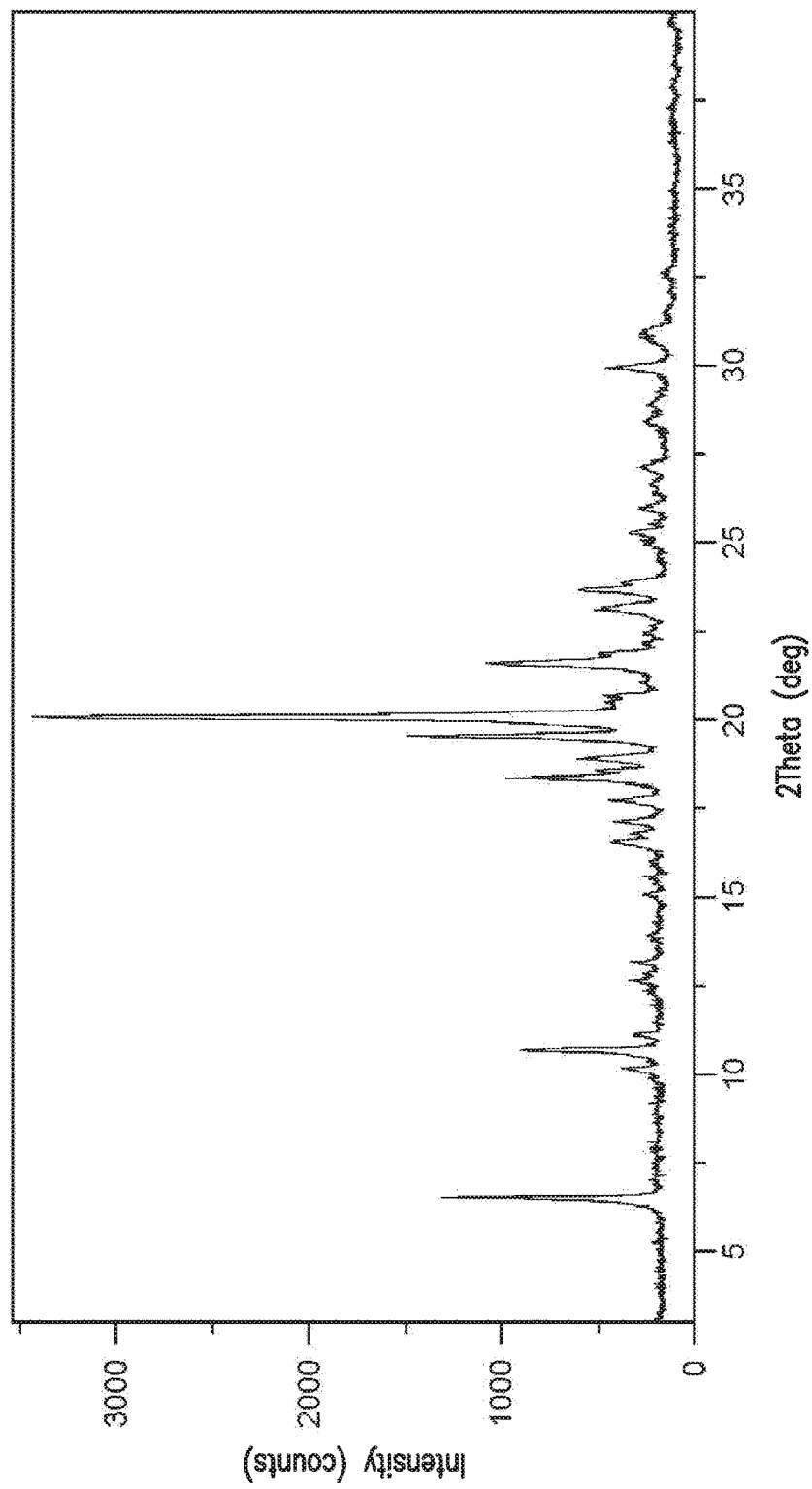
FIG. 19. XRPD pattern of Form 9

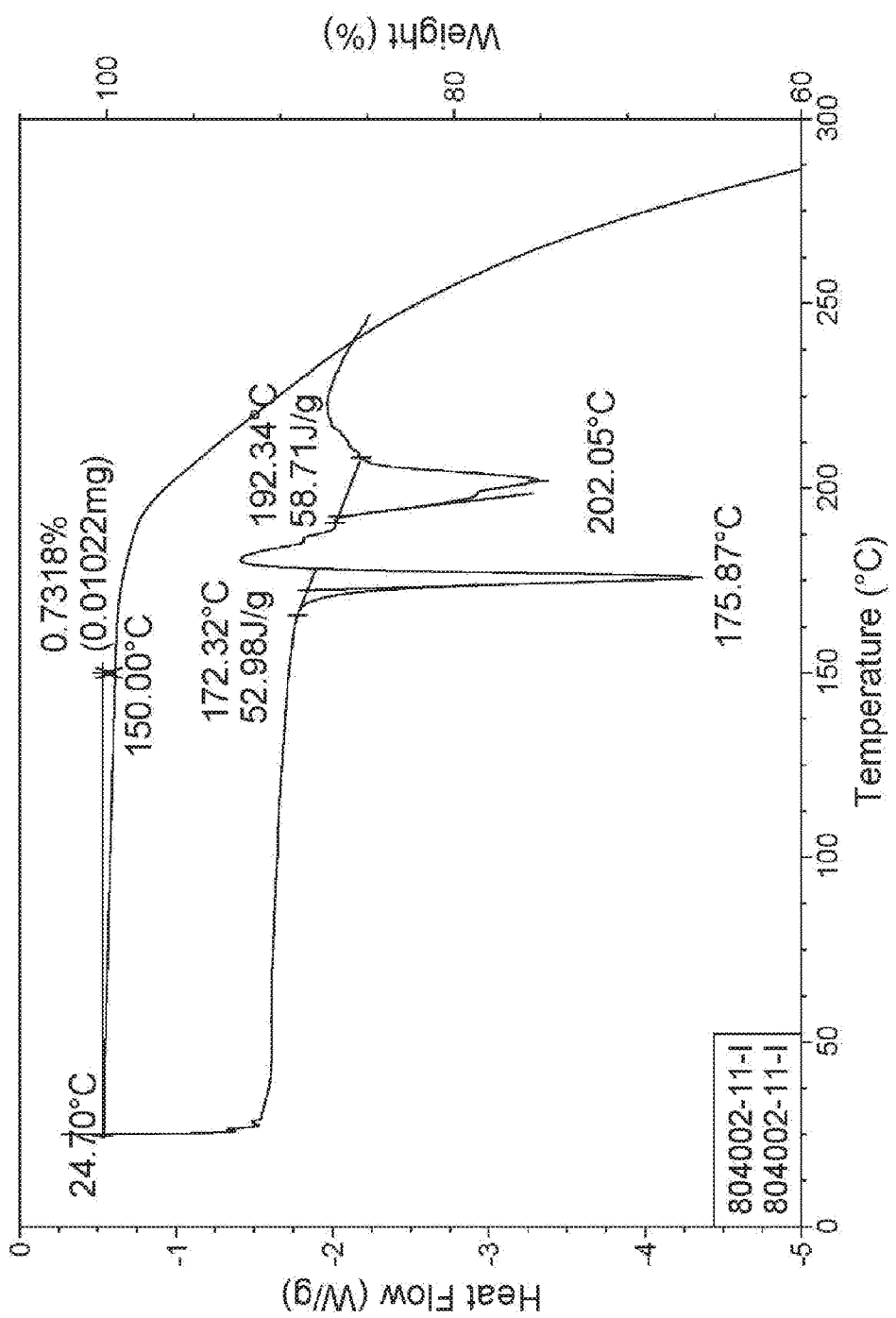
FIG. 20. DSC and TGA profile of Form 9

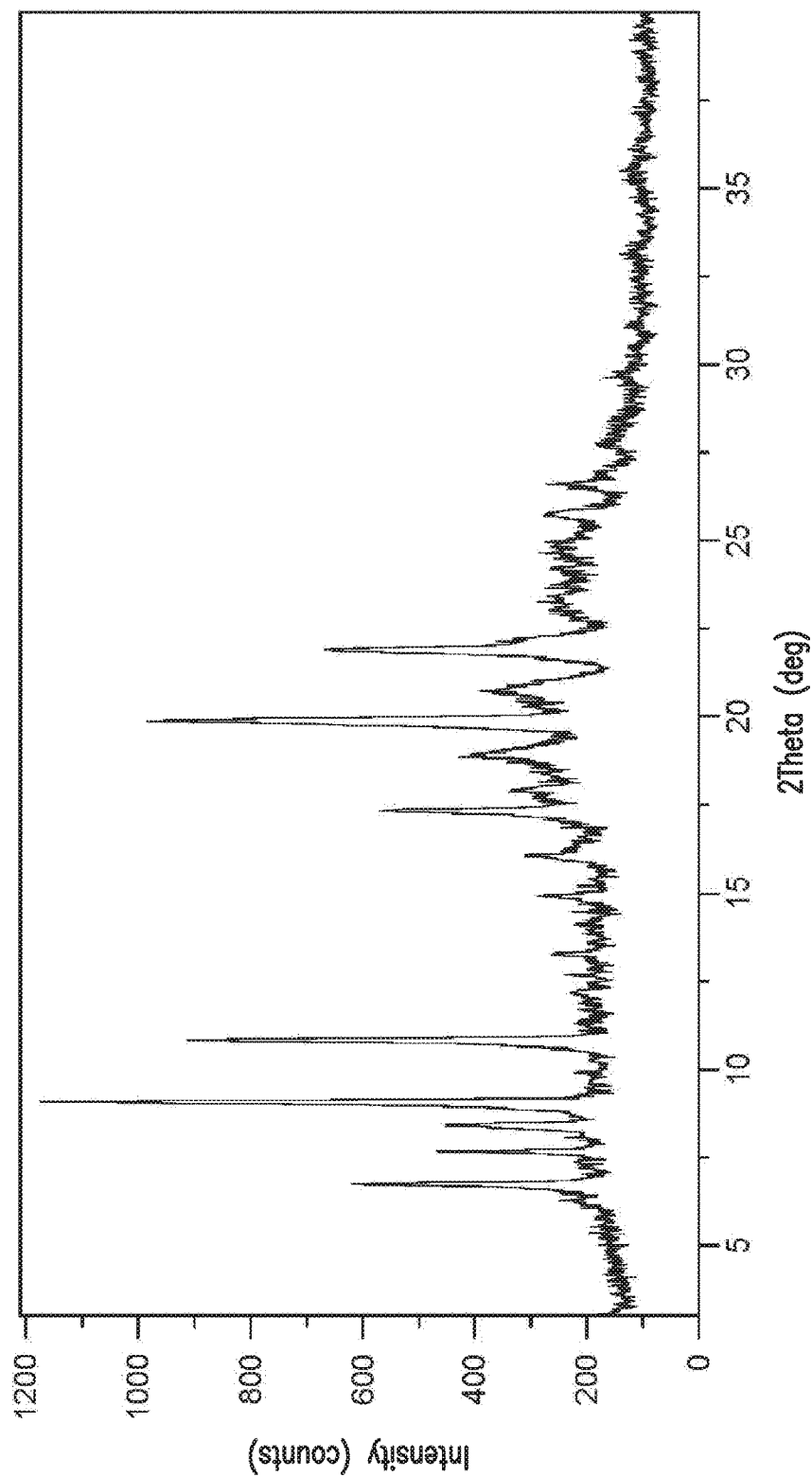
FIG. 21. XRPD pattern of Form 10

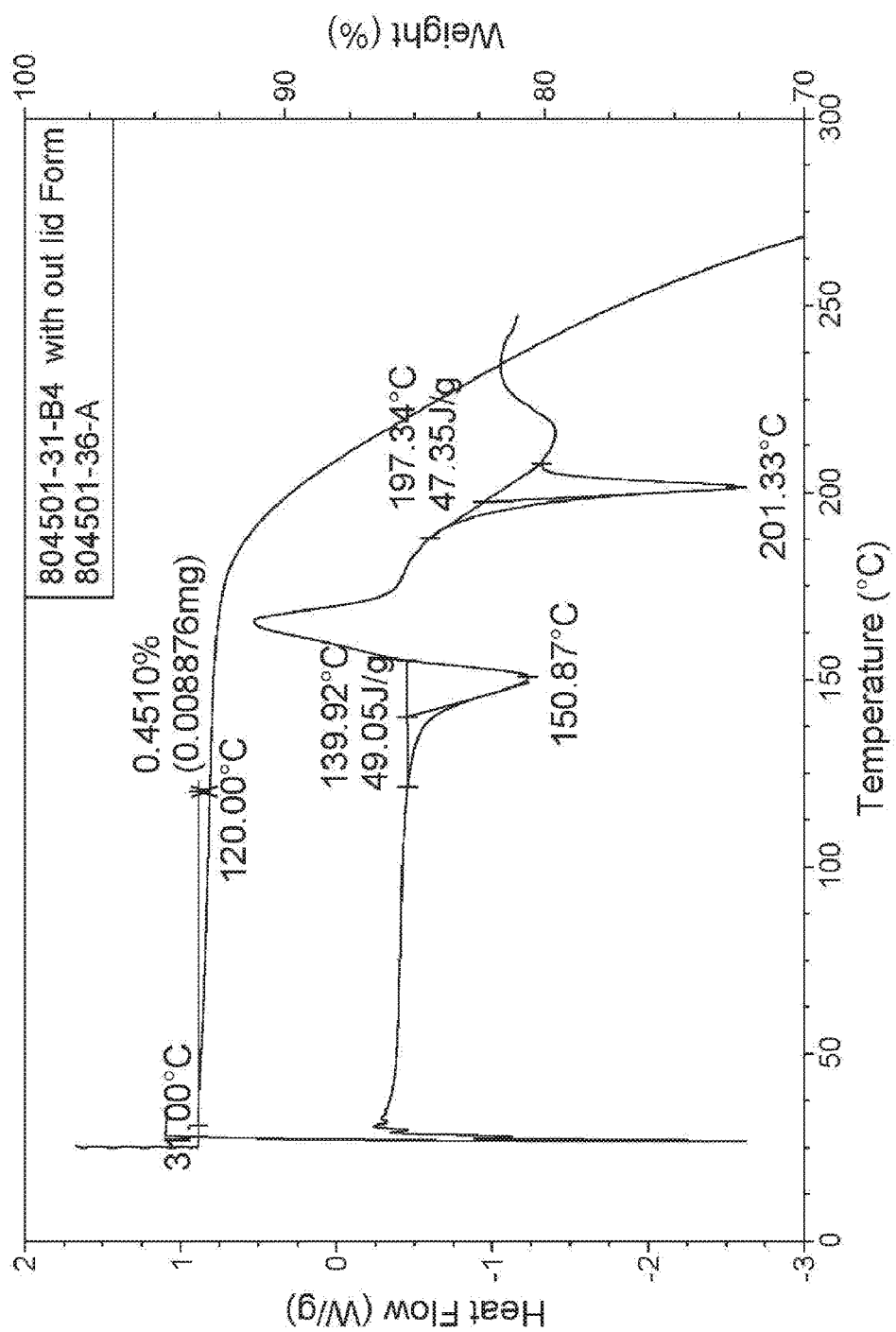
FIG. 22. DSC and TGA profile of Form 10

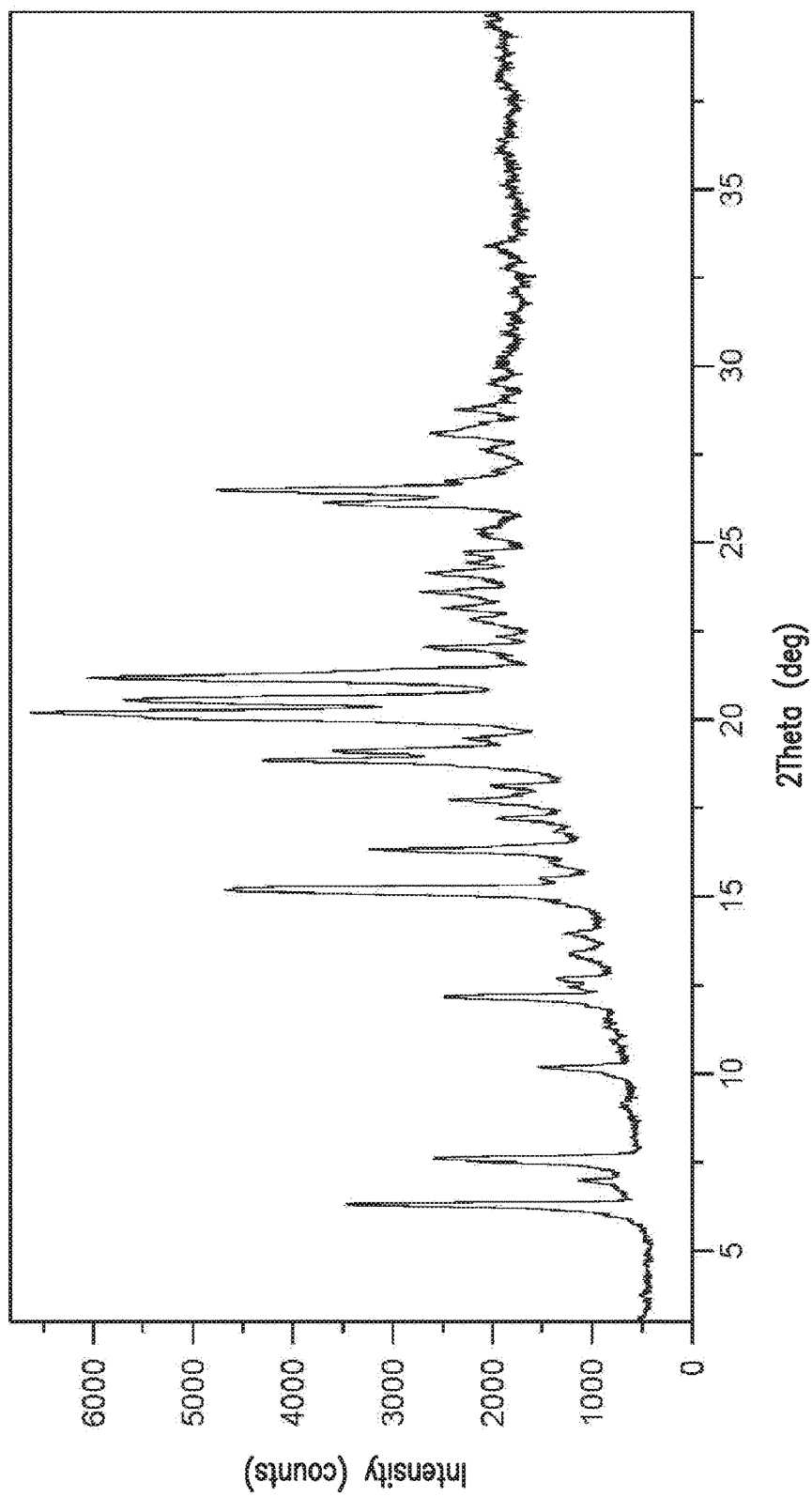
FIG. 23. XRPD pattern of Form 11

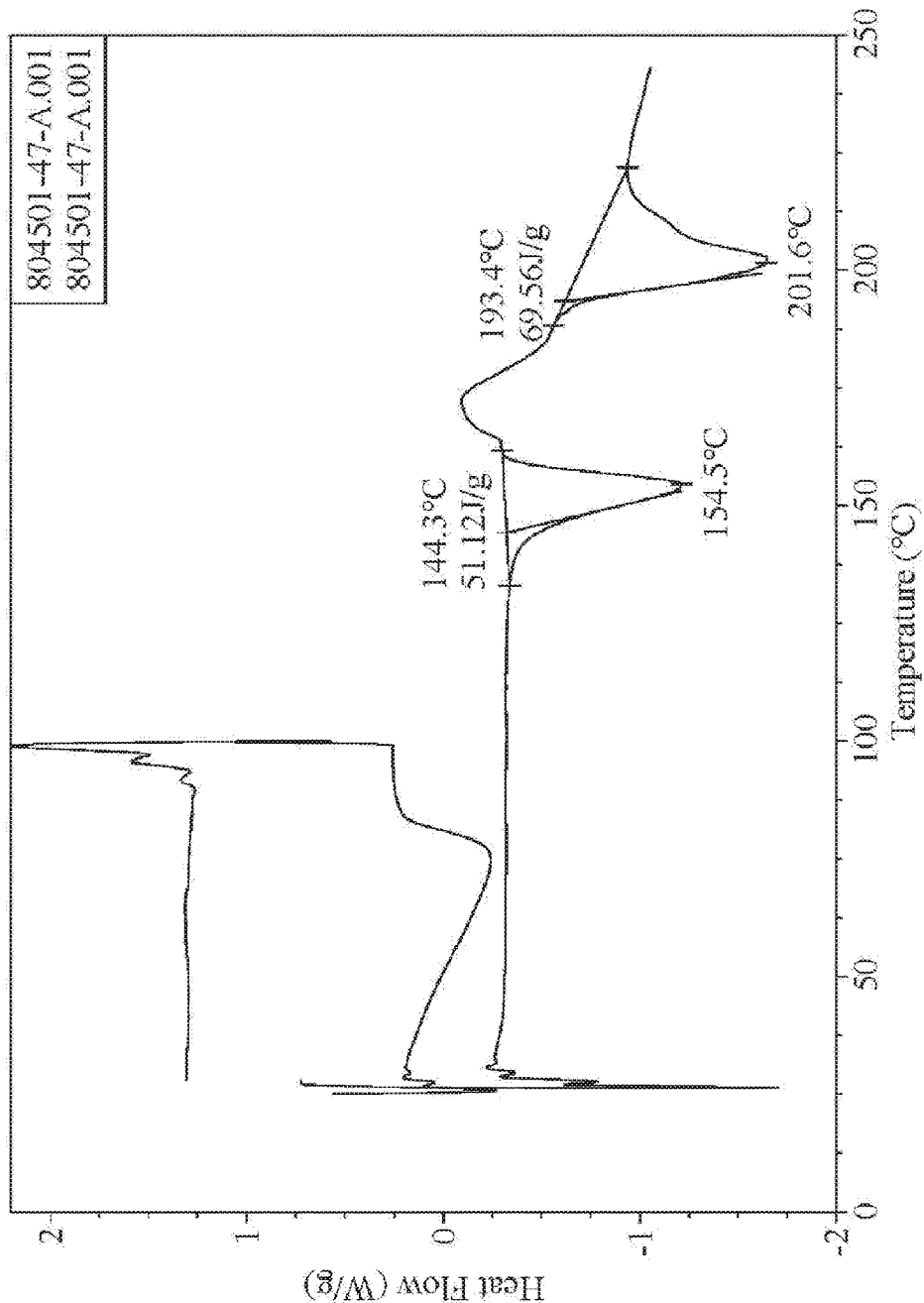
FIG. 24. DSC profile of Form 11

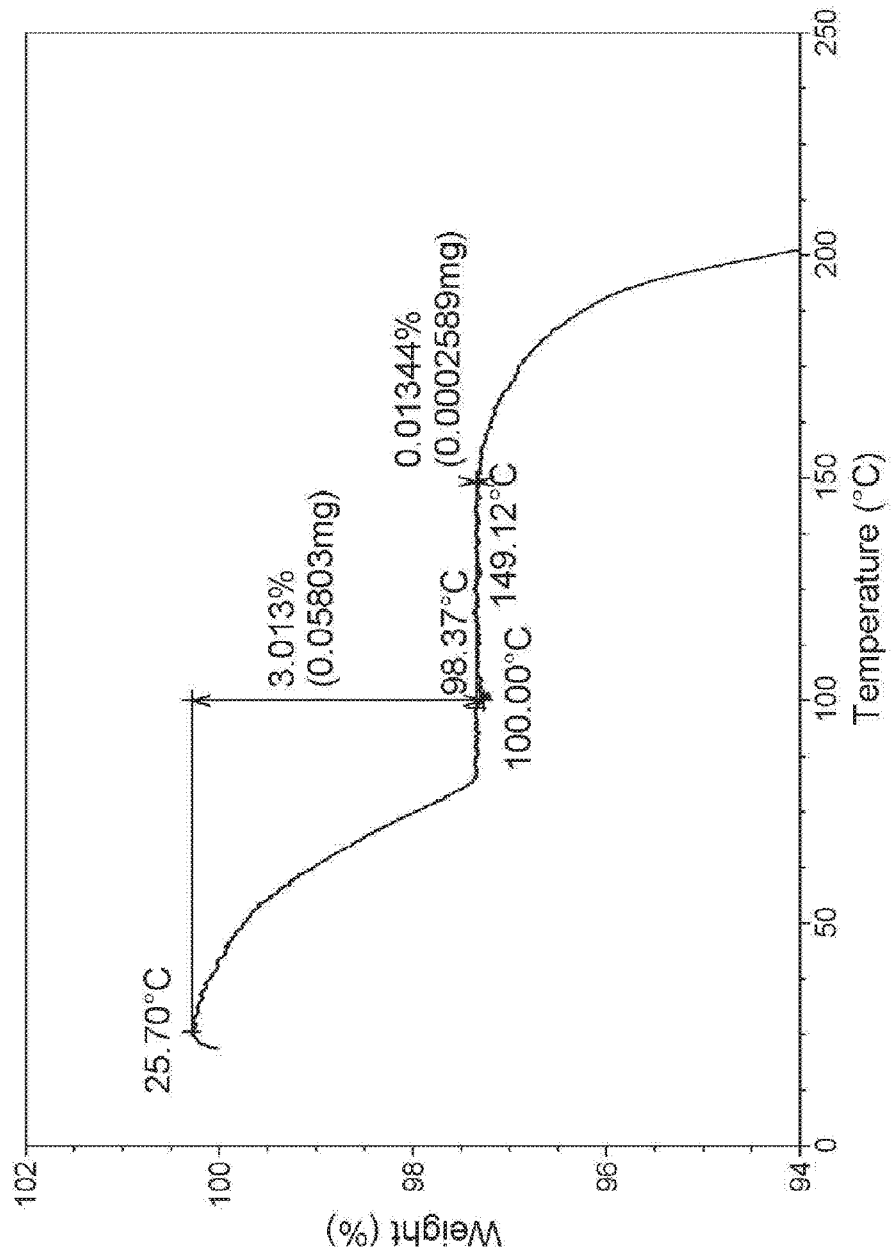
FIG. 25. TGA profile of Form 11

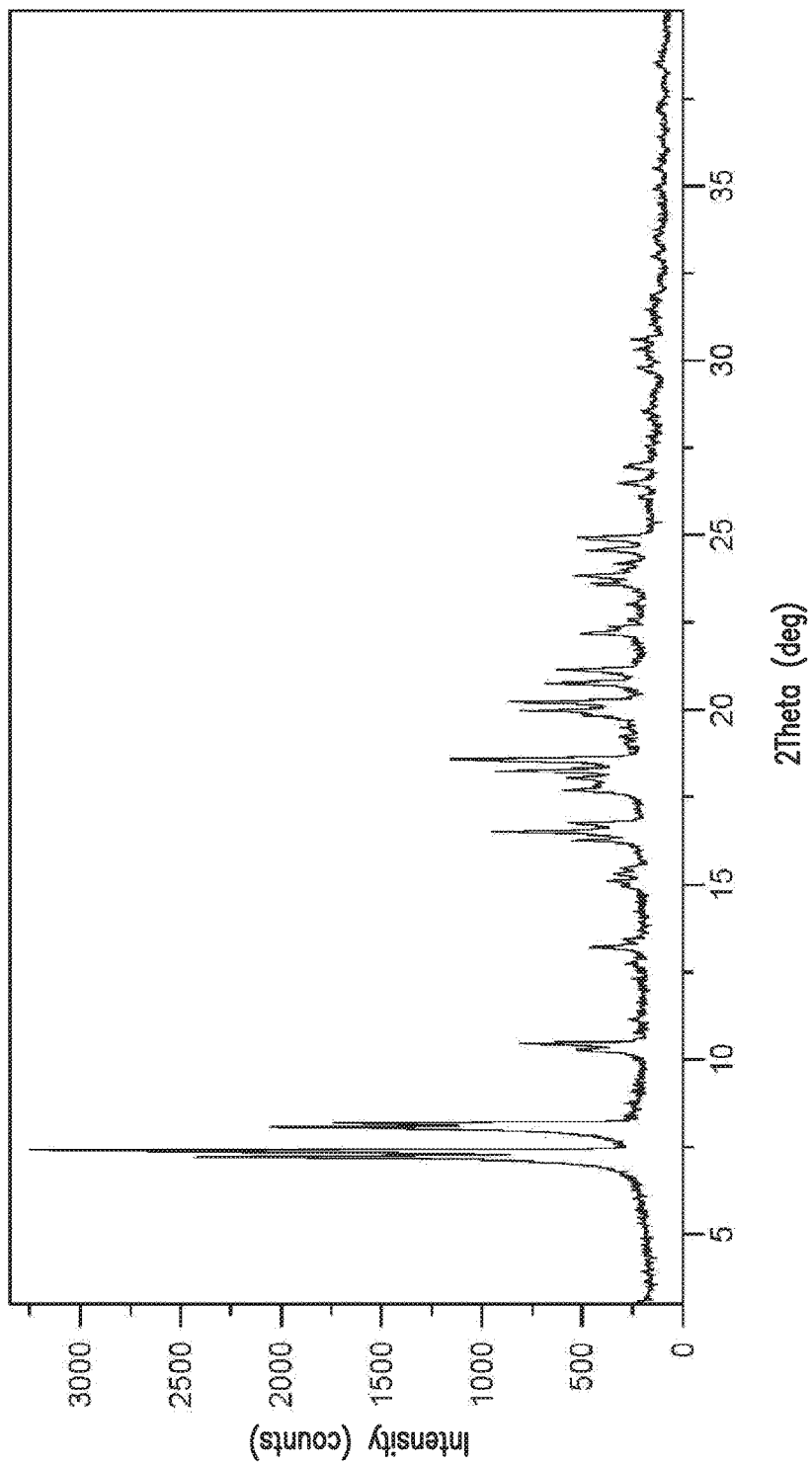
FIG. 26. XRPD of Form 12

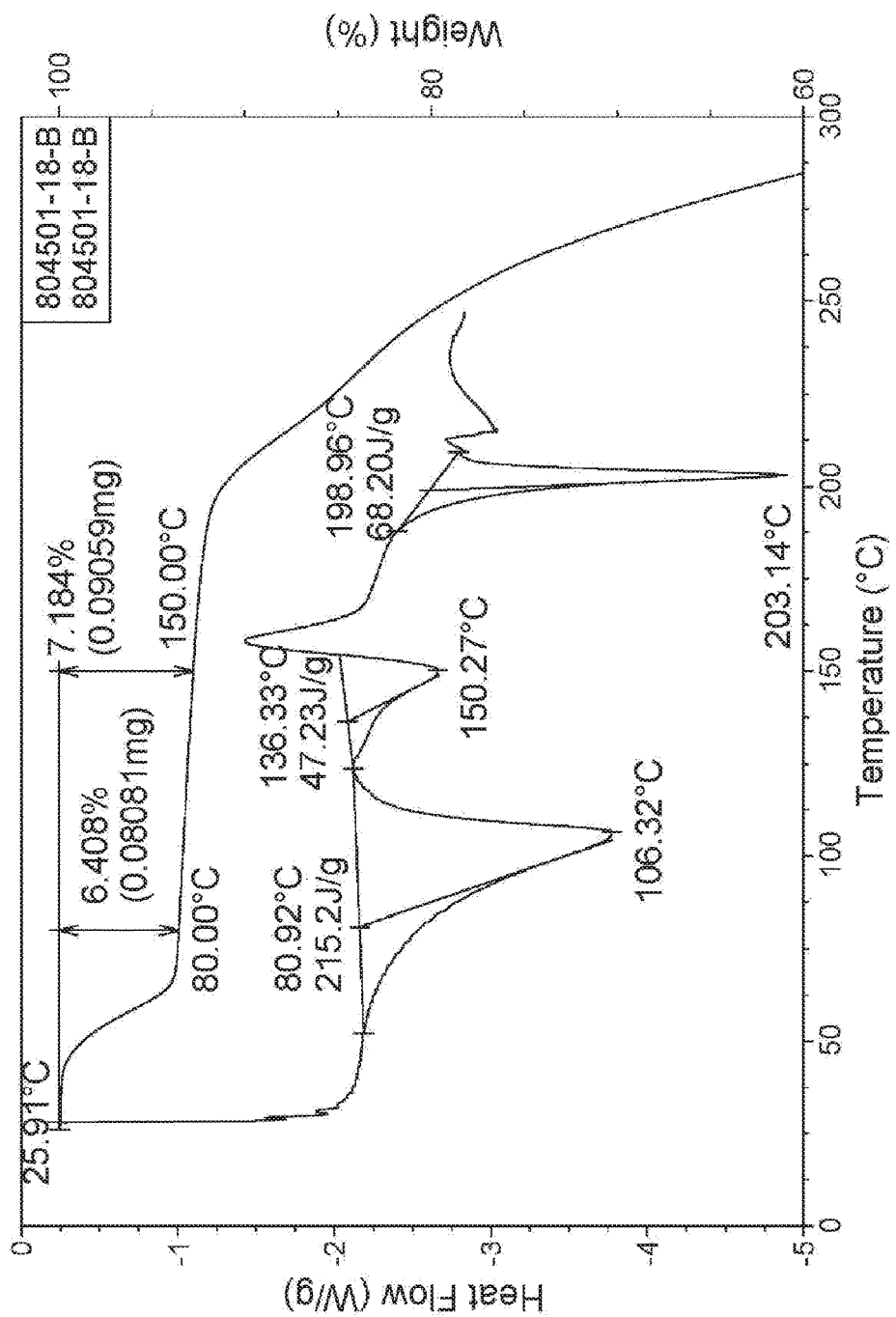
FIG. 27. DSC and TGA profile of Form 12

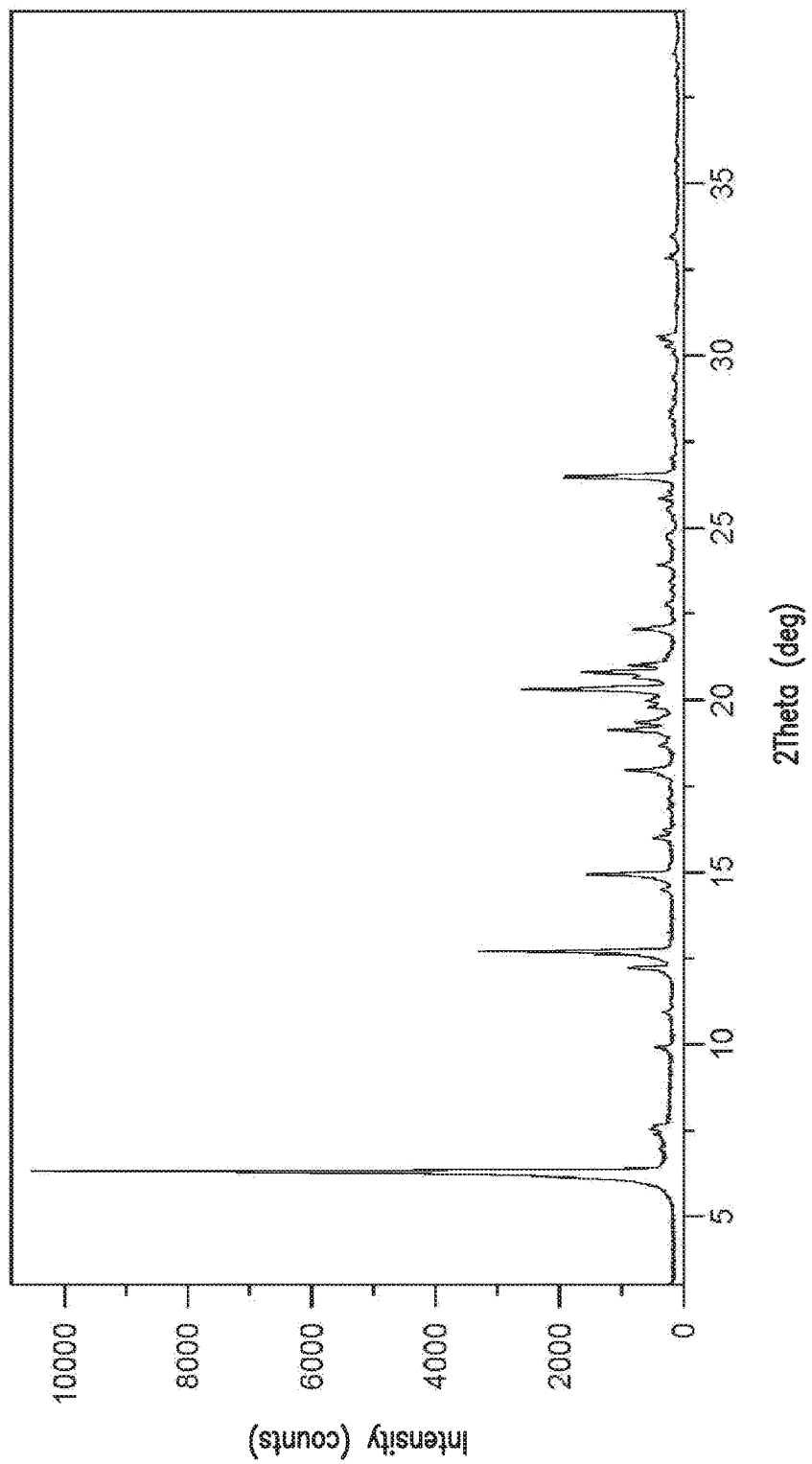
FIG. 28. XRPD of Form 13

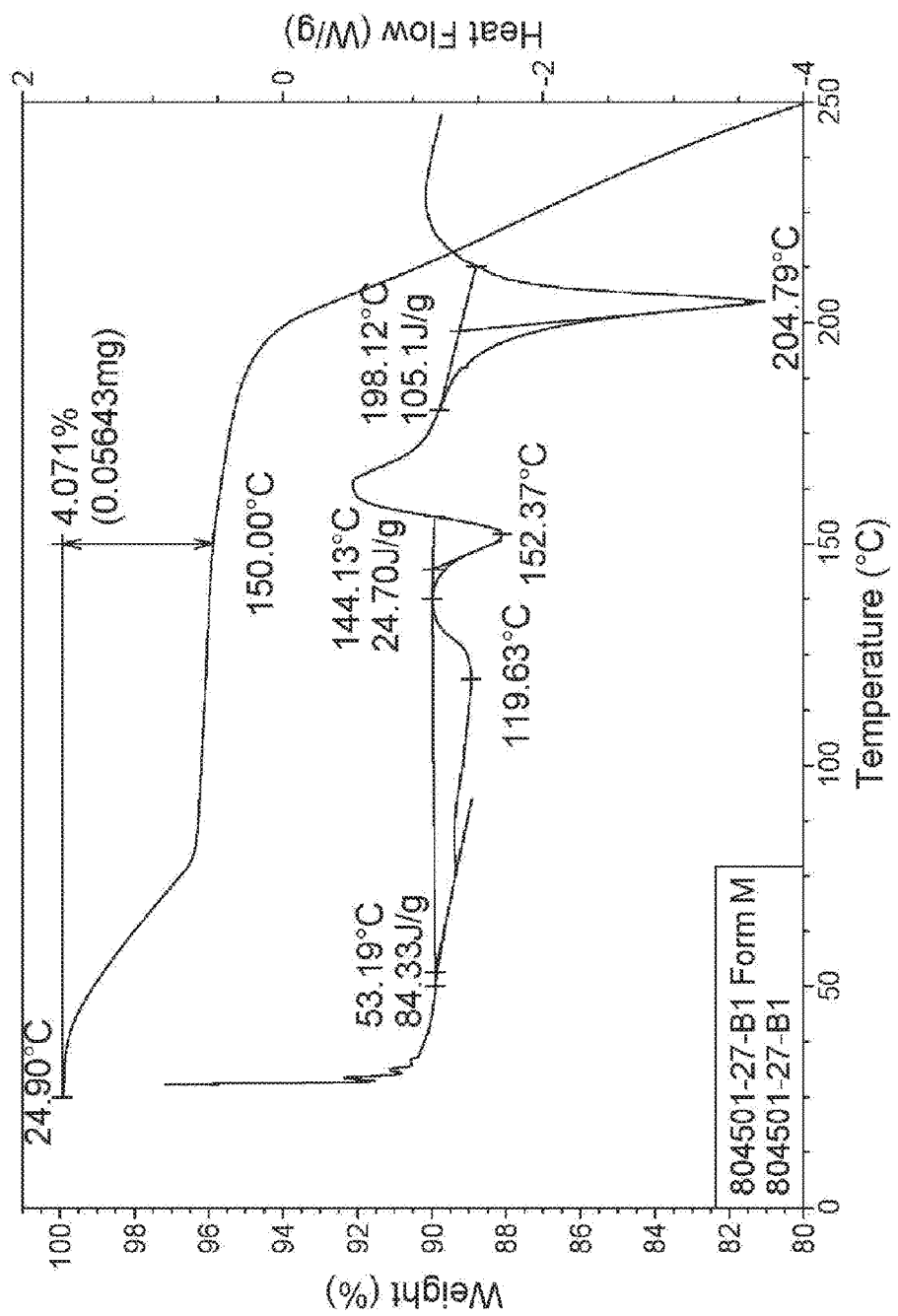
FIG. 29. DSC and TGA profile of Form 13

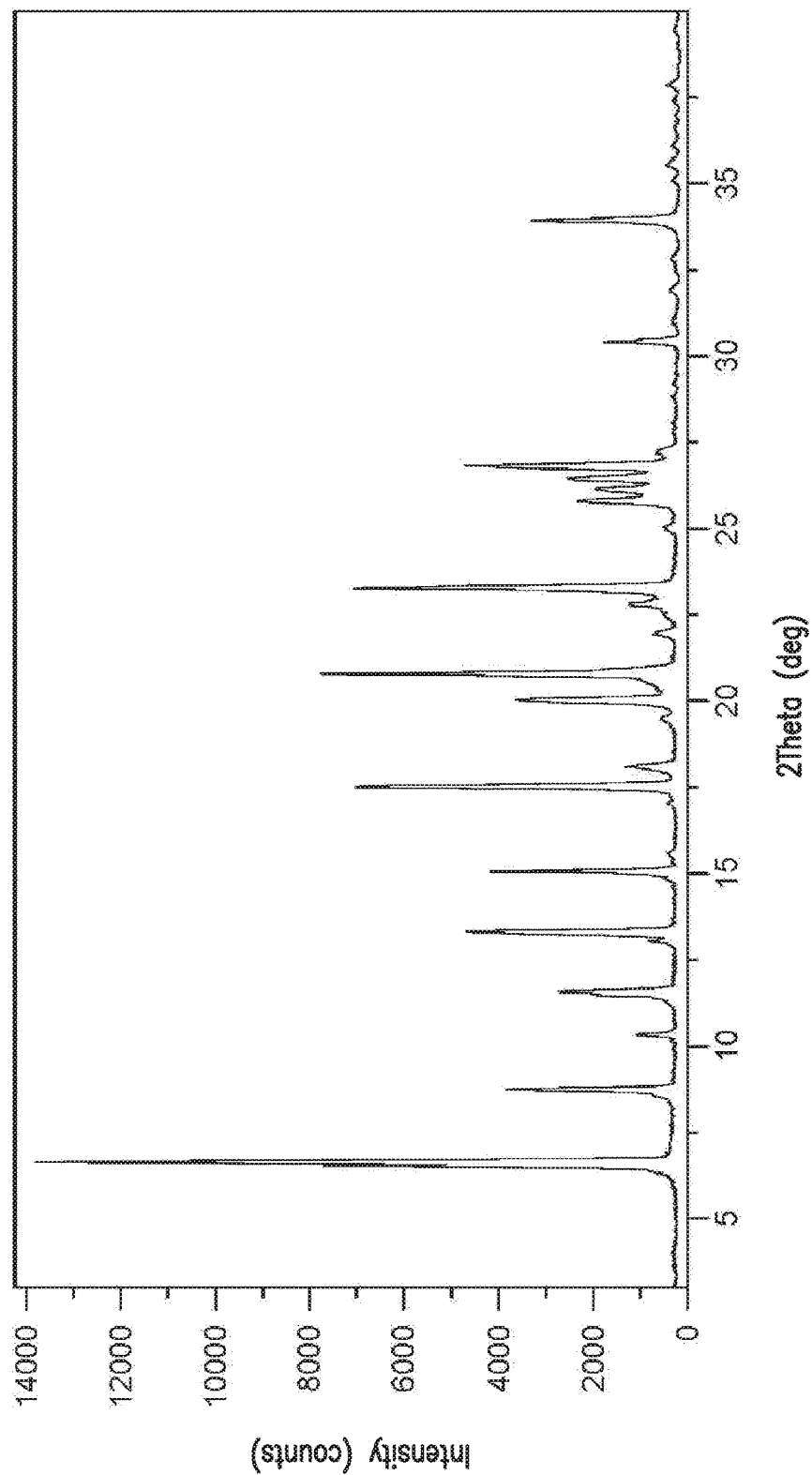
FIG. 30. XRPD pattern of Form 14

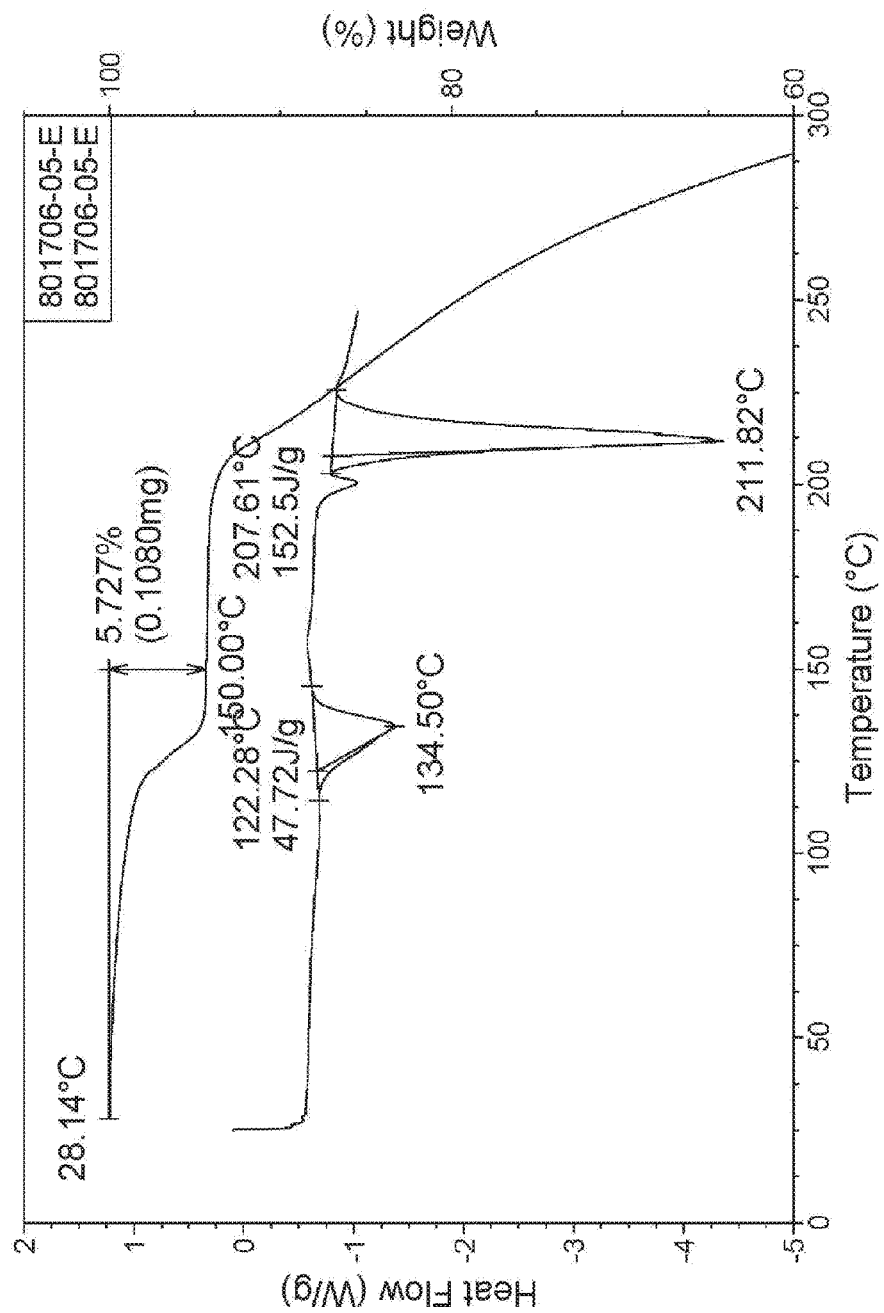
FIG. 31. DSC and TGA profile of Form 14

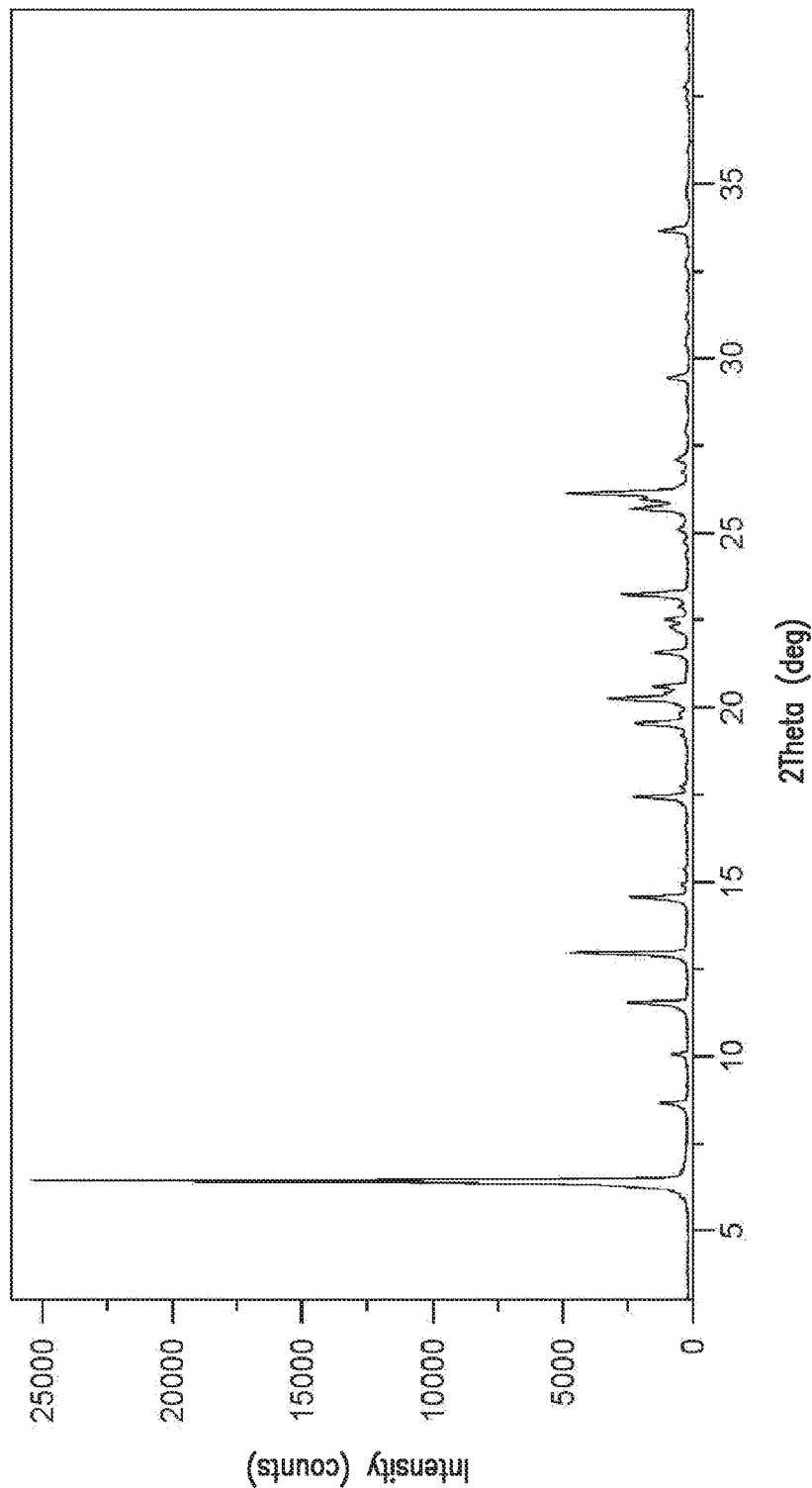
FIG. 32. XRPD pattern of Form 15

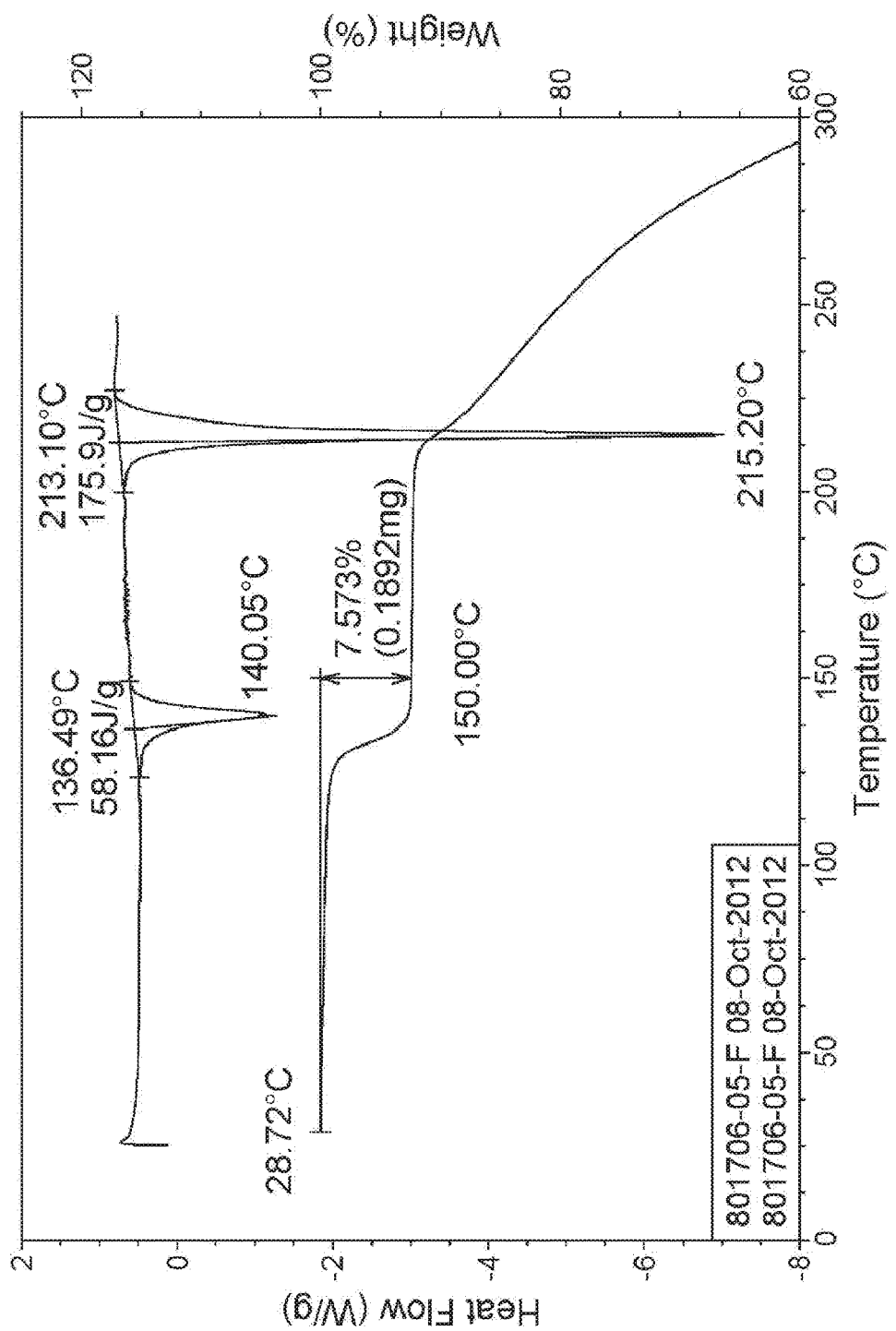
FIG. 33. DSC and TGA profile of Form 15

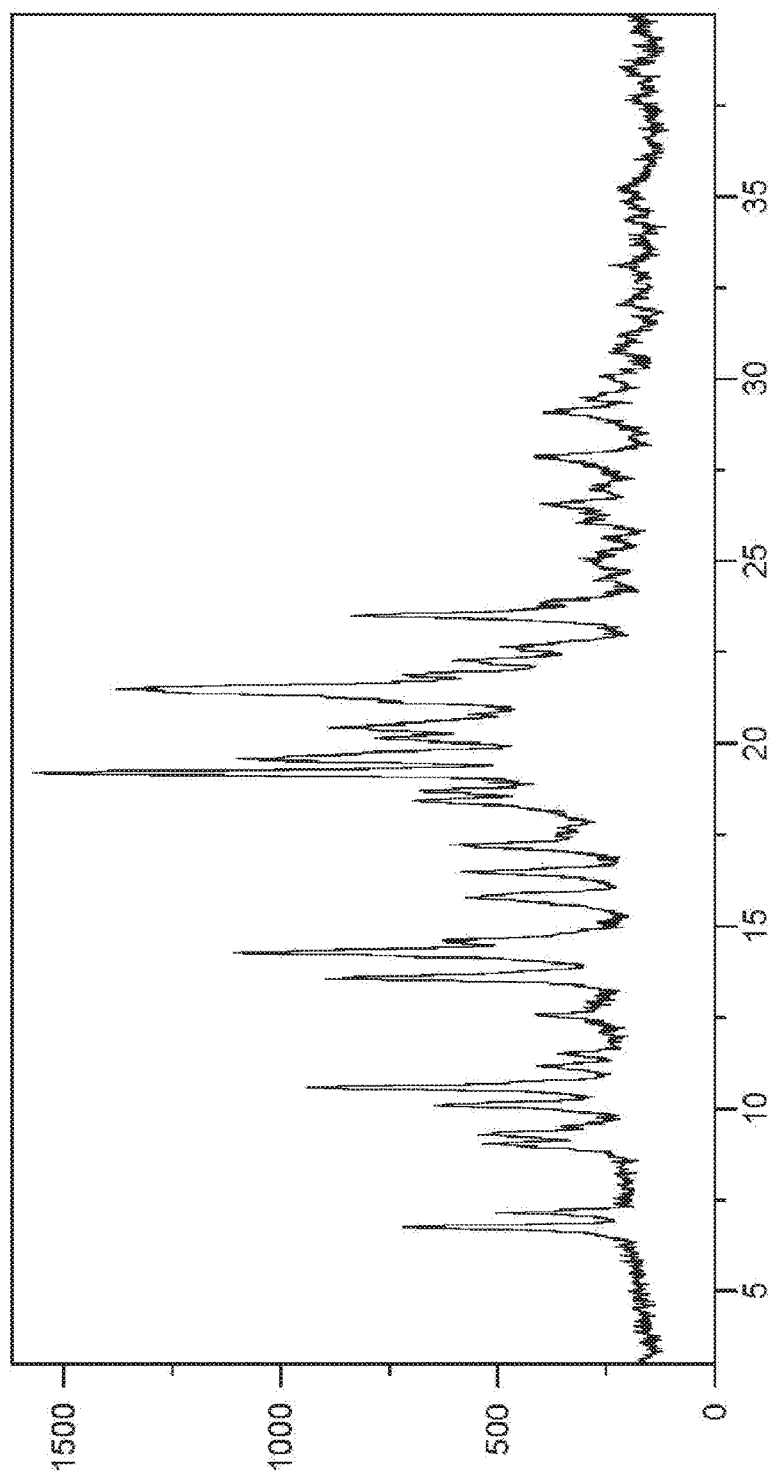
FIG. 34. XRPD pattern of Form 16

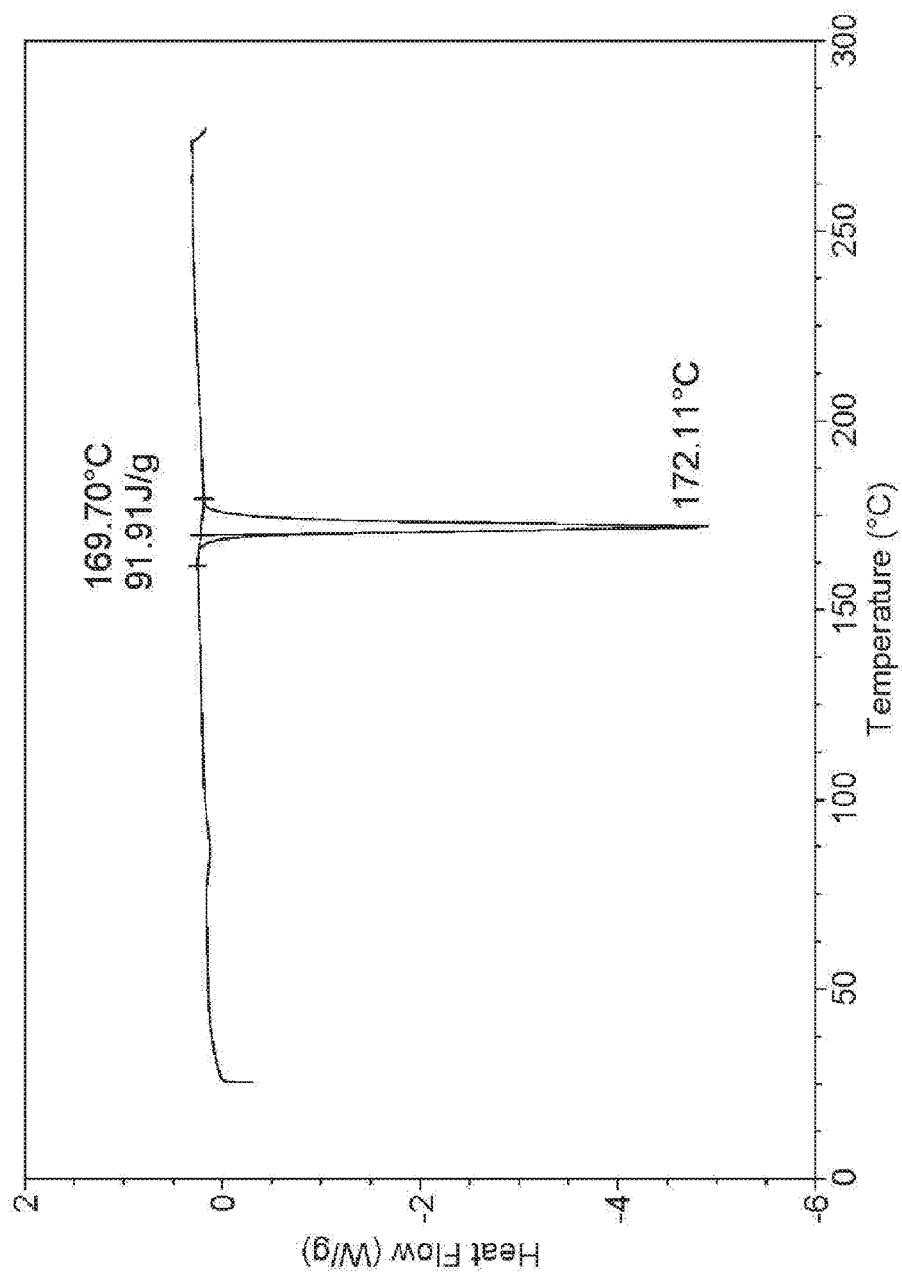
FIG. 35. DSC profile of Form 16

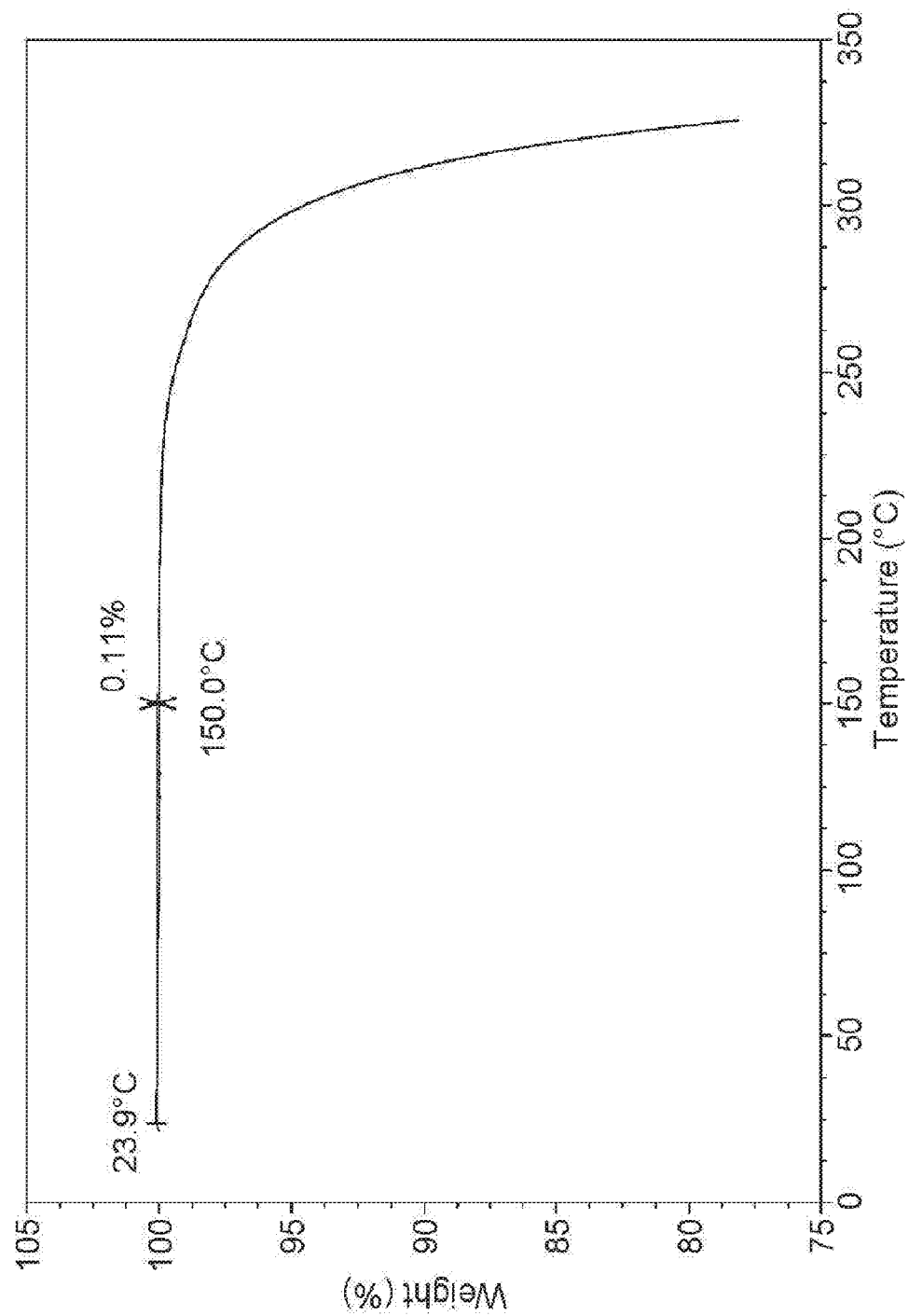
FIG. 36. TGA profile of Form 16

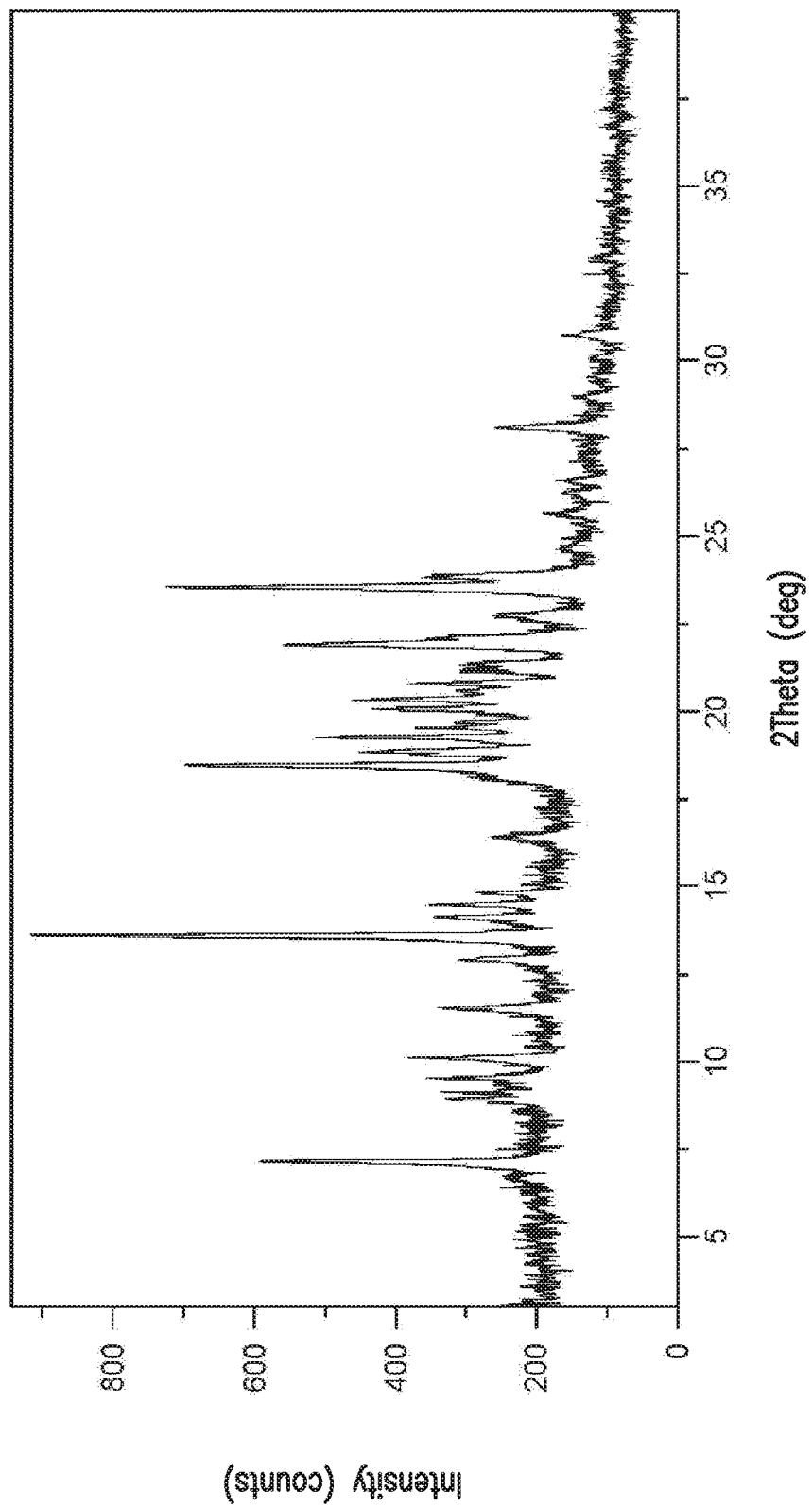
FIG. 37. XRPD pattern of Form 17

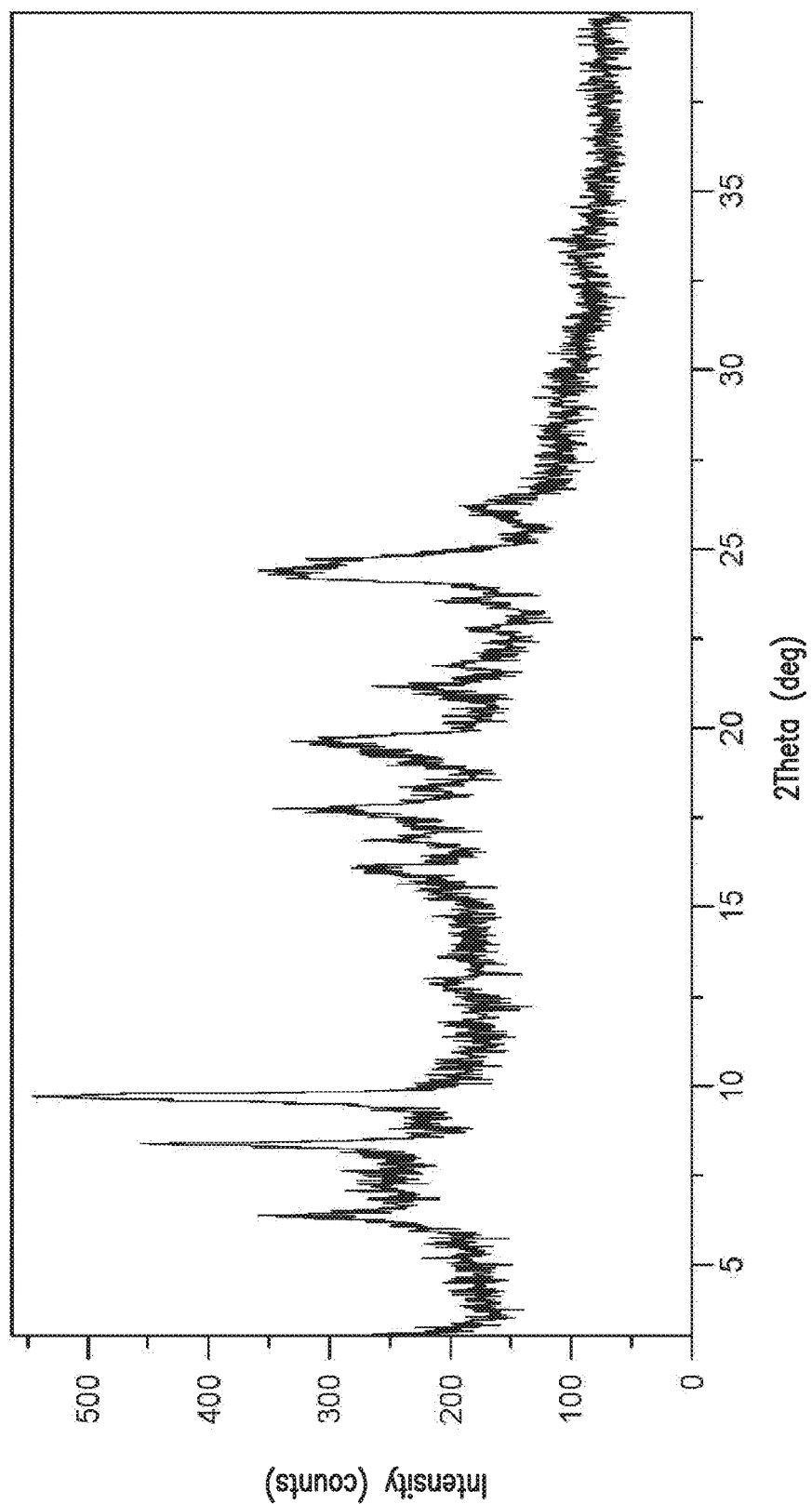
FIG. 38. XRPD pattern of Form 18

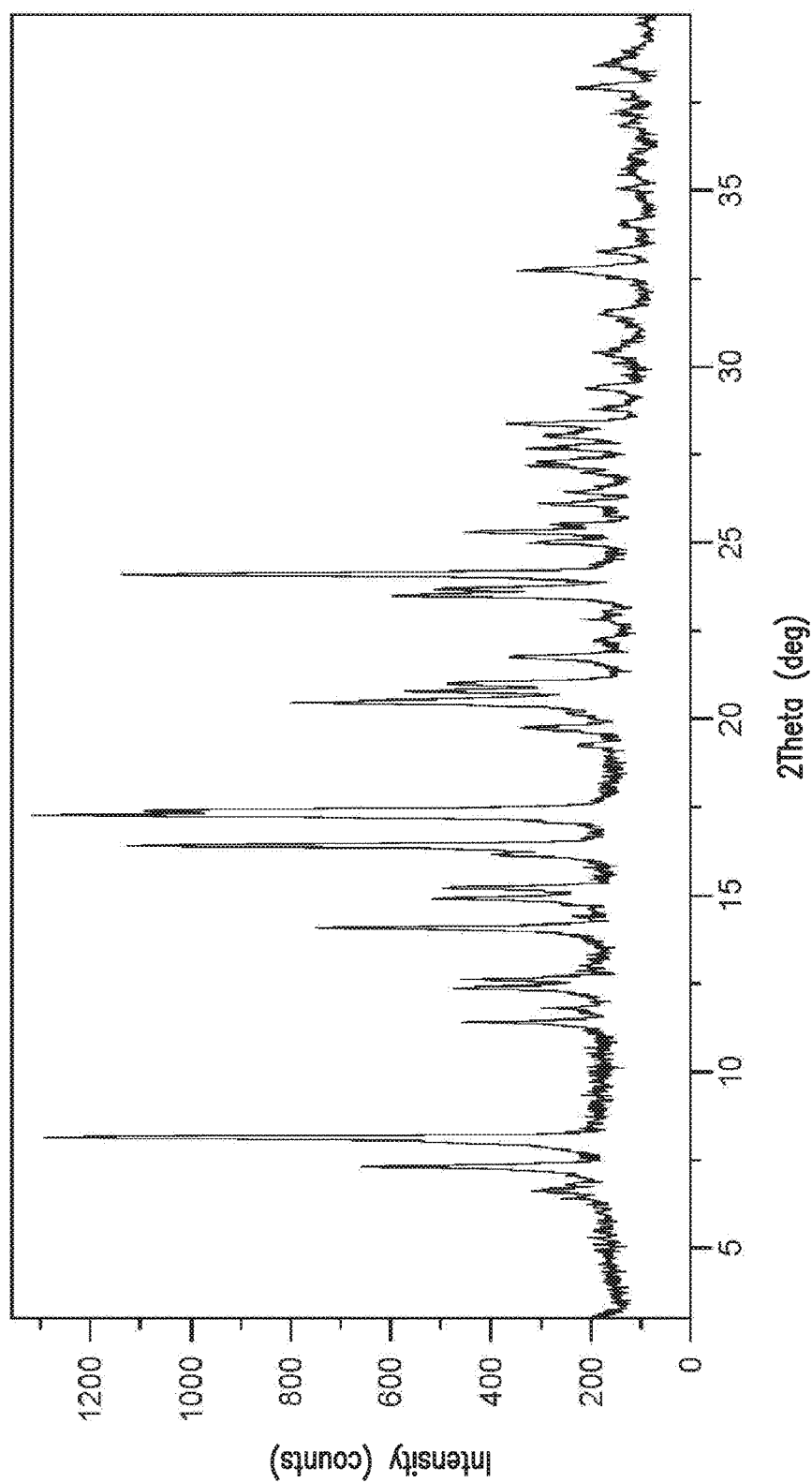
FIG. 39. XRPD pattern of Form 19

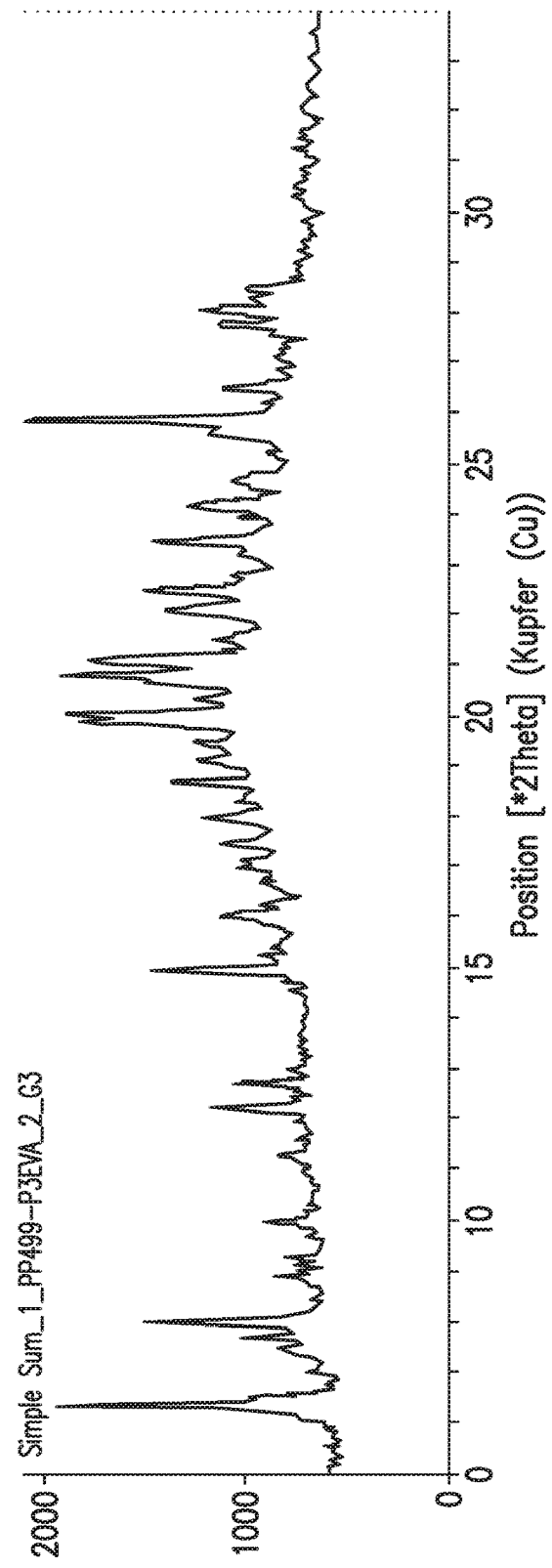
FIG. 40. superimposed XRPD pattern of Form 20

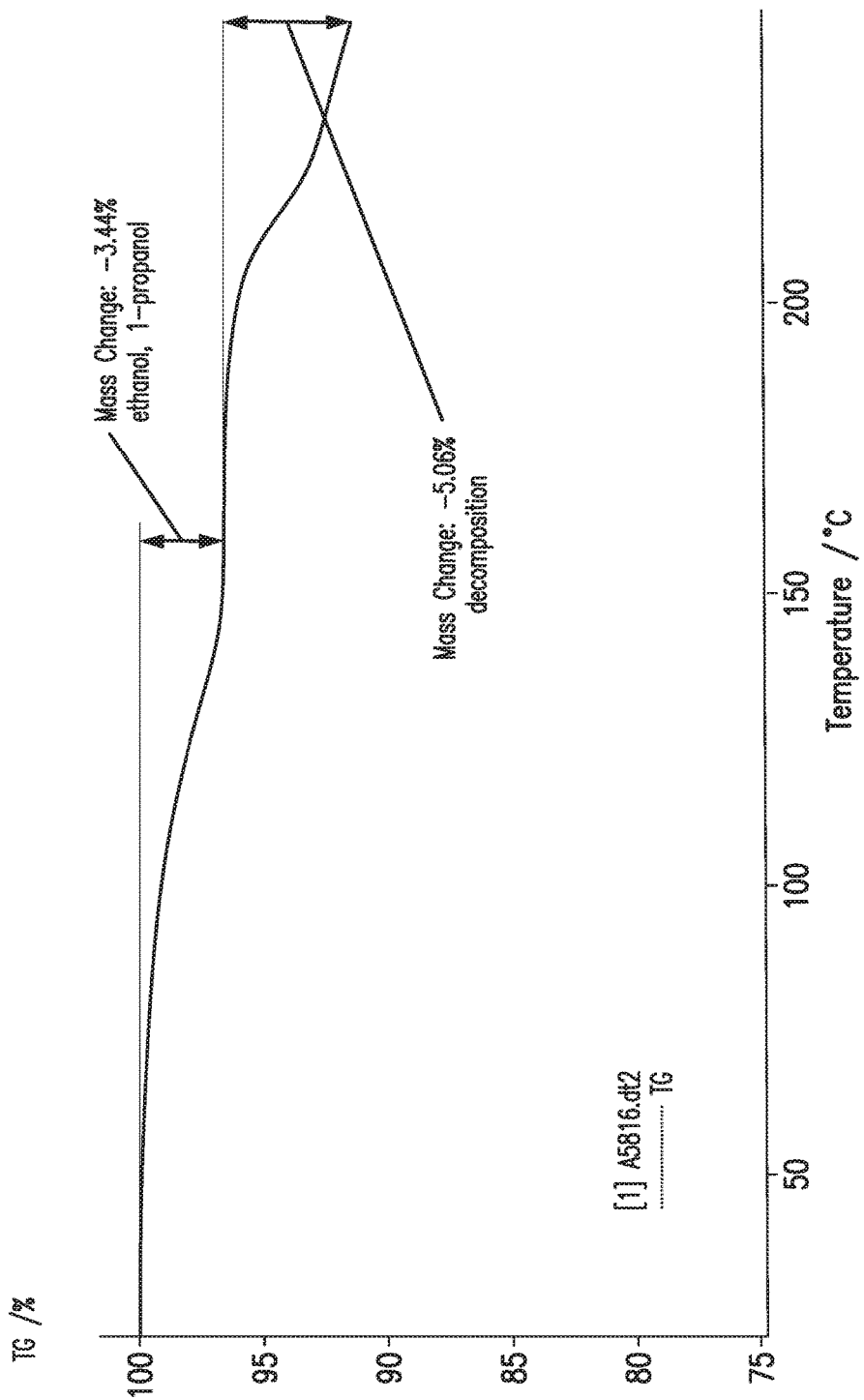
FIG. 41. TGA profile of Form 20

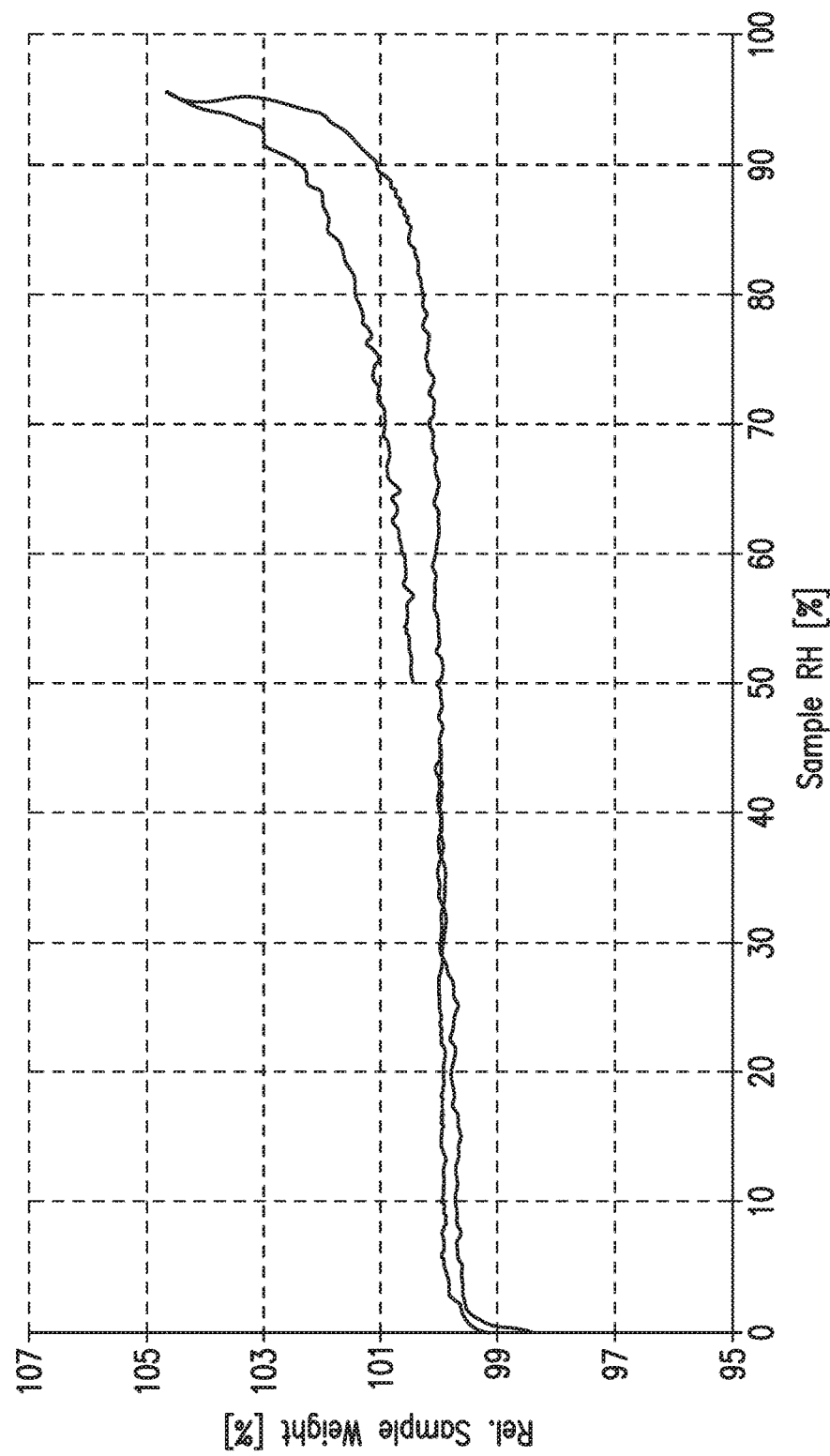
FIG. 42. DVS profile of Form 20

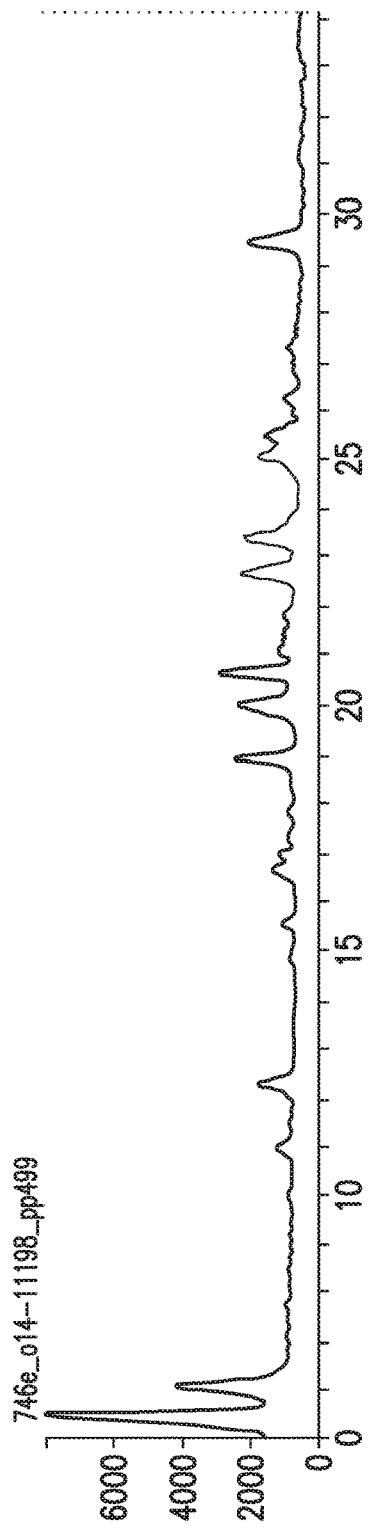
FIG. 43. XRPD pattern of Form 21

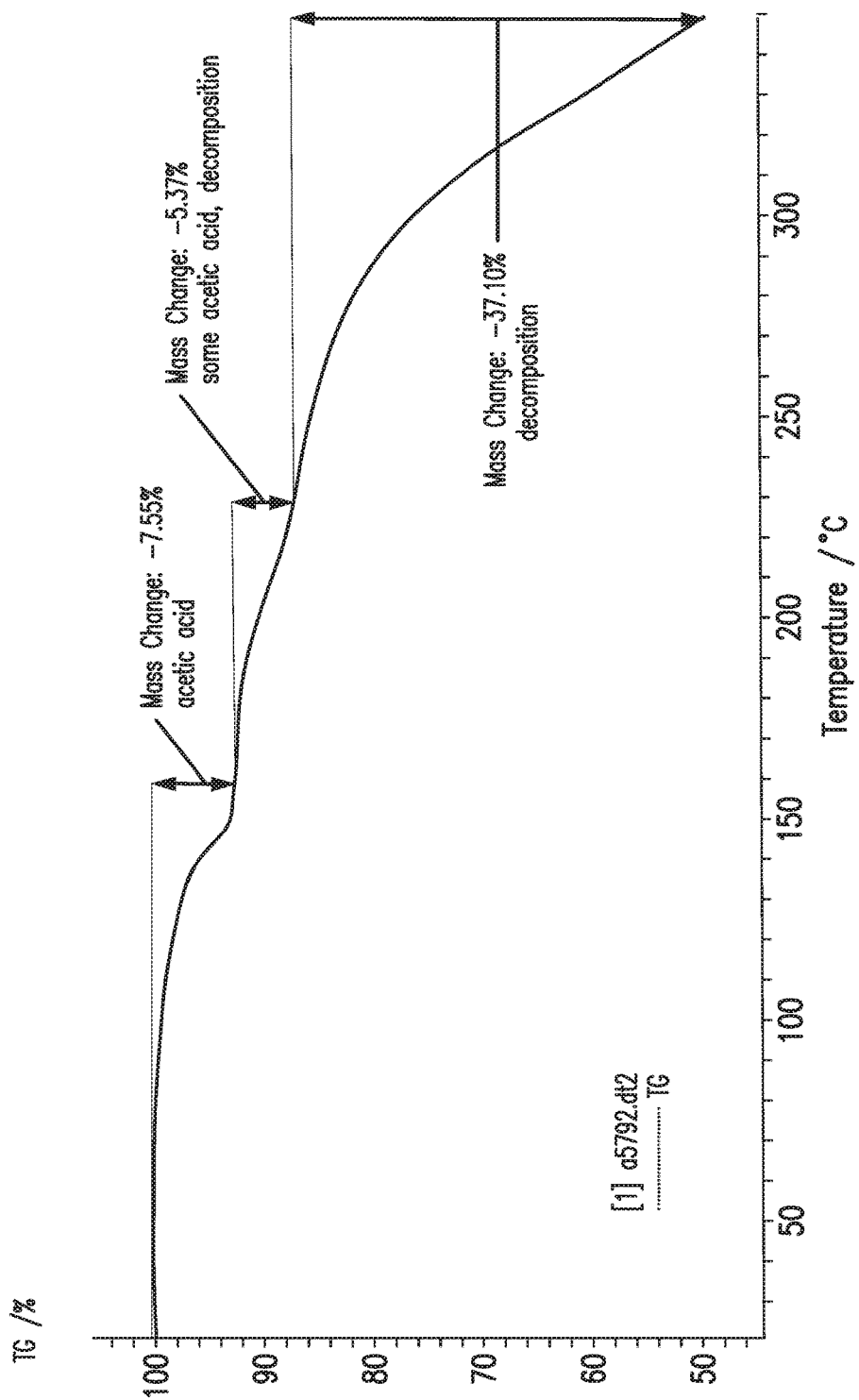
FIG. 44. TGA profile of Form 21

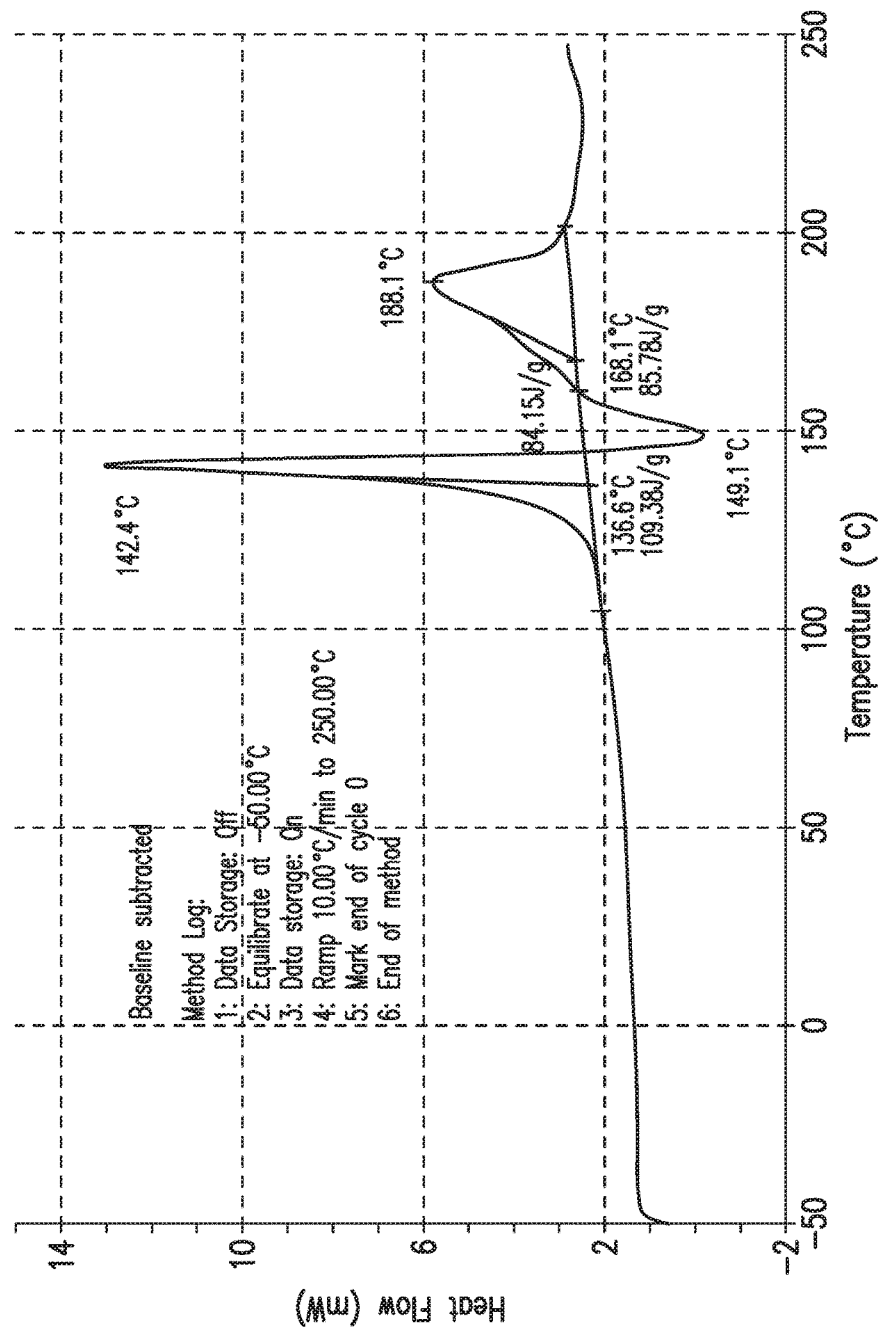
FIG. 45. DSC profile of Form 21

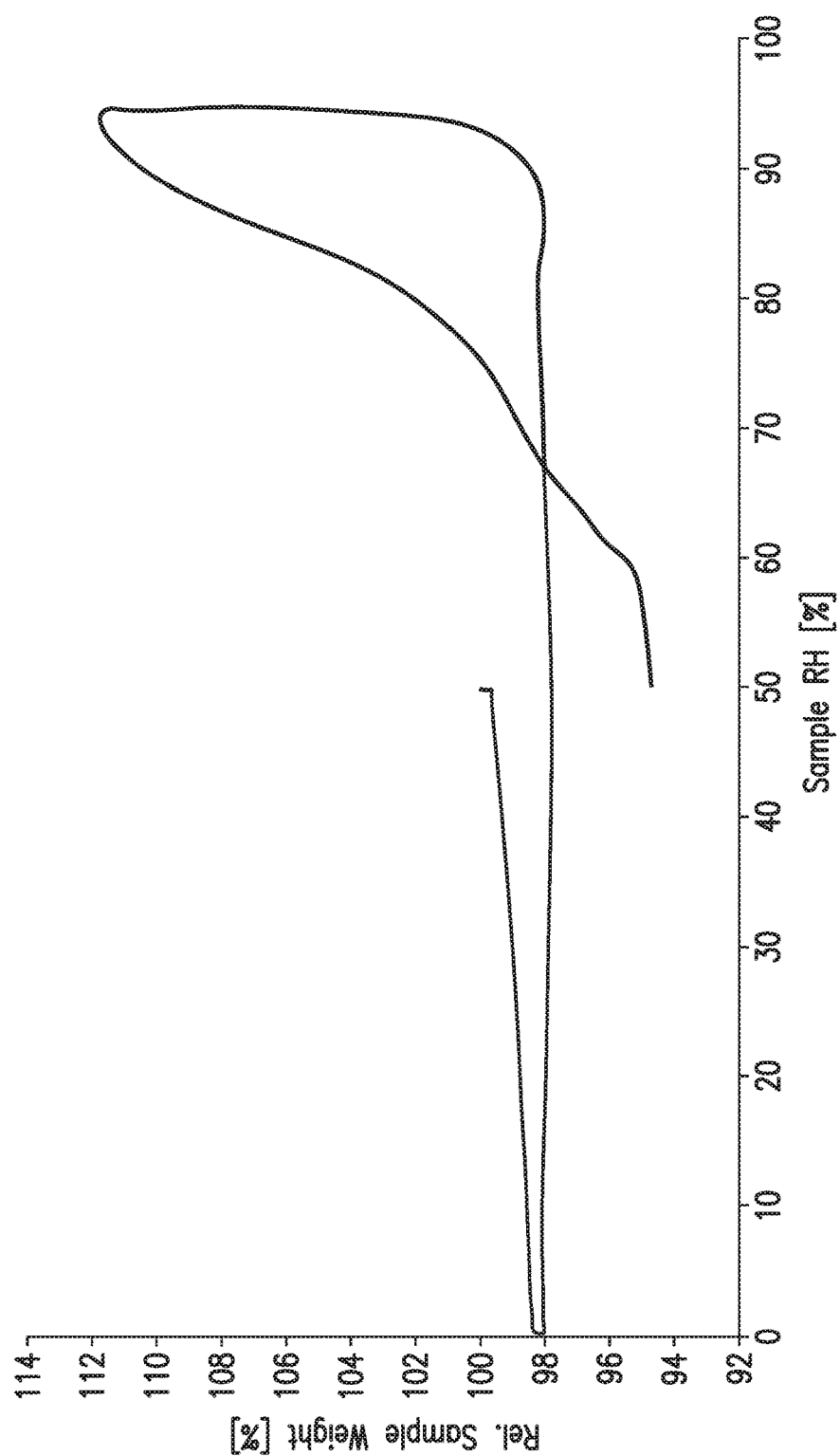
FIG. 46. DVS profile of Form 21

THERAPEUTICALLY ACTIVE COMPOUNDS AND THEIR METHODS OF USE

CROSS REFERENCE TO RELATED APPLICATIONS

This application is a continuation of U.S. application Ser. No. 15/548,737, filed Aug. 3, 2017, which is a U.S. National Stage filing under 35 U.S.C. § 371 of International Application No. PCT/US2016/016335, filed Feb. 3, 2016, which claims the benefit of U.S. provisional application Ser. No. 62/112,127, filed Feb. 4, 2015, the disclosures of each of which are incorporated herein by reference herein in their entireties.

BACKGROUND

Isocitrate dehydrogenases (IDHs) catalyze the oxidative decarboxylation of isocitrate to 2-oxoglutarate (i.e., α-ketoglutarate). These enzymes belong to two distinct subclasses, one of which utilizes NAD(+) as the electron acceptor and the other NADP(+). Five isocitrate dehydrogenases have been reported: three NAD(+)-dependent isocitrate dehydrogenases, which localize to the mitochondrial matrix, and two NADP(+)-dependent isocitrate dehydrogenases, one of which is mitochondrial and the other predominantly cytosolic. Each NADP(+)-dependent isozyme is a homodimer.

IDH2 (isocitrate dehydrogenase 2 (NADP+), mitochondrial) is also known as IDH; IDP; IDHM; IDPM; ICD-M; or mNADP-IDH. The protein encoded by this gene is the NADP(+)-dependent isocitrate dehydrogenase found in the mitochondria. It plays a role in intermediary metabolism and energy production. This protein may tightly associate or interact with the pyruvate dehydrogenase complex. Human IDH2 gene encodes a protein of 452 amino acids. The nucleotide and amino acid sequences for IDH2 can be found as GenBank entries NM_002168.2 and NP_002159.2 respectively. The nucleotide and amino acid sequence for human IDH2 are also described in, e.g., Huh et al., Submitted (November-1992) to the EMBL/GenBank/DDBJ databases; and The MGC Project Team, Genome Res. 14:2121-2127(2004).

Non-mutant, e.g., wild type, IDH2 catalyzes the oxidative decarboxylation of isocitrate to α-ketoglutarate (α-KG) thereby reducing NAD$^+$ (NADP$^+$) to NADH (NADPH), e.g., in the forward reaction:

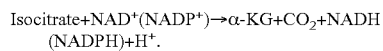

It has been discovered that mutations of IDH2 present in certain cancer cells result in a new ability of the enzyme to catalyze the NAPH-dependent reduction of α-ketoglutarate to R(−)-2-hydroxyglutarate (2-HG). 2-HG is not formed by wild-type IDH2. The production of 2-HG is believed to contribute to the formation and progression of cancer (Dang, L et al, Nature 2009, 462:739-44).

The inhibition of mutant IDH2 and its neoactivity is therefore a potential therapeutic treatment for cancer. Accordingly, there is an ongoing need for inhibitors of IDH2 mutants having alpha hydroxyl neoactivity.

A primary concern for the manufacture of large-scale pharmaceutical compositions is that the active ingredient should have a stable crystalline morphology to ensure consistent processing parameters and pharmaceutical quality. The active ingredient must possess acceptable properties with respect to hygroscopicity, solubility, and stability, which can be consistently reproduced despite the impact of various environmental conditions such as temperature and humidity. If an unstable crystalline form is used, crystal morphology may change during manufacture and/or storage resulting in quality control problems, and formulation irregularities. Such a change may affect the reproducibility of the manufacturing process and thus lead to pharmaceutical formulations that do not meet the high quality and stringent requirements imposed on formulations of pharmaceutical compositions.

When a compound crystallizes from a solution or slurry, it may crystallize with different spatial lattice arrangements, a property referred to as "polymorphism." Each of the crystal forms is a "polymorph." While polymorphs of a given substance have the same chemical composition, they may differ from each other with respect to one or more physical properties, such as solubility and dissociation, true density, melting point, crystal shape, compaction behavior, flow properties, and/or solid state stability.

The polymorphic behavior of pharmaceutically active substances is of great importance in pharmacy and pharmacology. The differences in physical properties exhibited by polymorphs affect practical parameters such as storage stability, compressibility and density (important in pharmaceutical composition manufacturing), and dissolution rates (an important factor in determining bio-availability of an active ingredient). Differences in stability can result from changes in chemical reactivity (e.g., differential oxidation, such that a dosage form discolors more rapidly when it is one polymorph than when it is another polymorph) or mechanical changes (e.g., tablets crumble on storage as a kinetically favored polymorph converts to thermodynamically more stable polymorph) or both (e.g., tablets of one polymorph are more susceptible to breakdown at high humidity than another polymorph). In addition, the physical properties of the crystal may be important in processing: for example, one polymorph might be more likely to form solvates that cause the solid form to aggregate and increase the difficulty of solid handling, or might be difficult to filter and wash free of impurities (i.e., particle shape and size distribution might be different between one polymorph relative to other).

While pharmaceutical formulations having improved chemical and physical properties are desired, there is no predictable means for preparing new crystalline forms (e.g., polymorphs) of existing molecules for such formulations. There is a need for crystalline forms of inhibitors of mutant IDH2 that possess consistent physical properties over the range of environments that may be encountered during pharmaceutical formulation manufacturing and storage. Such crystalline forms would have utility in treating advanced hematologic malignancies, such as acute myelogenous leukemia (AML), myelodysplastic syndrome (MDS), chronic myelomonocytic leukemia (CMML), myeloid sarcoma, multiple myeloma, or lymphoma (e.g., T-cell lymphoma), each characterized by the presence of a mutant allele of IDH2, as well as having properties suitable for large-scale manufacturing and formulation.

PCT Publication No. WO 2013/102431 and US Publication No. US 2013/0190287 hereby incorporated by reference in their entirety, disclose compounds that inhibit IDH2 mutants (e.g., IDH2R140Q and IDH2R172K). These applications additionally disclose methods for the preparation of inhibitors of mutant IDH2, pharmaceutical compositions containing these compounds, and methods for the therapy of diseases, disorders, or conditions (e.g., cancer) associated with overexpression and/or amplification of mutant IDH2.

SUMMARY OF INVENTION

Disclosed herein are methods of treating advanced hematologic malignancies, such as acute myelogenous leukemia (AML), myelodysplastic syndrome (MDS), chronic myelomonocytic leukemia (CMML), myeloid sarcoma, multiple myeloma, or lymphoma (e.g., T-cell lymphoma or B-cell lymphoma), each characterized by the presence of a mutant allele of IDH2.

BRIEF DESCRIPTION OF THE DRAWINGS

FIG. 1 is an X-ray powder diffractogram (XRPD) of compound 3 Form 1.

FIG. 2 is an X-ray powder diffractogram (XRPD) of compound 3 Form 2.

FIG. 3 is a differential scanning calorimetry (DSC) profile of compound 3 Form 2.

FIG. 4 is a thermal gravimetric analysis (TGA) profile of compound 3 Form 2.

FIG. 5 is an X-ray powder diffractogram (XRPD) of compound 1 Form 3.

FIG. 6 is a differential scanning calorimetry (DSC) profile of compound 1 Form 3.

FIG. 7 is a thermal gravimetric analysis (TGA) profile of compound 1 Form 3.

FIG. 8 is a dynamic vapor sorption (DVS) profile of compound 1 Form 3.

FIG. 9 is an X-ray powder diffractogram (XRPD) of compound 1 Form 4.

FIG. 10 is a differential scanning calorimetry (DSC) and thermal gravimetric analysis (TGA) profile of compound 1 Form 4.

FIG. 11 is an X-ray powder diffractogram (XRPD) of compound 1 Form 5.

FIG. 12 is a differential scanning calorimetry (DSC) and thermal gravimetric analysis (TGA) profile of compound 1 Form 5.

FIG. 13 is an X-ray powder diffractogram (XRPD) of compound 1 Form 6.

FIG. 14 is a differential scanning calorimetry (DSC) and thermal gravimetric analysis (TGA) profile of compound 1 Form 6.

FIG. 15 is an X-ray powder diffractogram (XRPD) of compound 1 Form 7.

FIG. 16 is a differential scanning calorimetry (DSC) and thermal gravimetric analysis (TGA) profile of compound 1 Form 7.

FIG. 17 is a X-ray powder diffractogram (XRPD) of compound 1 Form 8.

FIG. 18 is a differential scanning calorimetry (DSC) and thermal gravimetric analysis (TGA) profile of compound 1 Form 8.

FIG. 19 is an X-ray powder diffractogram (XRPD) of compound 1 Form 9.

FIG. 20 is a differential scanning calorimetry (DSC) and thermal gravimetric analysis (TGA) profile of compound 1 Form 9.

FIG. 21 is an X-ray powder diffractogram (XRPD) of compound 1 Form 10.

FIG. 22 is a differential scanning calorimetry (DSC) and thermal gravimetric analysis (TGA) profile of compound 1 Form 10.

FIG. 23 is an X-ray powder diffractogram (XRPD) of compound 1 Form 11.

FIG. 24 is a differential scanning calorimetry (DSC) profile of compound 1 Form 11.

FIG. 25 is a thermal gravimetric analysis (TGA) profile of compound 1 Form 11.

FIG. 26 is an X-ray powder diffractogram (XRPD) of compound 1 Form 12.

FIG. 27 is a differential scanning calorimetry (DSC) and thermal gravimetric analysis (TGA) profile of compound 1 Form 12.

FIG. 28 is a X-ray powder diffractogram (XRPD) of compound 1 Form 13.

FIG. 29 is a differential scanning calorimetry (DSC) and thermal gravimetric analysis (TGA) profile of compound 1 Form 13.

FIG. 30 is an X-ray powder diffractogram (XRPD) of compound 1 Form 14.

FIG. 31 is a differential scanning calorimetry (DSC) and thermal gravimetric analysis (TGA) profile of compound 1 Form 14.

FIG. 32 is an X-ray powder diffractogram (XRPD) of compound 1 Form 15.

FIG. 33 is a differential scanning calorimetry (DSC) and thermal gravimetric analysis (TGA) profile of compound 1 Form 15.

FIG. 34 is an X-ray powder diffractogram (XRPD) of compound 3 Form 16.

FIG. 35 is a differential scanning calorimetry (DSC) profile of compound 3 Form 16.

FIG. 36 is a thermal gravimetric analysis (TGA) profile of compound 3 Form 16.

FIG. 37 is an X-ray powder diffractogram (XRPD) of compound 3 Form 17.

FIG. 38 is an X-ray powder diffractogram (XRPD) of compound 3 Form 18.

FIG. 39 is an X-ray powder diffractogram (XRPD) of compound 3 Form 19.

FIG. 40 is an X-ray powder diffractogram (XRPD) of compound 1 Form 20.

FIG. 41 is a thermal gravimetric analysis (TGA) of compound 1 Form 20.

FIG. 42 is a dynamic vapor sorption (DVS) profile of compound 1 Form 20.

FIG. 43 is an X-ray powder diffractogram (XRPD) of compound 1 Form 21.

FIG. 44 is a thermal gravimetric analysis (TGA) profile of compound 1 Form 21.

FIG. 45 is a differential scanning calorimetry (DSC) profile of compound 1 Form 21.

FIG. 46 is a dynamic vapor sorption (DVS) profile of compound 1 Form 21.

DETAILED DESCRIPTION OF THE INVENTION

The details of construction and the arrangement of components set forth in the following description or illustrated in the drawings are not meant to be limiting. Other embodiments and different ways to practice the invention are expressly included. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

Definitions:

As used above, and throughout the description of the invention, the following terms, unless otherwise indicated, shall be understood to have the following meanings.

As used herein, the term "elevated levels of 2-HG" means 10%, 20% 30%, 50%, 75%, 100%, 200%, 500% or more 2-HG then is present in a subject that does not carry a mutant IDH allele (e.g., a mutant IDH2 allele). The term "elevated levels of 2-HG" may refer to the amount of 2-HG within a cell, within a tumor, within an organ comprising a tumor, or within a bodily fluid.

The term "bodily fluid" includes one or more of amniotic fluid surrounding a fetus, aqueous humour, blood (e.g., blood plasma), serum, Cerebrospinal fluid, cerumen, chyme, Cowper's fluid, female ejaculate, interstitial fluid, lymph, breast milk, mucus (e.g., nasal drainage or phlegm), pleural fluid, pus, saliva, sebum, semen, serum, sweat, tears, urine, vaginal secretion, or vomit.

As used herein, the terms "inhibit" or "prevent" include both complete and partial inhibition and prevention. An inhibitor may completely or partially inhibit the intended target.

The term an "mutant IDH2 inhibitor" or "inhibitor of IDH2 mutant(s)" means a molecule e.g., a polypeptide, peptide, or small molecule (e.g., a molecule of less than 1,000 daltons), or aptomer, that binds to an IDH2 mutant subunit and inhibits neoactivity, e.g., by inhibiting formation of a dimer, e.g., a homodimer of mutant IDH2 subunits or a heterodimer of a mutant and a wildype subunit. In some embodiments, the neoactivity inhibition is at least about 60%, 70%, 80%, 90%, 95% or 99%.

The term "treat" means decrease, suppress, attenuate, diminish, arrest, or stabilize the development or progression of a disease/disorder (e.g., an advanced hematologic malignancy, such as acute myelogenous leukemia (AML), myelodysplastic syndrome (MDS), chronic myelomonocytic leukemia (CMML), myeloid sarcoma, multiple myeloma, or lymphoma (e.g., T-cell lymphoma), each characterized by the presence of a mutant allele of IDH2), lessen the severity of the disease/disorder or improve the symptoms associated with the disease/disorder.

As used herein, an amount of a compound, including a crystalline form thereof, effective to treat a disorder, or a "therapeutically effective amount" or "therapeutically effective dose" refers to an amount of the compound, or a pharmaceutically acceptable salt thereof, including a crystalline form thereof, which is effective, upon single or multiple dose administration to a subject, in treating a cell, or in curing, alleviating, relieving or improving a subject with a disorder beyond that expected in the absence of such treatment.

As used herein, the term "subject" is intended to mean human. Exemplary human subjects include a human patient (referred to as a patient) having a disorder, e.g., a disorder described herein or a normal subject.

"Free-base equivalent" or "free-base equivalent strength" is the amount of compound 1 or another pharmaceutically acceptable salt of compound 3 that is equivalent to the free-base compound 3 dose. For example 30 mg (free-base equivalent strength) would equal 36 mg of compound 1, 50 mg (free-base equivalent strength) would equal 60 mg of compound 1, 75 mg (free-base equivalent strength) would equal 90 mg, 100 mg (free-base equivalent strength) would equal 120 mg, and 125 mg (free-base equivalent strength) would equal 150 mg.

"Form 1" or "compound 3 Form 1" are used interchangeably, and describe Form 1 of compound 3, as synthesized in Example 3A, in the Examples section below, and as described below, and represented by data shown in FIG. 1.

"Form 2" or "compound 3 Form 2" are used interchangeably, and describe Form 2 of compound 3, as synthesized in Example 4A, in the Examples section below, and as described below, and represented by data shown in FIGS. 2, 3, and 4.

"Form 3" or "compound 1 Form 3" are used interchangeably, and describe Form 3 of compound 1, as synthesized in Example 6A, in the Examples section below, and as described below, and represented by data shown in FIGS. 5, 6, 7, and 8.

"Form 4" or "compound 1 Form 4" are used interchangeably, and describe Form 4 of compound 1, as synthesized in Example 7A, in the Examples section below, and as described below, and represented by data shown in FIGS. 9 and 10.

"Form 5" or "compound 1 Form 5" are used interchangeably, and describe Form 5 of compound 1, as synthesized in Example 8A, in the Examples section below, and as described below, and represented by data shown in FIGS. 11 and 12.

"Form 6" or "compound 1 Form 6" are used interchangeably, and describe Form 6 of compound 1, as synthesized in Example 9A, in the Examples section below, and as described below, and represented by data shown in FIGS. 13 and 14.

"Form 7" or "compound 1 Form 7" are used interchangeably, and describe Form 7 of compound 1, as synthesized in Example 10A, in the Examples section below, and as described below, and represented by data shown in FIGS. 15 and 16.

"Form 8" or "compound 1 Form 8" are used interchangeably, and describe Form 8 of compound 1, as synthesized in Example 11A, in the Examples section below, and as described below, and represented by data shown in FIGS. 17 and 18.

"Form 9" or "compound 1 Form 9" are used interchangeably, and describe Form 9 of compound 1, as synthesized in Example 12A, in the Examples section below, and as described below, and represented by data shown in FIGS. 19 and 20.

"Form 10" or "compound 1 Form 10" are used interchangeably, and describe Form 10 of compound 1, as synthesized in Example 13A, in the Examples section below, and as described below, and represented by data shown in FIGS. 21 and 22.

"Form 11" or "compound 1 Form 11" are used interchangeably, and describe Form 11 of compound 1, as synthesized in Example 14A, in the Examples section below, and as described below, and represented by data shown in FIGS. 23, 24, and 25.

"Form 12" or "compound 1 Form 12" are used interchangeably, and describe Form 12 of compound 1, as synthesized in Example 15A, in the Examples section below, and as described below, and represented by data shown in FIGS. 26 and 27.

"Form 13" or "compound 1 Form 13" are used interchangeably, and describe Form 13 of compound 1, as synthesized in Example 16A, in the Examples section below, and as described below, and represented by data shown in FIGS. 28 and 29.

"Form 14" or "compound 1 Form 14" are used interchangeably, and describe Form 14 of compound 1, as synthesized in Example 17A, in the Examples section below, and as described below, and represented by data shown in FIGS. 30 and 31.

"Form 15" or "compound 1 Form 15" are used interchangeably, and describe Form 15 of compound 1, as synthesized in Example 18A, in the Examples section below, and as described below, and represented by data shown in FIGS. 32 and 33.

"Form 16" or "compound 3 Form 16" are used interchangeably, and describe Form 16 of compound 3, as synthesized in Example 2A, in the Examples section below, and as described below, and represented by data shown in FIGS. 34, 35 and 36.

"Form 17" or "compound 3 Form 16" are used interchangeably, and describe Form 16 of compound 3, as synthesized in Example 20A, in the Examples section below, and as described below, and represented by data shown in FIG. 37.

"Form 18" or "compound 3 Form 16" are used interchangeably, and describe Form 16 of compound 3, as synthesized in Example 21A, in the Examples section below, and as described below, and represented by data shown in FIG. 38.

"Form 19" or "compound 3 Form 16" are used interchangeably, and describe Form 16 of compound 3, as synthesized in Example 22A, in the Examples section below, and as described below, and represented by data shown in FIG. 39.

"Form 20" or "compound 1 Form 20" are used interchangeably, and describe Form 20 of compound 1, as synthesized in Example 23A, in the Examples section below, and as described below, and represented by data shown in FIG. 40.

"Form 21" or "compound 1 Form 21" are used interchangeably, and describe Form 21 of compound 1, as synthesized in Example 24A, in the Examples section below, and as described below, and represented by data shown in FIG. 43.

As used herein, "crystalline" refers to a solid having a highly regular chemical structure. In particular, a crystalline compound 3 or compound 1 may be produced as one or more single crystalline forms of the compound 3 or compound 1. For the purposes of this application, the terms "crystalline form", "single crystalline form" and "polymorph" are synonymous; the terms distinguish between crystals that have different properties (e.g., different XRPD patterns and/or different DSC scan results). The term "polymorph" includes pseudopolymorphs, which are typically different solvates of a material, and thus their properties differ from one another. Thus, each distinct polymorph and pseudopolymorph of the compound 3 or compound 1 is considered to be a distinct single crystalline form herein.

"Substantially crystalline" refers to forms that may be at least a particular weight percent crystalline. Particular weight percentages are 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5%, 99.9%, or any percentage between 10% and 100%. In some embodiments, substantially crystalline refers to a compound 3 or compound 1 that is at least 70% crystalline. In other embodiments, substantially crystalline refers to a compound 3 or compound 1 that is at least 90% crystalline.

As used herein, the terms "isolated" refers to forms that may be at least a particular weight percent of a particular crystalline form of compound 1 or compound 3. Particular weight percentages are 90%, 91%, 92%, 93%, 94%, 95%, 96%, 97%, 98%, 99%, 99.5%, 99.9%, or any percentage between 90% and 100%.

The term "solvate or solvated" means a physical association of a compound, including a crystalline form thereof, of this invention with one or more solvent molecules. This physical association includes hydrogen bonding. In certain instances the solvate will be capable of isolation, for example when one or more solvent molecules are incorporated in the crystal lattice of the crystalline solid. "Solvate or solvated" encompasses both solution-phase and isolable solvates. Representative solvates include, for example, a hydrate, ethanolates or a methanolate.

The term "hydrate" is a solvate wherein the solvent molecule is $H_2O$ that is present in a defined stoichiometric amount, and may, for example, include hemihydrate, monohydrate, dihydrate, or trihydrate.

The term "mixture" is used to refer to the combined elements of the mixture regardless of the phase-state of the combination (e.g., liquid or liquid/ crystalline).

The term "seeding" is used to refer to the addition of a crystalline material to initiate recrystallization or crystallization.

The term "antisolvent" is used to refer to a solvent in which compounds, including crystalline forms thereof, are poorly soluble.

As used herein, the term "about" means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

Pharmaceutical Compositions and Methods of Treatment

Provided is a method of treating advanced hematologic malignancies, such as acute myelogenous leukemia (AML), myelodysplastic syndrome (MDS), chronic myelomonocytic leukemia (CMML), myeloid sarcoma, multiple myeloma, or lymphoma (e.g., T-cell lymphoma or B-cell lymphoma), each characterized by the presence of a mutant allele of IDH2, comprising administering to subject in need thereof a therapeutically effective amount of a mutant IDH2 inhibitor.

Also provided is a method of treating advanced hematologic malignancies, such as acute myelogenous leukemia (AML), myelodysplastic syndrome (MDS), chronic myelomonocytic leukemia (CMML), or lymphoma (e.g., T-cell lymphoma), each characterized by the presence of a mutant allele of IDH2, comprising administering to subject in need thereof a therapeutically effective amount of a mutant IDH2 inhibitor.

Also provided is a method of treating an advanced hematologic malignancy selected from acute myelogenous leukemia (AML), myelodysplastic syndrome (MDS), chronic myelomonocytic leukemia (CMML), myeloid sarcoma, multiple myeloma, and lymphoma (e.g., T-cell lymphoma or B-cell lymphoma), each characterized by the presence of a mutant allele of IDH2, comprising administering to a subject in need thereof a therapeutically effective amount of compound 3, or a pharmaceutically acceptable salt thereof.

Also provided is a method of treating advanced hematologic malignancies, such as acute myelogenous leukemia (AML), myelodysplastic syndrome (MDS), chronic myelomonocytic leukemia (CMML), myeloid sarcoma, multiple myeloma, or lymphoma (e.g., T-cell lymphoma or B-cell lymphoma), each characterized by the presence of a mutant allele of IDH2, comprising administering to subject in need thereof a therapeutically effective amount of compound 1.

Also provided is a method of treating advanced hematologic malignancies, such as acute myelogenous leukemia (AML), myelodysplastic syndrome (MDS), chronic myelomonocytic leukemia (CMML), myeloid sarcoma, multiple myeloma, or lymphoma (e.g., T-cell lymphoma), each characterized by the presence of a mutant allele of IDH2, comprising administering to subject in need thereof a therapeutically effective amount of 2-Methyl-1-[(4-[6-(trifluoromethyl)pyridin-2-yl]-6-{[2-(trifluoromethyl)pyridin-4-yl]amino}-1,3,5-triazin-2-yl)amino]propan-2-ol mesylate (compound 1).

Also provided is a method of treating advanced hematologic malignancies, such as acute myelogenous leukemia (AML), myelodysplastic syndrome (MDS), chronic myelomonocytic leukemia (CMML), myeloid sarcoma, multiple myeloma, or lymphoma (e.g., T-cell lymphoma or B-cell lymphoma), each characterized by the presence of a mutant allele of IDH2, comprising administering to subject in need thereof a pharmaceutical composition comprising a therapeutically effective amount of a mutant IDH2 inhibitor, and one or more pharmaceutically acceptable carrier(s).

Also provided is a method of treating an advanced hematologic malignancy selected from acute myelogenous leukemia (AML), myelodysplastic syndrome (MDS), chronic myelomonocytic leukemia (CMML), myeloid sarcoma, multiple myeloma, and lymphoma (e.g., T-cell lymphoma or B-cell lymphoma), each characterized by the presence of a mutant allele of IDH2, comprising administering to subject in need thereof a pharmaceutical composition comprising a therapeutically effective amount of compound 3, or a pharmaceutically acceptable salt thereof, and one or more pharmaceutically acceptable carrier(s).

Also provided is a method of treating advanced hematologic malignancies, such as acute myelogenous leukemia (AML), myelodysplastic syndrome (MDS), chronic myelomonocytic leukemia (CMML), myeloid sarcoma, multiple myeloma, or lymphoma (e.g., T-cell lymphoma or B-cell lymphoma), each characterized by the presence of a mutant allele of IDH2, comprising administering to subject in need thereof a pharmaceutical composition comprising a therapeutically effective amount of compound 1, and one or more pharmaceutically acceptable carrier(s).

Also provided is a method of treating advanced hematologic malignancies, such as acute myelogenous leukemia (AML), myelodysplastic syndrome (MDS), chronic myelomonocytic leukemia (CMML), myeloid sarcoma, multiple myeloma, or lymphoma (e.g., T-cell lymphoma), each characterized by the presence of a mutant allele of IDH2, comprising administering to subject in need thereof a pharmaceutical composition comprising a therapeutically effective amount of compound 1, and one or more pharmaceutically acceptable carrier(s).

Also provided is a method of treating advanced hematologic malignancies, such as acute myelogenous leukemia (AML), myelodysplastic syndrome (MDS), chronic myelomonocytic leukemia (CMML), or lymphoma (e.g., T-cell lymphoma), each characterized by the presence of a mutant allele of IDH2, comprising administering to subject in need thereof a pharmaceutical composition comprising a therapeutically effective amount of compound 1, and one or more pharmaceutically acceptable carrier(s).

Also provided is a method of treating advanced hematologic malignancies, such as acute myelogenous leukemia (AML), myelodysplastic syndrome (MDS), chronic myelomonocytic leukemia (CMML), myeloid sarcoma, multiple myeloma, or lymphoma (e.g., T-cell lymphoma or B-cell lymphoma), each characterized by the presence of a mutant allele of IDH2, comprising administering to subject in need thereof a therapeutically effective amount of compound 1, or a crystalline form thereof; or a therapeutically effective dose of compound 3, or a crystalline form thereof.

Also provided is a method of treating advanced hematologic malignancies, such as acute myelogenous leukemia (AML), myelodysplastic syndrome (MDS), chronic myelomonocytic leukemia (CMML), myeloid sarcoma, multiple myeloma, or lymphoma (e.g., T-cell lymphoma or B-cell lymphoma), each characterized by the presence of a mutant allele of IDH2, comprising administering to subject in need thereof a pharmaceutical composition comprising a therapeutically effective amount of compound 1, or a crystalline form thereof; or a therapeutically effective dose of compound 3, or a crystalline form thereof and one or more pharmaceutically acceptable carrier(s).

Also provided is a method of treating advanced hematologic malignancies, such as acute myelogenous leukemia (AML), myelodysplastic syndrome (MDS), chronic myelomonocytic leukemia (CMML), or lymphoma (e.g., T-cell lymphoma), each characterized by the presence of a mutant allele of IDH2, comprising administering to subject in need thereof a pharmaceutical composition comprising a therapeutically effective amount of compound 1, or a crystalline form thereof; or a therapeutically effective dose of compound 3, or a crystalline form thereof; and one or more pharmaceutically acceptable carrier(s).

Also provided is a method of treating an advanced hematologic malignancy selected from acute myelogenous leukemia (AML), myelodysplastic syndrome (MDS), chronic myelomonocytic leukemia (CMML), myeloid sarcoma, multiple myeloma, and lymphoma (e.g., T-cell lymphoma or B-cell lymphoma), each characterized by the presence of a mutant allele of IDH2, comprising administering to a subject in need thereof a therapeutically effective dose of a pharmaceutically acceptable salt of compound 3, wherein the therapeutically effective dose is from about 30 mg to about 300 mg (free-base equivalent strength), once daily or twice daily (e.g., about 30 mg to about 200 mg once daily or twice daily; or about 30 mg to about 150 mg once daily or twice daily). In one embodiment, the therapeutically effective dose is a free-base equivalent strength of 30 mg, once daily or twice daily. In another embodiment, the therapeutically effective dose is a free-base equivalent strength of 50 mg, once daily or twice daily. In another embodiment, the therapeutically effective dose is a free-base equivalent strength of 75 mg, once daily or twice daily. In another embodiment, the therapeutically effective dose is a free-base equivalent strength of 100 mg, once daily or twice daily. In another embodiment, the therapeutically effective dose is a free-base equivalent strength of 125 mg, once daily or twice daily. In another embodiment, the therapeutically effective dose is a free-base equivalent strength of 150 mg, once daily or twice daily. In another embodiment, the therapeutically effective dose is a free-base equivalent strength of 175 mg, once daily or twice daily. In another embodiment, the therapeutically effective dose is a free-base equivalent strength of 200 mg, once daily or twice daily. In another embodiment, the therapeutically effective dose is a free-base equivalent strength of 225 mg, once daily or twice daily. In another embodiment, the therapeutically effective dose is a free-base equivalent strength of 250 mg, once daily or twice daily. In another embodiment, the therapeutically effective dose is a free-base equivalent strength of 275 mg, once daily or twice daily. In another embodiment, the therapeutically effective dose is a free-base equivalent strength of 300 mg, once daily or twice daily.

In some embodiments, in the methods of the present invention, a pharmaceutically acceptable salt of compound 3 is administered orally as any combination of 5, 10, 50, or 200 mg free-base equivalent strength tablets, twice daily or once daily. In some embodiments, compound 1 is administered orally as any combination of 5, 10, 50, or 200 mg free-base equivalent strength tablets, twice daily or once daily. In some embodiments, a crystalline form of compound 1 is administered orally as any combination of 5, 10, 50, or 200 mg free-base equivalent strength tablets, twice daily or once daily.

In some embodiments, in the methods of the present invention, a pharmaceutically acceptable salt of compound 3 is administered orally as any combination of 5, 10, 50, 100, 150 or 200 mg free-base equivalent strength tablets, twice daily or once daily. In some embodiments, compound 1 is administered orally as any combination of 5, 10, 50, 100, 150 or 200 mg free-base equivalent strength tablets, twice daily or once daily. In some embodiments, a crystalline form of compound 1 is administered orally as any combination of 5, 10, 50, 100, 150 or 200 mg free-base equivalent strength tablets, twice daily or once daily.

Also provided is a method of treating advanced hematologic malignancies, such as acute myelogenous leukemia (AML), myelodysplastic syndrome (MDS), chronic myelomonocytic leukemia (CMML), myeloid sarcoma, multiple myeloma, or lymphoma (e.g., T-cell lymphoma or B-cell lymphoma), each characterized by the presence of a mutant allele of IDH2, comprising administering to a subject in need thereof compound 1 at a dose of at least about 30 mg (free-base equivalent strength) (e.g., in an amount from about 30 mg to about 300 mg; about 30 mg to about 200 mg; or about 30 mg to about 150 mg (free-base equivalent strength)) twice daily.

Also provided is a method of treating advanced hematologic malignancies, such as acute myelogenous leukemia (AML), myelodysplastic syndrome (MDS), chronic myelomonocytic leukemia (CMML), myeloid sarcoma, multiple myeloma, or lymphoma (e.g., T-cell lymphoma), each characterized by the presence of a mutant allele of IDH2, comprising administering to a subject in need thereof compound 1 at a dose of at least about 30 mg (free-base equivalent strength) (e.g., in an amount from about 30 mg to about 300 mg; about 30 mg to about 200 mg; or about 30 mg to about 150 mg (free-base equivalent strength)) twice daily.

In some embodiments, the method of treating advanced hematologic malignancies, such as acute myelogenous leukemia (AML), myelodysplastic syndrome (MDS), chronic myelomonocytic leukemia (CMML), myeloid sarcoma, multiple myeloma, or lymphoma (e.g., T-cell lymphoma or B-cell lymphoma), each characterized by the presence of a mutant allele of IDH2, comprising administering to subject in need thereof compound 1, or a crystalline form thereof; or compound 3, or a crystalline form thereof, at a dose of at least about 30 mg (free-base equivalent strength) (e.g., in an amount from about 30 mg to about 300 mg; about 30 mg to about 200 mg; or about 30 mg to about 150 mg (free-base equivalent strength)) twice daily.

In some embodiments, the method of treating advanced hematologic malignancies, such as acute myelogenous leukemia (AML), myelodysplastic syndrome (MDS), chronic myelomonocytic leukemia (CMML), or lymphoma (e.g., T-cell lymphoma), each characterized by the presence of a mutant allele of IDH2, comprises administering to subject in need thereof compound 1, or a crystalline form thereof; or compound 3, or a crystalline form thereof, at a dose of from about 30 mg to about 300 mg (free-base equivalent strength) (e.g., in an amount from about 30 mg to about 300 mg; about 30 mg to about 200 mg; or about 30 mg to about 150 mg (free-base equivalent strength)) twice daily.

In some embodiments, the second daily administration is provided between about 8 hours and about 16 hours after the first administration.

In one embodiment, the dose is 30 mg (free-base equivalent strength), twice daily. In another embodiment, the dose is 50 mg (free-base equivalent strength), twice daily. In another embodiment, the dose is 75 mg (free-base equivalent strength), twice daily. In another embodiment, the dose is 100 mg (free-base equivalent strength), twice daily. In another embodiment, the dose is 125 mg (free-base equivalent strength), twice daily. In another embodiment, the dose is 150 mg (free-base equivalent strength), twice daily. In another embodiment, the dose is 175 mg (free-base equivalent strength), twice daily. In another embodiment, the dose is 200 mg (free-base equivalent strength), twice daily. In another embodiment, the dose is 225 mg (free-base equivalent strength), twice daily. In another embodiment, the dose is 250 mg (free-base equivalent strength), twice daily.

In some embodiments, the method of treating advanced hematologic malignancies, such as acute myelogenous leukemia (AML), myelodysplastic syndrome (MDS), or chronic myelomonocytic leukemia (CMML), each characterized by the presence of a mutant allele of IDH2, comprises administering to subject in need thereof compound 1, or a crystalline form thereof; or compound 3, or a crystalline form thereof, at a dose of from about 75 mg to about 150 mg (free-base equivalent strength) twice daily.

In one embodiment, the method is a method of treating AML characterized by the presence of a mutant allele of IDH2 comprises administering to subject in need thereof compound 1, or a crystalline form thereof; or compound 3, or a crystalline form thereof at a dose of from about 75 mg to about 150 mg (free-base equivalent strength) twice daily.

In one embodiment, the method is a method of treating AML characterized by the presence of a mutant allele of IDH2 comprises administering to subject in need thereof compound 1, or a crystalline form thereof, in the oral dosage form of a tablet, at a dose of from about 75 mg to about 150 mg (free-base equivalent strength), twice daily.

In one embodiment, the method is a method of treating MDS characterized by the presence of a mutant allele of IDH2 comprises administering to subject in need thereof compound 1, or a crystalline form thereof; or compound 3, or a crystalline form thereof at a dose of from about 75 mg to about 150 mg (free-base equivalent strength), twice daily.

In one embodiment, the method is a method of treating MDS characterized by the presence of a mutant allele of IDH2 comprises administering to subject in need thereof compound 1, or a crystalline form thereof; or compound 3, or a crystalline form thereof, in the oral dosage form of a tablet, at a dose of from about 75 mg to about 150 mg (free-base equivalent strength), twice daily.

In one embodiment, the method is a method of treating CMML characterized by the presence of a mutant allele of IDH2 comprises administering to subject in need thereof compound 1, or a crystalline form thereof; or compound 3, or a crystalline form thereof at a dose of from about 75 mg to about 150 mg (free-base equivalent strength), twice daily.

In one embodiment, the method is a method of treating CMML characterized by the presence of a mutant allele of IDH2 comprises administering to subject in need thereof compound 1, or a crystalline form thereof; or compound 3, or a crystalline form thereof, in the oral dosage form of a tablet, at a dose of from about 75 mg to about 150 mg (free-base equivalent strength), twice daily.

In one embodiment, the method is a method of treating myeloid sarcoma characterized by the presence of a mutant allele of IDH2 comprises administering to subject in need thereof compound 1, or a crystalline form thereof; or compound 3, or a crystalline form thereof at a dose of from about 75 mg to about 150 mg (free-base equivalent strength), twice daily.

In one embodiment, the method is a method of treating myeloid sarcoma characterized by the presence of a mutant allele of IDH2 comprises administering to subject in need thereof compound 1, or a crystalline form thereof; or compound 3, or a crystalline form thereof, in the oral dosage form of a tablet, at a dose of from about 75 mg to about 150 mg (free-base equivalent strength), twice daily.

In one embodiment, the method is a method of treating multiple myeloma characterized by the presence of a mutant allele of IDH2 comprises administering to subject in need thereof compound 1, or a crystalline form thereof; or compound 3, or a crystalline form thereof at a dose of from about 75 mg to about 150 mg (free-base equivalent strength), twice daily.

In one embodiment, the method is a method of treating multiple myeloma characterized by the presence of a mutant allele of IDH2 comprises administering to subject in need thereof compound 1, or a crystalline form thereof; or compound 3, or a crystalline form thereof, in the oral dosage form of a tablet, at a dose of from about 75 mg to about 150 mg (free-base equivalent strength), twice daily.

In one embodiment, the method is a method of treating lymphoma characterized by the presence of a mutant allele of IDH2 comprises administering to subject in need thereof compound 1, or a crystalline form thereof; or compound 3, or a crystalline form thereof at a dose of from about 75 mg to about 150 mg (free-base equivalent strength), twice daily.

In one embodiment, the method is a method of treating lymphoma characterized by the presence of a mutant allele of IDH2 comprises administering to subject in need thereof compound 1, or a crystalline form thereof; or compound 3, or a crystalline form thereof, in the oral dosage form of a tablet, at a dose of from about 75 mg to about 150 mg (free-base equivalent strength), twice daily.

In one embodiment, the method is a method of treating T-cell lymphoma characterized by the presence of a mutant allele of IDH2 comprises administering to subject in need thereof compound 1, or a crystalline form thereof; or compound 3, or a crystalline form thereof at a dose of from about 75 mg to about 150 mg (free-base equivalent strength), twice daily.

In one embodiment, the method is a method of treating T-cell lymphoma characterized by the presence of a mutant allele of IDH2 comprises administering to subject in need thereof compound 1, or a crystalline form thereof; or compound 3, or a crystalline form thereof, in the oral dosage form of a tablet, at a dose of from about 75 mg to about 150 mg (free-base equivalent strength), twice daily.

In one embodiment, the method is a method of treating B-cell lymphoma characterized by the presence of a mutant allele of IDH2 comprises administering to subject in need thereof compound 1, or a crystalline form thereof; or compound 3, or a crystalline form thereof at a dose of from about 75 mg to about 150 mg (free-base equivalent strength), twice daily.

In one embodiment, the method is a method of treating B-cell lymphoma characterized by the presence of a mutant allele of IDH2 comprises administering to subject in need thereof compound 1, or a crystalline form thereof; or compound 3, or a crystalline form thereof, in the oral dosage form of a tablet, at a dose of from about 75 mg to about 150 mg (free-base equivalent strength), twice daily.

In some embodiments, the second daily administration is provided between about 10 hours and about 14 hours after the first daily administration.

In some embodiments, the methods described herein include oral administration of compound 1, or a crystalline form thereof; or compound 3, or a crystalline form thereof to a subject at a dose of about 30 mg, about 50 mg, about 75 mg, about 100 mg, 125 mg, about 150 mg, about 175 mg, about 200 mg, about 225 mg, or about 250 mg (each of which is the free-base equivalent strength) twice a day. In one embodiment, the second daily dose is given 4, 5, 6, 7, 8, 9, 10, 11, 12, 13, 14, 15, 16, 17, 18, 19, 20 hours after the initial daily dose.

In some embodiments, the method of treating advanced hematologic malignancies, such as acute myelogenous leukemia (AML), myelodysplastic syndrome (MDS), chronic myelomonocytic leukemia (CMML), myeloid sarcoma, multiple myeloma, or lymphoma (e.g., T-cell lymphoma or B-cell lymphoma), each characterized by the presence of a mutant allele of IDH2, comprises administering to subject in need thereof compound 1 at a dose of from about 75 mg to about 300 mg (free-base equivalent strength), once daily (e.g., about 75 mg to about 200 mg (free-base equivalent strength), once daily).

In some embodiments, the method of treating advanced hematologic malignancies, such as acute myelogenous leukemia (AML), myelodysplastic syndrome (MDS), chronic myelomonocytic leukemia (CMML), myeloid sarcoma, multiple myeloma, or lymphoma (e.g., T-cell lymphoma), each characterized by the presence of a mutant allele of IDH2, comprises administering to subject in need thereof compound 1, or a crystalline form thereof; or compound 3, or a crystalline form thereof, at a dose of from about 75 mg to about 3000 mg (free-base equivalent strength), once daily (e.g., about 75 mg to about 200 mg (free-base equivalent strength), once daily).

In some embodiments, the method of treating advanced hematologic malignancies, such as acute myelogenous leukemia (AML), myelodysplastic syndrome (MDS), chronic myelomonocytic leukemia (CMML), or lymphoma (e.g., T-cell lymphoma), each characterized by the presence of a mutant allele of IDH2, comprises administering to subject in need thereof compound 1, or a crystalline form thereof; or compound 3, or a crystalline form thereof at a dose of from about 75 mg to about 300 mg (free-base equivalent strength), once daily (e.g., about 75 mg to about 200 mg (free-base equivalent strength), once daily).

In one embodiment, the dose is 100 mg (free-base equivalent strength), once daily. In one embodiment, the dose is 150 mg (free-base equivalent strength), once daily. In one embodiment, the dose is 175 mg (free-base equivalent strength), once daily. In one embodiment, the dose is 200 mg (free-base equivalent strength), once daily. In one embodiment, the dose is 225 mg (free-base equivalent strength), once daily. In one embodiment, the dose is 250 mg (free-base equivalent strength), once daily. In one embodiment, the dose is 275 mg (free-base equivalent strength), once daily.

In some embodiments, the method of treating advanced hematologic malignancies, such as acute myelogenous leukemia (AML), myelodysplastic syndrome (MDS), or chronic myelomonocytic leukemia (CMML), each characterized by the presence of a mutant allele of IDH2, comprises administering to subject in need thereof compound 1, or a crystalline form thereof; or compound 3, or a crystalline form thereof at a dose of from about 150 mg to about 300 mg (free-base equivalent strength), once daily (e.g., about 150 mg to about 200 mg (free-base equivalent strength), once daily).

In one embodiment, the method is a method of treating AML characterized by the presence of a mutant allele of IDH2 comprises administering to subject in need thereof compound 1, or a crystalline form thereof; or compound 3, or a crystalline form thereof at a dose of from about 100 mg to about 300 mg (free-base equivalent strength), once daily (e.g., about 150 mg to about 200 mg (free-base equivalent strength), once daily).

In one embodiment, the method is a method of treating AML characterized by the presence of a mutant allele of IDH2 comprises administering to subject in need thereof compound 1, or a crystalline form thereof, in the oral dosage form of a tablet, at a dose of from about 150 mg to about 300 mg (free-base equivalent strength) once daily.

In one embodiment, the method is a method of treating MDS characterized by the presence of a mutant allele of IDH2 comprises administering to subject in need thereof compound 1, or a crystalline form thereof; or compound 3, or a crystalline form thereof at a dose of from about 100 mg to about 300 mg (free-base equivalent strength) once daily.

In one embodiment, the method is a method of treating MDS characterized by the presence of a mutant allele of IDH2 comprises administering to subject in need thereof compound 1, or a crystalline form thereof; or compound 3, or a crystalline form thereof, in the oral dosage form of a tablet, at a dose of from about 150 mg to about 300 mg (free-base equivalent strength) once daily.

In one embodiment, the method is a method of treating CMML characterized by the presence of a mutant allele of IDH2 comprises administering to subject in need thereof compound 1, or a crystalline form thereof; or compound 3, or a crystalline form thereof at a dose of from about 100 mg to about 300 mg (free-base equivalent strength) once daily.

In one embodiment, the method is a method of treating CMML characterized by the presence of a mutant allele of IDH2 comprises administering to subject in need thereof compound 1, or a crystalline form thereof; or compound 3, or a crystalline form thereof, in the oral dosage form of a tablet, at a dose of from about 150 mg to about 300 mg (free-base equivalent strength) once daily.

In one embodiment, the method is a method of treating myeloid sarcoma characterized by the presence of a mutant allele of IDH2 comprises administering to subject in need thereof compound 1, or a crystalline form thereof; or compound 3, or a crystalline form thereof at a dose of from about 100 mg to about 300 mg (free-base equivalent strength) once daily.

In one embodiment, the method is a method of treating myeloid sarcoma characterized by the presence of a mutant allele of IDH2 comprises administering to subject in need thereof compound 1, or a crystalline form thereof; or compound 3, or a crystalline form thereof, in the oral dosage form of a tablet, at a dose of from about 150 mg to about 300 mg (free-base equivalent strength) once daily.

In one embodiment, the method is a method of treating multiple myeloma characterized by the presence of a mutant allele of IDH2 comprises administering to subject in need thereof compound 1, or a crystalline form thereof; or compound 3, or a crystalline form thereof at a dose of from about 100 mg to about 300 mg (free-base equivalent strength) once daily.

In one embodiment, the method is a method of treating multiple myeloma characterized by the presence of a mutant allele of IDH2 comprises administering to subject in need thereof compound 1, or a crystalline form thereof; or compound 3, or a crystalline form thereof, in the oral dosage form of a tablet, at a dose of from about 150 mg to about 300 mg (free-base equivalent strength) once daily.

In one embodiment, the method is a method of treating lymphoma characterized by the presence of a mutant allele of IDH2 comprises administering to subject in need thereof compound 1, or a crystalline form thereof; or compound 3, or a crystalline form thereof at a dose of from about 100 mg to about 300 mg (free-base equivalent strength) once daily.

In one embodiment, the method is a method of treating lymphoma characterized by the presence of a mutant allele of IDH2 comprises administering to subject in need thereof compound 1, or a crystalline form thereof; or compound 3, or a crystalline form thereof, in the oral dosage form of a tablet, at a dose of from about 150 mg to about 300 mg (free-base equivalent strength) once daily.

In one embodiment, the method is a method of treating T-cell lymphoma characterized by the presence of a mutant allele of IDH2 comprises administering to subject in need thereof compound 1, or a crystalline form thereof; or compound 3, or a crystalline form thereof at a dose of from about 100 mg to about 300 mg (free-base equivalent strength) once daily.

In one embodiment, the method is a method of treating T-cell lymphoma characterized by the presence of a mutant allele of IDH2 comprises administering to subject in need thereof compound 1, or a crystalline form thereof; or compound 3, or a crystalline form thereof, in the oral dosage form of a tablet, at a dose of from about 150 mg to about 300 mg (free-base equivalent strength) once daily.

In one embodiment, the method is a method of treating B-cell lymphoma characterized by the presence of a mutant allele of IDH2 comprises administering to subject in need thereof compound 1, or a crystalline form thereof; or compound 3, or a crystalline form thereof at a dose of from about 100 mg to about 300 mg (free-base equivalent strength) once daily.

In one embodiment, the method is a method of treating B-cell lymphoma characterized by the presence of a mutant allele of IDH2 comprises administering to subject in need thereof compound 1, or a crystalline form thereof; or compound 3, or a crystalline form thereof, in the oral dosage form of a tablet, at a dose of from about 150 mg to about 300 mg (free-base equivalent strength) once daily.

In some embodiments, the method includes oral administration of compound 1, or a crystalline form thereof; or compound 3, or a crystalline form thereof to a subject at a dose of about 75, about 100 mg, about 125 mg, about 150 mg, about 175 mg, about 200 mg, about 225 mg, about 250 mg, about 275 mg, or about 300 mg (each of which is the free-base equivalent strength) once daily.

It will be understood that a therapeutically effective dose of compound 1, or a crystalline form thereof; or a therapeutically effective dose of compound 3, or a crystalline form thereof, may be taken at any time of the day or night. In some embodiments, a therapeutically effective dose of compound 1 is taken in the morning. In other embodiments, a therapeutically effective dose of compound 1, or a crystalline form thereof; or a therapeutically effective dose of compound 3, or a crystalline form thereof is taken in the evening. It will be understood that a therapeutically effective dose of compound 1, or a crystalline form thereof; or a therapeutically effective dose of compound 3, or a crystalline form thereof may be taken with or without food. In some embodiments, a therapeutically effective dose of compound 1, or a crystalline form thereof; or a therapeutically effective dose of compound 3, or a crystalline form thereof, is taken with a meal (e.g., administration of single oral dose 30 minutes after the start of a high-fat meal [high-fat Food and Drug Administration standard meal: for example, 2 extra-large eggs cooked in butter, 2 pieces cured, cooked bacon, 2 pieces enriched white bread with butter, 4 ounces hashed brown potatoes, and 8 ounces whole milk (3.3%)]). In some embodiments, subjects are required to fast for at least 4 hours following a therapeutically effective dose of compound 1, or a crystalline form thereof; or a therapeutically effective dose of compound 3, or a crystalline form thereof. Water is allowed ad libitum except 1 hour before until 1 hour after dosing of compound 1, or a crystalline form thereof; or compound 3, or a crystalline form thereof, (with the exception of 240 mL of water provided with dosing).

In some embodiments, a therapeutically effective dose of compound 1, or a crystalline form thereof; or a therapeutically effective dose of compound 3, or a crystalline form thereof is taken while fasting (e.g., administration of single oral dose following 10-hour overnight fast).

In one embodiment, the invention encompasses an oral dosage form comprising a therapeutically effective dose of compound 1, or a crystalline form thereof or a therapeutically effective dose of compound 3, or a crystalline form thereof. In another embodiment, the invention encompasses a 5 mg, 10 mg, 25mg, 50 mg, 100 mg, 150 mg, or 200 mg (each of which is the free-base equivalent strength) oral dosage form, comprising compound 1, or a crystalline form thereof; or compound 3, or a crystalline form thereof. In one embodiment, the oral dosage form further comprises one or more pharmaceutically acceptable carrier(s).

In one embodiment, the invention encompasses compound 1, or a crystalline form thereof; or compound 3, or a crystalline form thereof, for use in a method of treating advanced hematologic malignancies, such as acute myelogenous leukemia (AML), myelodysplastic syndrome (MDS), chronic myelomonocytic leukemia (CMML), myeloid sarcoma, multiple myeloma, or lymphoma (e.g., T-cell lymphoma or B-cell lymphoma), each characterized by the presence of a mutant allele of IDH2 in a subject in need thereof. In one embodiment, the invention encompasses a pharmaceutical composition comprising a therapeutically effective dose of compound 1, or a crystalline form thereof; or a therapeutically effective dose of compound 3, or a crystalline form thereof, and one or more pharmaceutically acceptable carrier(s) for use in a method of treating advanced hematologic malignancies, such as acute myelogenous leukemia (AML), myelodysplastic syndrome (MDS), chronic myelomonocytic leukemia (CMML), myeloid sarcoma, multiple myeloma, or lymphoma (e.g., T-cell lymphoma or B-cell lymphoma), each characterized by the presence of a mutant allele of IDH2 in a subject in need thereof.

Also provided is a method of decreasing a pre-treatment or baseline level (e.g., Day −3 pre-treatment in patients, or levels measured in subjects without IDH-2 gene mutated disease) of 2-HG , decreasing a pre-treatment or baseline level (e.g., Day −3 pre-treatment in patients, or levels measured in subjects without IDH-2 gene mutated disease) of bone marrow and/or peripheral blood blast cells, and/or increasing a pre-treatment or baseline level (e.g., Day −3 pre-treatment in patients, or levels measured in subjects without IDH-2 gene mutated disease) of neutrophil count, in a subject having an advanced hematologic malignancy, such as acute myelogenous leukemia (AML), myelodysplastic syndrome (MDS), chronic myelomonocytic leukemia (CMML), myeloid sarcoma, multiple myeloma, or lymphoma (e.g., T-cell lymphoma), each characterized by the presence of a mutant allele of IDH2, comprising administering to the subject (a) compound 1, or a crystalline form thereof; or compound 3, or a crystalline form thereof at a dose of at least about 30 mg (free-base equivalent strength), once daily or twice daily (e.g., in an amount from about 30 mg to about 300 mg equivalent to free-base compound 3 (e.g., about 30 mg to about 200 mg once daily or twice daily; or about 30 mg to about 150 mg once daily or twice daily), or (b) a pharmaceutical composition comprising a compound 1, or a crystalline form thereof; or compound 3, or a crystalline form thereof at a dose of at least about 30 mg (free-base equivalent strength) (e.g., in an amount from about 30 mg to about 300 mg equivalent to free-base compound 3 (e.g., about 30 mg to about 200 mg once daily or twice daily; or about 30 mg to about 150 mg once daily or twice daily), and one or more pharmaceutically acceptable carrier(s).

Also provided is a method of decreasing a pre-treatment or baseline level (e.g., Day −3 pre-treatment in patients, or levels measured in subjects without IDH-2 gene mutated disease) of bone marrow and/or peripheral blood blast cells (e.g., by at least 50%) in a subject having an advanced hematologic malignancy, such as acute myelogenous leukemia (AML), myelodysplastic syndrome (MDS), chronic myelomonocytic leukemia (CMML), myeloid sarcoma, multiple myeloma, or lymphoma (e.g., T-cell lymphoma or B-cell lymphoma), each characterized by the presence of a mutant allele of IDH2, comprising:

acquiring knowledge of the pre-treatment or baseline level (e.g., measuring the pre-treatment or baseline level) of bone marrow and/or peripheral blood blast cells in the subject;

administering to the subject (a) compound 1, or a crystalline form thereof; or compound 3, or a crystalline form thereof at a dose of at least about 30 mg (free-base equivalent strength) (e.g., in an amount from about 30 mg to about 300 mg equivalent to free-base compound 3 (e.g., about 30 mg to about 200 mg once daily or twice daily; or about 30 mg to about 150 mg once daily or twice daily), or (b) a pharmaceutical composition comprising compound 1, or a crystalline form thereof; or compound 3, or a crystalline form thereof at a dose of at least about 30 mg (free-base equivalent strength) (e.g., in an amount from about 30 mg to about 300 mg equivalent to free-base compound 3 (e.g., about 30 mg to about 200 mg once daily or twice daily; or about 30 mg to about 150 mg once daily or twice daily), and one or more pharmaceutically acceptable carrier(s);

acquiring knowledge of the post-treatment level (e.g., measuring the post-treatment level) of bone marrow and/or peripheral blood blast cells in the subject;

comparing the post-treatment level of bone marrow and/or peripheral blood blast cells in the subject with the pre-treatment or baseline level; and determining that the level of bone marrow and/or peripheral blood blast cells is decreased (e.g., by at least 50%).

In some embodiments, the method comprises decreasing the level of bone marrow and/or peripheral blood blast cells by at least 50% (e.g., 50%, 50.5%, 51%, 51.5%, 52%, 52.5%, 53%, 53.5%, 54%, or 54.5%, 55%, 60%, 65%, 70%, 75%, 80%, 85%, 90%, or 95%) as compared to a pre-treatment or baseline level (e.g., Day −3 pretreatment in patients, or levels measured in subjects without IDH-2 gene mutated disease). In some embodiments, the method comprises decreasing the level of bone marrow and/or peripheral blood blast cells to less than 5% (e.g., 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.25%, 2.5%, 2.75%, 3%, 3.25%, 3.5%, 3.75%, 4%, 4.25%, 4.5%, 4.75%, or 5%) of the total bone marrow cells as compared to a pre-treatment or baseline level.

Also provided is a method of increasing a pre-treatment or baseline level (e.g., Day −3 pre-treatment in patients, or levels measured in subjects without IDH-2 gene mutated disease) of neutrophil count (e.g., to at least $1.0\times10^9$/L), in a subject having an advanced hematologic malignancy, such as acute myelogenous leukemia (AML), myelodysplastic syndrome (MDS), chronic myelomonocytic leukemia (CMML), myeloid sarcoma, multiple myeloma, or lymphoma (e.g., T-cell lymphoma), each characterized by the presence of a mutant allele of IDH2, comprising:

acquiring knowledge of the pre-treatment or baseline level (e.g., measuring the pre-treatment or baseline level) of neutrophil count in the subject;

administering to the subject (a) compound 1, or a crystalline form thereof; or compound 3, or a crystalline form thereof at a dose of at least about 30 mg (free-base equivalent strength) (e.g., in an amount from about 30 mg to about 300 mg equivalent to free-base compound 3 (e.g., about 30 mg to about 200 mg once daily or twice daily; or about 30 mg to about 150 mg once daily or twice daily), or (b) a pharmaceutical composition comprising a compound 1, or a crystalline form thereof; or compound 3, or a crystalline form thereof at a dose of at least about 30 mg (free-base equivalent strength) (e.g., in an amount from about 30 mg to about 300 mg equivalent to free-base compound 3(e.g., about 30 mg to about 200 mg once daily or twice daily; or about 30 mg to about 150 mg once daily or twice daily), and one or more pharmaceutically acceptable carrier(s);

acquiring knowledge of the post-treatment level (e.g., measuring the post-treatment level) of neutrophil count in the subject;

comparing the post-treatment level of neutrophil count in the subject with the pre-treatment or baseline level; and determining that the level of neutrophil count is increased (e.g., to at least $1.0\times10^9$/L).

In some embodiments, the method comprises increasing the neutrophil count in a subject, to at least $1.0\times10^9$/L, (e.g., $1.0\times10^9$/L, $1.5\times10^9$/L, $2.0\times10^9$/L, $2.5\times10^9$/L, $3.0\times10^9$/L, $3.5\times10^9$/L, $4.0\times10^9$/L, $4.5\times10^9$/L, $5.0\times10^9$/L, $5.5\times10^9$/L, $6.0\times10^9$/L, $6.5\times10^9$/L, $7.0\times10^9$/L, or $7.5\times10^9$/L). In some embodiments, the method comprises increasing the neutrophil count in a subject to at least $0.5\times10^9$/L, (e.g., $0.5\times10^9$/L, $0.6\times10^9$/L, $0.7\times10^9$/L, $0.8\times10^9$/L, $0.9\times10^9$/L, or $1.0\times10^9$/L).

In one embodiment the mutant IDH2 inhibitor is a polypeptide. In an embodiment the polypeptide acts as a dominant negative with respect to the neoactivity of the mutant enzyme. The polypeptide can correspond to full length IDH2 or a fragment thereof. The polypeptide need not be identical with the corresponding residues of wildtype IDH2, but in embodiments has at least 60, 70, 80, 90 or 95% homology with wildtype IDH2.

In one embodiment the mutant IDH2 inhibitor decreases the affinity of an IDH2 neoactive mutant protein for NADH, NADPH or a divalent metal ion, e.g., $Mg^{2+}$ or $Mn^{2+}$, or decreases the levels or availability of NADH, NADPH or divalent metal ion, e.g., $Mg^{2+}$ or $Mn^{2+}$, e.g., by competing for binding to the mutant enzyme. In an embodiment the enzyme is inhibited by replacing $Mg^{2+}$ or $Mn^{2+}$ with $Ca^{2+}$.

In one embodiment the mutant IDH2 inhibitor reduces the level a neoactivity of IDH2, e.g., 2-HG neoactivity.

In one embodiment the mutant IDH2 inhibitor reduces the level of the product of a mutant having a neoactivity of an IDH2 mutant, e.g., it reduces the level of 2-HG, e.g., R-2-HG.

In an embodiment the mutant IDH2 inhibitor interacts directly with, e.g., binds, either the mutant IDH2 protein or interacts directly with, e.g., binds, the mutant IDH2 mRNA.

In an embodiment the mutant IDH2 inhibitor interacts directly with, e.g., it binds to, the mutant IDH2 protein.

In an embodiment the mutant IDH2 inhibitor interacts directly with, e.g., it binds to, the mutant IDH2 mRNA.

In an embodiment the mutant IDH2 inhibitor reduces the amount of neoactive enzyme activity, e.g., by interacting with, e.g., binding to, mutant IDH2 protein.

In an embodiment the mutant IDH2 inhibitor is a small molecule, e.g., compound 1, and interacts with, e.g., binds, the mutant RNA, e.g., mutant IDH2 mRNA.

In some embodiments, the mutant IDH2 inhibitor may also comprise one or more isotopic substitutions. For example, H may be in any isotopic form, including $^1H$, $^2H$ (D or deuterium), and $^3H$ (T or tritium); C may be in any isotopic form, including $^{11}C$, $^{12}C$, $^{13}C$, and $^{14}C$; N may be in any isotopic form, including $^{13}N$, $^{14}N$ and $^{15}N$; O may be in any isotopic form, including $^{15}O$, $^{16}O$ and $^{18}O$; F may be in any isotopic form, including $^{18}F$; and the like. For example, the compound is enriched in a specific isotopic form of H, C, N, O and/or F by at least about 60%, 65%, 70%, 75%, 80%, 85%, 90%, 95%, 96%, 97%, 98%, or 99%. For example, isotopic substitutions to compound 1 or compound 3 may include 2-Methyl-1-[(4-[6-(trifluoromethyl)pyridin-2-yl]-6-{[2-(trifluoromethyl)pyridin-4-yl]amino}-1,3,5-triazin-2-yl-4-$^{14}C$)amino]propan-2-ol; 1-((4-(6-(difluoro(fluoro-$^{18}F$)methyl)pyridin-2-yl)-6-((2-(trifluoromethyl)pyridin-4-yl)amino)-1,3,5-triazin-2-yl)amino)-2-methylpropan-2-ol, 14(4-((2-(difluoro(fluoro-$^{18}F$)methyl)pyridin-4-yl)amino)-6-(6-(trifluoromethyl)pyridin-2-yl)-1,3,5-triazin-2-yl)amino)-2-methylpropan-2-ol, 2#(4-(6-(trifluoromethyl)pyridin-2-yl)-6-((2-(trifluoromethyl)pyridin-4-yl)amino)-1,3,5-triazin-2-yl)amino)methyl)propan-1,1,1,3,3,3-d6-2-ol; 2-methyl-1-((4-(6-(trifluoromethyl)pyridin-2-yl)-6-((2-(trifluoromethyl)pyridin-4-yl)amino)-1,3,5-triazin-2-yl)amino)propan-1,1-d2-2-ol or pharmaceutically acceptable salts thereof (e.g., 2-Methyl-1-[(4-[6-(trifluoromethyl)pyridin-2-yl]-6-{[2-(trifluoromethyl)pyridin-4-yl]amino}-1,3,5-triazin-2-yl-4-$^{14}C$)amino]propan-2-ol methanesulfonate; 1-((4-(6-(difluoro(fluoro-$^{18}F$)methyl)pyridin-2-yl)-6-((2-(trifluoromethyl)pyridin-4-yl)amino)-1,3,5-triazin-2-yl)amino)-2-methylpropan-2-ol methanesulfonate, 1-((4((2-(difluoro(fluoro-18F)methyl)pyridin-4-yl)amino)-6-(6-(trifluoromethyl)pyridin-2-yl)-1,3,5-triazin-2-yl)amino)-2-methylpropan-2-ol) methanesulfonate, 2(((4-(6-(trifluoromethyl)pyridin-2-yl)-6-((2-(trifluoromethyl)pyridin-4-yl)amino)-1,3,5-triazin-2-yl)amino)methyl)propan-1,1,1,3,3,3-d6-2-ol methanesulfonate; 2-methyl-1-((4-(6-(trifluoromethyl)pyridin-2-yl)-6((2-(trifluoromethyl)pyridin-4-yl)amino)-1,3,5-triazin-2-yl)amino)propan-1,1-d2-2-ol methanesulfonate).

These methods of treatment and pharmaceutical compositions are further illustrated by the detailed descriptions and illustrative examples given below.

Compositions and Routes of Administration

The mutant IDH2 inhibitors, e.g., compound 1, or a crystalline form thereof; or compound 3, or a crystalline form thereof utilized in the methods described herein may be formulated together with one or more pharmaceutically acceptable carrier(s) or adjuvant(s) into pharmaceutically acceptable compositions prior to being administered to a subject.

The term "pharmaceutically acceptable carrier or adjuvant" refers to a carrier or adjuvant that may be administered to a subject, together with a compound described herein, and which does not destroy the pharmacological activity thereof and is nontoxic when administered in doses sufficient to deliver a therapeutic amount of the compound.

In some embodiments, pharmaceutically acceptable carriers, adjuvants and vehicles that may be used in the pharmaceutical compositions include, but are not limited to, ion exchangers, alumina, aluminum stearate, lecithin, self-emulsifying drug delivery systems (SEDDS) such as d-a-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

In some embodiments, the pharmaceutical compositions may be administered orally, parenterally, by inhalation spray, topically, rectally, nasally, buccally, vaginally or via an implanted reservoir, preferably by oral administration or administration by injection. The pharmaceutical compositions of one aspect of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

In some embodiments, the pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

In some embodiments, the pharmaceutical compositions may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

In some embodiments, the pharmaceutical compositions may also be administered in the form of suppositories for rectal administration. These compositions can be prepared by mixing compound 1, or a crystalline form thereof; or compound 3, or a crystalline form thereof with a suitable non-irritating excipient which is solid at room temperature but liquid at the rectal temperature and therefore will melt in the rectum to release the active components. Such materials include, but are not limited to, cocoa butter, beeswax and polyethylene glycols.

In some embodiments, topical administration of the pharmaceutical compositions is useful when the desired treatment involves areas or organs readily accessible by topical application. For application topically to the skin, the pharmaceutical composition should be formulated with a suitable ointment containing the active components suspended or dissolved in a carrier. Carriers for topical administration of compound 1, or a crystalline form thereof; or compound 3, or a crystalline form thereof include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of one aspect of this invention may also be topically applied to the lower intestinal tract by rectal suppository formulation or in a suitable enema formulation. Topically-transdermal patches are also included in one aspect of this invention.

In some embodiments, the pharmaceutical compositions may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The mutant IDH2 inhibitors, e.g., compound 1, or a crystalline form thereof; or compound 3, or a crystalline form thereof, utilized in the methods described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions may be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

A subject may be administered a dose of a mutant IDH2 inhibitor, e.g., compound 1, or a crystalline form thereof; or compound 3, or a crystalline form thereof, as described in Example 5. Lower or higher doses than those recited above may be required. Specific dosage and treatment regimens for any particular subject will depend upon a variety of factors, including the activity of the specific compound employed, the age, body weight, general health status, sex, diet, time of administration, rate of excretion, drug combination, the severity and course of the disease, condition or symptoms, the subject's disposition to the disease, condition or symptoms, and the judgment of the treating physician.

Upon improvement of a subject's condition, a maintenance dose of a compound, composition, crystalline form or combination of one aspect of this invention may be administered, if necessary. Subsequently, the dosage or frequency of administration, or both, may be reduced, as a function of the symptoms, to a level at which the improved condition is retained when the symptoms have been alleviated to the desired level. Subjects may, however, require intermittent treatment on a long-term basis upon any recurrence of disease symptoms.

Some embodiments of the invention are directed toward a tablet comprising at least one pharmaceutically acceptable carrier; and a mutant IDH2 inhibitor.

Some embodiments of the invention are directed toward a tablet comprising at least one pharmaceutically acceptable carrier; and compound 1. Some embodiments of the invention are directed toward a tablet comprising at least one pharmaceutically acceptable carrier; and compound 1, or a crystalline form thereof; or compound 3, or a crystalline form thereof.

Some embodiments of the invention are directed toward a tablet comprising at least one pharmaceutically acceptable carrier or diluent; and compound 1, or a crystalline form thereof; or compound 3, or a crystalline form thereof. In other embodiments, the crystalline form of compound 1 or compound 3 is at least 90% by weight of a particular crystalline form; the particular crystalline form being a form described herein. In other embodiments, the crystalline form of compound 1 or compound 3 is at least 95% by weight of a particular crystalline form; the particular crystalline form being a form described herein.

Methods of Use

The inhibitory activities of compound 1 or a crystalline form thereof; or compound 3, or a crystalline form thereof, against IDH2 mutants (e.g., IDH2R140Q and IDH2R172K) can be tested by methods described in Example 12 of PCT Publication No. WO 2013/102431 and US Publication No. US 2013/0190287 hereby incorporated by reference in their entirety, or analogous methods.

Provided is a method for inhibiting a mutant IDH2 activity, comprising contacting a subject in need thereof with a mutant IDH2 inhibitor. In one embodiment, the method for inhibiting a mutant IDH2 activity comprises contacting a subject in need thereof with compound 1. In one embodiment, the advanced hematologic malignancy described herein, such as acute myelogenous leukemia (AML), myelodysplastic syndrome (MDS), chronic myelomonocytic leukemia (CMML), myeloid sarcoma, multiple myeloma, or lymphoma (e.g., T-cell lymphoma) to be treated is characterized by a mutant allele of IDH2 wherein the IDH2 mutation results in a new ability of the enzyme to catalyze the NAPH-dependent reduction of α-ketoglutarate to R(−)-2-hydroxyglutarate in a patient. In one aspect of this embodiment, the mutant IDH2 has an R140X mutation. In another aspect of this embodiment, the R140X mutation is a R140Q mutation. In another aspect of this embodiment, the R140X mutation is a R140W mutation. In another aspect of this embodiment, the R140X mutation is a R140L mutation. In another aspect of this embodiment, the mutant IDH2 has an R172X mutation. In another aspect of this embodiment, the R172X mutation is a R172K mutation. In another aspect of this embodiment, the R172X mutation is a R172G mutation.

In another embodiment, the method for inhibiting a mutant IDH2 activity comprises contacting a subject in need thereof with compound 1, or a crystalline form thereof or compound 3, or a crystalline form thereof. In one embodiment, the advanced hematologic malignancy described herein, such as acute myelogenous leukemia (AML), myelodysplastic syndrome (MDS), chronic myelomonocytic leukemia (CMML), myeloid sarcoma, multiple myeloma, or lymphoma (e.g., T-cell lymphoma) to be treated is characterized by a mutant allele of IDH2 wherein the IDH2 mutation results in a new ability of the enzyme to catalyze the NAPH-dependent reduction of α-ketoglutarate to R(−)-2-hydroxyglutarate in a patient. In one aspect of this embodiment, the mutant IDH2 has an R140X mutation. In another aspect of this embodiment, the R140X mutation is a R140Q mutation. In another aspect of this embodiment, the R140X mutation is a R140W mutation. In another aspect of this embodiment, the R140X mutation is a R140L mutation. In another aspect of this embodiment, the mutant IDH2 has an R172X mutation. In another aspect of this embodiment, the R172X mutation is a R172K mutation. In another aspect of this embodiment, the R172X mutation is a R172G mutation. Advanced hematologic malignancies, such as acute myelogenous leukemia (AML), myelodysplastic syndrome (MDS), chronic myelomonocytic leukemia (CMML), myeloid sarcoma, multiple myeloma, or lymphoma (e.g., T-cell lymphoma or B-cell lymphoma), each characterized by the presence of a mutant allele of IDH2, can be analyzed by sequencing cell samples to determine the presence and specific nature of (e.g., the changed amino acid present at) a mutation at amino acid 140 and/or 172 of IDH2.

In one embodiment, the efficacy of treatment of advanced hematologic malignancies, such as acute myelogenous leukemia (AML), myelodysplastic syndrome (MDS), chronic myelomonocytic leukemia (CMML), myeloid sarcoma, multiple myeloma, or lymphoma (e.g., T-cell lymphoma), each characterized by the presence of a mutant allele of IDH2, is monitored by measuring the levels of 2HG in the subject. Typically levels of 2HG are measured prior to treatment, wherein an elevated level is indicated for the use of compound 1 to treat advanced hematologic malignancy, such as acute myelogenous leukemia (AML), myelodysplastic syndrome (MDS), chronic myelomonocytic leukemia (CMML), myeloid sarcoma, multiple myeloma, or lymphoma (e.g., T-cell lymphoma), each characterized by the presence of a mutant allele of IDH2.

In one embodiment, the efficacy of treatment of advanced hematologic malignancies, such as acute myelogenous leukemia (AML), myelodysplastic syndrome (MDS), chronic myelomonocytic leukemia (CMML), myeloid sarcoma, multiple myeloma, or lymphoma (e.g., T-cell lymphoma or B-cell lymphoma), each characterized by the presence of a mutant allele of IDH2, is monitored by measuring the levels of 2-HG in the subject. Typically levels of 2-HG are measured prior to treatment, wherein an elevated level is indicated for the use of compound 1, or a crystalline form thereof; or compound 3, or a crystalline form thereof, to treat an advanced hematologic malignancy, such as acute myelogenous leukemia (AML), myelodysplastic syndrome (MDS), chronic myelomonocytic leukemia (CMML), myeloid sarcoma, multiple myeloma, or lymphoma (e.g., T-cell lymphoma or B-cell lymphoma), each characterized by the presence of a mutant allele of IDH2. Once the elevated levels are established, the level of 2-HG is determined during the course of and/or following termination of treatment to establish efficacy. In certain aspects, the level of 2-HG is only determined during the course of and/or following termination of treatment. A reduction of 2-HG levels during the course of treatment and following treatment is indicative of efficacy. Similarly, a determination that 2-HG levels are not elevated during the course of or following treatment is also indicative of efficacy. Typically, the these 2-HG measurements will be utilized together with other well-known determinations of efficacy of cancer treatment, such as reduction in number and size of tumors and/or other cancer-associated lesions, evaluation of bone marrow biopsies and/or aspirates, complete blood counts, examination of peripheral blood films, improvement in the general health of the subject, and alterations in other biomarkers that are associated with cancer treatment efficacy.

Also provided is a method of inhibiting 2-HG as compared to a pre-treatment or baseline level (e.g., Day −3 pre-treatment in patients, or levels measured in subjects without IDH-2 gene mutated disease) of 2-HG (e.g., by at least 50%) in a subject having an advanced hematologic malignancy, such as acute myelogenous leukemia (AML), myelodysplastic syndrome (MDS), chronic myelomonocytic leukemia (CMML), myeloid sarcoma, multiple myeloma, or lymphoma (e.g., T-cell lymphoma or B-cell lymphoma), each characterized by the presence of a mutant allele of IDH2, comprising:

acquiring knowledge of the pre-treatment or baseline level (e.g., measuring the pre-treatment or baseline level) of 2-HG in the subject;

administering to the subject (a) compound 1, or a crystalline form thereof; or compound 3, or a crystalline form thereof at a dose of at least about 30 mg (free-base equivalent strength) (e.g., in an amount from about 30 mg to about 300 mg equivalent to free-base compound 3), or (b) a pharmaceutical composition comprising compound 1, or a crystalline form thereof; or compound 3, or a crystalline form thereof at a dose of at least about 30 mg (free-base equivalent strength) (e.g., in an amount from about 30 mg to about 300 mg equivalent to free-base compound 3), and one or more pharmaceutically acceptable carrier(s);

acquiring knowledge of the post-treatment level (e.g., measuring the post-treatment level) of 2-HG in the subject;

comparing the post-treatment level of 2-HG in the subject with the pre-treatment or baseline level; and determining that the level of 2-HG is inhibited (e.g., by at least 50%).

In some embodiments, the method comprises inhibiting 2-HG in patients having or determined to have an IDH2 R140Q mutation by at least 50% (e.g., 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100%) as compared to a pre-treatment or baseline level (e.g., Day −3 pretreatment in patients, or levels measured in subjects without IDH-2 gene mutated disease). In some embodiments, the method comprises inhibiting 2-HG in patients having or determined to have an IDH2 R172K mutation by up to 60% (e.g., decreasing the level of 2-HG by up to 50%, 51%, 52%, 53%, 54%, 55%, 56%, 57%, 58%, 59%, or 60%) as compared to a pre-treatment or baseline level (e.g., Day −3 pre-treatment in patients, or levels measured in subjects without IDH-2 gene mutated disease). In some embodiments, measuring the 2-HG level in the subject may be achieved by spectroscopic analysis, e.g., magnetic resonance-based analysis, e.g., MRI and/or MRS measurement, sample analysis of bodily fluid, such as blood, plasma, urine, bone marrow, or spinal cord fluid analysis, or by analysis of surgical material, e.g., by mass-spectroscopy (e.g. LC-MS, GC-MS).

2-HG can be detected in a sample by the methods of PCT Publication No. WO 2013/102431 and US Publication No. US 2013/0190287 hereby incorporated by reference in their entirety, or by analogous methods.

In one embodiment 2-HG is directly evaluated.

In another embodiment a derivative of 2-HG formed in process of performing the analytic method is evaluated. By way of example such a derivative can be a derivative formed in MS analysis. Derivatives can include a salt adduct, e.g., a Na adduct, a hydration variant, or a hydration variant which is also a salt adduct, e.g., a Na adduct, e.g., as formed in MS analysis.

In another embodiment a metabolic derivative of 2-HG is evaluated. Examples include species that build up or are elevated, or reduced, as a result of the presence of 2-HG, such as glutarate or glutamate that will be correlated to 2-HG, e.g., R-2-HG.

Exemplary 2-HG derivatives include dehydrated derivatives such as the compounds provided below or a salt adduct thereof:

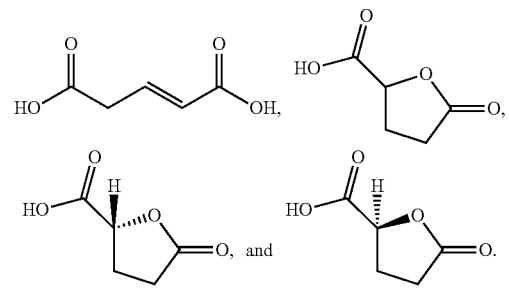

In one embodiment, the advanced hematologic malignancy, such as acute myelogenous leukemia (AML), myelodysplastic syndrome (MDS), chronic myelomonocytic leukemia (CMML), myeloid sarcoma, multiple myeloma, or lymphoma (e.g., T-cell lymphoma or B-cell lymphoma), each characterized by the presence of a mutant allele of IDH2, is a tumor wherein at least 30, 40, 50, 60, 70, 80 or 90% of the tumor cells carry an IDH2 mutation, and in particular an IDH2 R140Q, R140W, or R140L and/or R172K or R172G mutation, at the time of diagnosis or treatment.

In some embodiments, the subject has or is determined to have an IDH2 gene-mutated disease (e.g., R140Q mutation or R172K mutation) at the time of diagnosis or treatment. In some embodiments, the subject also has or is determined to have a mutation selected from FLT3-ITD (Fms-related tyrosine kinase 3 (FLT3) internal tandem duplication (ITD)), CEPBA (CCAAT/enhancer binding protein alpha), NPM1 (nucleophosmin (neucleolar phosphoprotein B23)), and DNMT3A (DNA (cytosine-5-)methyltransferase 3 alpha, ASXL1: additional sex combs like 1) at the time of diagnosis or treatment.

In some embodiments, the subject has normal cytogenetics prior to treatment. In some other embodiments, the subject has abnormal or unfavorable cytogenetics, for example, one or more of: Monosomy 7 (or partial deletion of the long arm of chromosome 7 (7q-)), Trisomy 8, Trisomy 11, translocation t(17; 18), or translocation t(1; 13) prior to treatement. Table 8 describes the cytogenetic classification (IPSS and new 5-group classification).

In one embodiment, the advanced hematologic malignancy to be treated is AML. In some embodiments, the AML is relapsed and/or primary refractory. In other embodiments, the AML is untreated. In some embodiments, the AML is relapsed and/or primary refractory in patients 60 years of age and older. In some embodiments, the AML is untreated in patients 60 years of age and older. In some embodiments, the AML is relapsed and/or primary refractory in patients under 60 years of age. In one embodiment, compound 1 is administered as a first line treatment for AML. In one embodiment, compound 1 is administered as a second line, third line, or fourth line treatment for AML. In one embodiment, compound 1, or a crystalline form thereof; or compound 3, or a crystalline form thereof, is administered as a first line treatment for AML. In one embodiment, compound 1, or a crystalline form thereof; or compound 3, or a crystalline form thereof, is administered as a second line, third line, or fourth line treatment for AML. In one embodiment, compound 1, or a crystalline form thereof; or compound 3, or a crystalline form thereof, is administered after a first relapse. In one embodiment, compound 1 is administered after primary induction failure. In one embodiment, compound 1 is administered after re-induction failure. In one embodiment, administration of compound 1 can occur prior to, during, or after transplant. In one embodiment, compound 1 is administered after a relapse that is post-transplant. In one embodiment, the AML presentation is subsequent to MPD. In one embodiment, the AML presentation is subsequent to MDS and CMML. In one embodiment, compound 1, or a crystalline form thereof; or compound 3, or a crystalline form thereof, is administered after primary induction failure. In one embodiment, compound 1, or a crystalline form thereof; or compound 3, or a crystalline form thereof, is administered after re-induction failure. In one embodiment, administration of compound 1, or a crystalline form thereof; or compound 3, or a crystalline form thereof, can occur prior to, during, or after transplant. In one embodiment, compound 1, or a crystalline form thereof; or compound 3, or a crystalline form thereof, is administered after a relapse that is post-transplant. In one embodiment, after relapse and subsequent re-induction failure, compound 1, or a crystalline form thereof; or compound 3, or a crystalline form thereof, is administered. In one embodiment, after relapse (post-transplant) and subsequent re-induction failure, compound 1, or a crystalline form thereof; or compound 3, or a crystalline form thereof, is administered. In one embodiment, the AML presentation is subsequent to MPD, and compound 1, or a crystalline form thereof; or compound 3, or a crystalline form thereof, is administered after primary induction failure. In one embodiment, after primary induction failure and subsequent relapse (post-transplant), compound 1, or a crystalline form thereof; or compound 3, or a crystalline form thereof, is administered. In one embodiment, the AML presentation is subsequent to MDS and CMML, and after primary induction failure and subsequent re-induction failure, compound 1, or a crystalline form thereof; or compound 3, or a crystalline form thereof, is administered.

In another embodiment, the advanced hematologic malignancy to be treated is MDS with refractory anemia with excess blasts (subtype RAEB-1 or RAEB-2). In other embodiments, the MDS is untreated. In one embodiment, compound 1, or a crystalline form thereof; or compound 3, or a crystalline form thereof, is administered as a first line treatment for MDS. In one embodiment, compound 1, or a crystalline form thereof; or compound 3, or a crystalline form thereof, is administered as a second line, third line, or fourth line treatment for MDS. In one embodiment, compound 1 is administered as a first line treatment for MDS. In one embodiment, compound 1 is administered as a second line, third line, or fourth line treatment for MDS. In one embodiment, the MDS presentation is subsequent to AML. In one embodiment, the MDS presentation is subsequent to AML, and compound 1, or a crystalline form thereof; or compound 3, or a crystalline form thereof, is administered as a first line treatment for MDS.

In another embodiment, the advanced hematologic malignancy to be treated is relapsed and/or primary refractory CMML. In one embodiment, compound 1 is administered as a first line treatment for CMML. In one embodiment, compound 1 is administered as a second line, third line, or fourth line treatment for CMML. In one embodiment, compound 1, or a crystalline form thereof; or compound 3, or a crystalline form thereof, is administered as a first line treatment for CMML. In one embodiment, compound 1, or a crystalline form thereof; or compound 3, or a crystalline form thereof, is administered as a second line, third line, or fourth line treatment for CMML. In one embodiment, compound 1, or a crystalline form thereof; or compound 3, or a crystalline form thereof, is administered after a second relapse.

In another embodiment, the advanced hematologic malignancy to be treated is lymphoma (e.g., Non-Hodgkin lymphoma (NHL) such as B-cell lymphoma (e.g., Burkitt lymphoma, chronic lymphocytic leukemia/small lymphocytic lymphoma (CLL/SLL), diffuse large B-cell lymphoma, follicular lymphoma, immunoblastic large cell lymphoma, precursor B-lymphoblastic lymphoma, and mantle cell lymphoma) and T-cell lymphoma (e.g., mycosis fungoides, anaplastic large cell lymphoma, and precursor T-lymphoblastic lymphoma).

In another embodiment, the advanced hematologic malignancy to be treated is relapsed and/or primary refractory myeloid sarcoma. In other embodiments, the myeloid sarcoma is untreated. In one embodiment, compound 1 is administered as a first line treatment for myeloid sarcoma. In one embodiment, compound 1 is administered as a second line, third line, or fourth line treatment for myeloid sarcoma. In one embodiment, compound 1, or a crystalline form thereof; or compound 3, or a crystalline form thereof, is administered as a first line treatment for myeloid sarcoma. In one embodiment, compound 1, or a crystalline form thereof; or compound 3, or a crystalline form thereof, is administered as a second line, third line, or fourth line treatment for myeloid sarcoma. In one embodiment, the myeloid sarcoma presents concurrently with AML. In one embodiment, the myeloid sarcoma presents at relapse of AML.

In another embodiment, the advanced hematologic malignancy to be treated is relapsed and/or primary refractory multiple myeloma. In other embodiments, the multiple myeloma is untreated. In one embodiment, compound 1 is administered as a first line treatment for multiple myeloma. In one embodiment, compound 1 is administered as a second line, third line, or fourth line treatment for multiple myeloma. In other embodiments, the multiple myeloma is untreated. In one embodiment, compound 1, or a crystalline form thereof; or compound 3, or a crystalline form thereof, is administered as a first line treatment for multiple myeloma. In one embodiment, compound 1, or a crystalline form thereof; or compound 3, or a crystalline form thereof, is administered as a second line, third line, or fourth line treatment for multiple myeloma.

Treatment methods described herein can additionally comprise various evaluation steps prior to and/or following treatment with a mutant IDH2 inhibitor, e.g., compound 1, or a crystalline form thereof; or compound 3, or a crystalline form thereof.

In one embodiment, prior to and/or after treatment with a mutant IDH2 inhibitor, e.g., compound 1, or a crystalline form thereof; or compound 3, or a crystalline form thereof, the method further comprises the step of evaluating the growth, size, weight, invasiveness, stage and/or other phenotype of the advanced hematologic malignancy.

In one embodiment, prior to and/or after treatment with a mutant IDH2 inhibitor, e.g., compound 1, or a crystalline form thereof; or compound 3, or a crystalline form thereof, the method further comprises the step of evaluating the IDH2 genotype of the cancer. This may be achieved by ordinary methods in the art, such as DNA sequencing, immuno analysis, and/or evaluation of the presence, distribution or level of 2-HG.

In one embodiment, prior to and/or after treatment with a mutant IDH2 inhibitor, e.g., compound 1, or a crystalline form thereof; or compound 3, or a crystalline form thereof, the method further comprises the step of determining the 2-HG level in the subject. This may be achieved by spectroscopic analysis, e.g., magnetic resonance-based analysis, e.g., MRI and/or MRS measurement, sample analysis of bodily fluid, such as blood, plasma, urine, bone marrow, or spinal cord fluid analysis, or by analysis of surgical material, e.g., by mass-spectroscopy (e.g. LC-MS, GC-MS).

Crystalline Forms

Provided are crystalline forms of compound 1. Also provided are crystalline forms of 2-Methyl-1-[(4-[6-(trifluoromethyl)pyridin-2-yl]-6-{[2-(trifluoromethyl)pyridin-4-yl]amino}-1,3,5-triazin-2-yl)amino]propan-2-ol (compound 3).

In one embodiment, compound 1 is a single crystalline form, or any one of the single crystalline forms described herein. Also provided are pharmaceutical compositions comprising at least one pharmaceutically acceptable carrier or diluent; and compound 1, wherein compound 1 is a single crystalline form, or any one of the crystalline forms being described herein. Also provided are uses of compound 1, wherein compound 1 is a single crystalline form, or any one of the single crystalline forms described herein, to prepare a pharmaceutical composition.

In one embodiment, compound 3 is a single crystalline form, or any one of the single crystalline forms described herein. Also provided are pharmaceutical compositions comprising at least one pharmaceutically acceptable carrier or diluent; and compound 3, wherein compound 3 is a single crystalline form, or any one of the crystalline forms being described herein. Also provided are uses of compound 3, wherein compound 3 is a single crystalline form, or any one of the single crystalline forms described herein, to prepare a pharmaceutical composition.

Also provided are methods of treating advanced hematologic malignancies, such as acute myelogenous leukemia (AML), myelodysplastic syndrome (MDS), chronic myelomonocytic leukemia (CMML), myeloid sarcoma, multiple myeloma, or lymphoma (e.g., T-cell lymphoma or B-cell lymphoma), each characterized by the presence of a mutant allele of IDH2, comprising administering to subject in need thereof (a) a single crystalline form of compound 1 or compound 3, or (b) a pharmaceutical composition comprising (a) and a pharmaceutically acceptable carrier. In one embodiment, the single crystalline form in (a) is any percentage between 90% and 100% pure.

Also provided are methods of treating advanced hematologic malignancies, such as acute myelogenous leukemia (AML), myelodysplastic syndrome (MDS), chronic myelomonocytic leukemia (CMML), or lymphoma (e.g., T-cell lymphoma), each characterized by the presence of a mutant allele of IDH2, comprising administering to subject in need thereof (a) a single crystalline form of compound 1 or compound 3, or (b) a pharmaceutical composition comprising (a) and a pharmaceutically acceptable carrier. In one embodiment, the single crystalline form in (a) is any percentage between 90% and 100% pure.

Provided herein is an assortment of characterizing information to describe the crystalline forms of compound 1 and compound 3. It should be understood, however, that not all such information is required for one skilled in the art to determine that such particular form is present in a given composition, but that the determination of a particular form can be achieved using any portion of the characterizing information that one skilled in the art would recognize as sufficient for establishing the presence of a particular form, e.g., even a single distinguishing peak can be sufficient for one skilled in the art to appreciate that such particular form is present.

Crystalline forms of compound 1 have physical properties that are suitable for large scale pharmaceutical formulation manufacture. Many of the crystalline forms of compound 1 described herein exhibit high crystallinity, high melting point, and limited occluded or solvated solvent. Crystalline forms of compound 1 have improved bioavailability as compared to amporphous forms of compound 1. In particular, Form 3 is non-hygroscopic, and exhibits stability advantages (e.g., thermodynamic, chemical, or physical stability) at a relative humidity of up to 40% at room temperature for at least 3 months.

In one embodiment, at least a particular percentage by weight of compound 3 is crystalline. Particular weight percentages may be 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5%, 99.9%, or any percentage between 10% and 100%. When a particular percentage by weight of compound 3 is crystalline, the remainder of compound 3 is the amorphous form of compound 3. Non-limiting examples of crystalline compound 3 include a single crystalline form of compound 3 or a mixture of different single crystalline forms. In some embodiments, compound 3 is at least 90% by weight crystalline. In some other embodiments, compound 3 is at least 95% by weight crystalline.

In another embodiment, a particular percentage by weight of the crystalline compound 3 is a specific single crystalline form or a combination of single crystalline forms. Particular weight percentages may be 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5%, 99.9%, or any percentage between 10% and 100%. In another embodiment, compound 3 is at least 90% by weight of a single crystalline form. In another embodiment, compound 3 is at least 95% A by weight of a single crystalline form.

In one embodiment, at least a particular percentage by weight of compound 1 is crystalline. Particular weight percentages may be 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5%, 99.9%, or any percentage between 10% and 100%. When a particular percentage by weight of compound 1 is crystalline, the remainder of compound 1 is the amorphous form of compound 1. Non-limiting examples of crystalline compound 1 include a single crystalline form of compound 1 or a mixture of different single crystalline forms. In some embodiments, compound 1 is at least 90% by weight crystalline. In some other embodiments, compound 1 is at least 95% by weight crystalline.

In another embodiment, a particular percentage by weight of the crystalline compound 1 is a specific single crystalline form or a combination of single crystalline forms. Particular weight percentages may be 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5%, 99.9%, or any percentage between 10% and 100%. In another embodiment, compound 1 is at least 90% by weight of a single crystalline form. In another embodiment, compound 1 is at least 95% by weight of a single crystalline form.

In the following description of compound 3, embodiments of the invention may be described with reference to a particular crystalline form of compound 3, as characterized by one or more properties as discussed herein. The descriptions characterizing the crystalline forms may also be used to describe the mixture of different crystalline forms that may be present in a crystalline compound 3. However, the particular crystalline forms of compound 3 may also be characterized by one or more of the characteristics of the crystalline form as described herein, with or without regard to referencing a particular crystalline form.

In the following description of compound 1, embodiments of the invention may be described with reference to a particular crystalline form of compound 1, as characterized by one or more properties as discussed herein. The descriptions characterizing the crystalline forms may also be used to describe the mixture of different crystalline forms that may be present in a crystalline compound 1. However, the particular crystalline forms of compound 1 may also be characterized by one or more of the characteristics of the crystalline form as described herein, with or without regard to referencing a particular crystalline form.

The crystalline forms are further illustrated by the detailed descriptions and illustrative examples given below. The XRPD peaks described in Tables 1A to 19A may vary by ±0.2° depending upon the instrument used to obtain the data. The intensity of the XRPD peaks described in Tables 1A to 19A may vary by 10%.

Form 1

In one embodiment, a single crystalline form, Form 1, of the compound 3 is characterized by the X-ray powder diffraction (XRPD) pattern shown in FIG. 1, and data shown in Table 1, obtained using CuKa radiation. In a particular embodiment, the polymorph can be characterized by one or more of the peaks taken from FIG. 1, as shown in Table 1A. For example, the polymorph can be characterized by one or two or three or four or five or six or seven or eight or nine of the peaks shown in Table 1A.

TABLE 1A

| Angle 2-Theta° | Intensity % |
|---|---|
| 6.7 | 42.2 |
| 8.9 | 61.8 |
| 9.1 | 41.9 |
| 13.0 | 46.7 |
| 16.4 | 33.2 |
| 18.9 | 100.0 |
| 21.4 | 27.3 |
| 23.8 | 49.2 |
| 28.1 | 47.5 |

In another embodiment, Form 1 can be characterized by the peaks identified at 2θ angles of 8.9, 13.0, 18.9, 23.8, and 28.1°. In another embodiment, Form 1 can be characterized by the peaks identified at 2θ angles of 8.9, 18.9, and 24.8°.

Form 2

In one embodiment, a single crystalline form, Form 2, of the compound 3 is characterized by the X-ray powder diffraction (XRPD) pattern shown in FIG. 2, and data shown in Table 2A, obtained using CuKa radiation. In a particular embodiment, the polymorph can be characterized by one or more of the peaks taken from FIG. 2, as shown in Table 2A. For example, the polymorph can be characterized by one or two or three or four or five or six or seven or eight or nine of the peaks shown in Table 2A.

TABLE 2A

| Angle 2-Theta° | Intensity % |
|---|---|
| 8.4 | 65.2 |
| 12.7 | 75.5 |
| 16.9 | 57.9 |
| 17.1 | 69.4 |
| 17.7 | 48.6 |
| 19.2 | 100.0 |
| 23.0 | 69.7 |
| 23.3 | 61.1 |
| 24.2 | 87.3 |

In another embodiment, Form 2 can be characterized by the peaks identified at 2θ angles of 12.7, 17.1, 19.2, 23.0, and 24.2°. In another embodiment, Form 2 can be characterized by the peaks identified at 2θ angles of 12.7, 19.2, and 24.2°.

In another embodiment, Form 2 can be characterized by the differential scanning calorimetry profile (DSC) shown in FIG. 3. The DSC graph plots the heat flow as a function of temperature from a sample, the temperature rate change being about 10° C./min. The profile is characterized by a strong endothermic transition with an onset temperature of about 88.2° C. with a melt at about 91.0° C.

In another embodiment, Form 2 can be characterized by thermal gravimetric analysis (TGA) shown in FIG. 4. The TGA profile graphs the percent loss of weight of the sample as a function of temperature, the temperature rate change being about 10° C./min. The weight loss represents a loss of about 9.9% of the weight of the sample as the temperature is changed from about 26.6° C. to 150.0° C.

Form 3

In one embodiment, a single crystalline form, Form 3, of the compound 1 is characterized by the X-ray powder diffraction (XRPD) pattern shown in FIG. 5, and data shown in Table 3A, obtained using CuKa radiation. In a particular embodiment, the polymorph can be characterized by one or more of the peaks taken from FIG. 5, as shown in Table 3A. For example, the polymorph can be characterized by one or two or three or four or five or six or seven or eight or nine or ten of the peaks shown in Table 3A.

TABLE 3A

| Angle 2-Theta° | Intensity % |
| --- | --- |
| 7.5 | 100.0 |
| 9.0 | 16.5 |
| 9.3 | 27.2 |
| 14.5 | 48.5 |
| 15.2 | 17.2 |
| 18.0 | 17.0 |
| 18.8 | 32.6 |
| 19.9 | 18.7 |
| 21.3 | 19.3 |
| 24.8 | 33.8 |

In another embodiment, Form 3 can be characterized by the peaks identified at 2θ angles of 7.5, 9.3, 14.5, 18.8, 21.3, and 24.8°. In a further embodiment, Form 3 can be characterized by the peaks are identified at 2θ angles of 7.5, 14.5, 18.8, and 24.8°. In another, embodiment, Form 3 can be characterized by the peaks identified at 2θ angles of 7.5, 14.5, and 24.8°.

In another embodiment, Form 3 can be characterized by the differential scanning calorimetry profile (DSC) shown in FIG. 6. The DSC graph plots the heat flow as a function of temperature from a sample, the temperature rate change being about 10° C./min. The profile is characterized by a strong endothermic transition with an onset temperature of about 210.7° C. with a melt at about 213.4° C.

In another embodiment, Form 3 can be characterized by thermal gravimetric analysis (TGA) shown in FIG. 7. The TGA profile graphs the percent loss of weight of the sample as a function of temperature, the temperature rate change being about 10° C./min. The weight loss represents a loss of about 0.03% of the weight of the sample as the temperature is changed from about 21° C. to 196° C. and about 7.5% of the weight of the sample as the temperature is changed from about 196° C. to 241° C.

In another embodiment, Form 3 is characterized by an X-ray powder diffraction pattern substantially similar to FIG. 5. In another embodiment, Form 3 is characterized by a differential scanning calorimetry (DSC) profile substantially similar to FIG. 6. In another embodiment, Form 3 is characterized by a thermal gravimetric analysis (TGA) profile substantially similar to FIG. 7. In further embodiments, a single crystalline form of Form 3 is characterized by one or more of the features listed in this paragraph. In another embodiment, Form 3 is characterized by a DVS profile substantially similar to FIG. 8.

Form 4

In one embodiment, a single crystalline form, Form 4, of the compound 1 is characterized by the X-ray powder diffraction (XRPD) pattern shown in FIG. 9, and data shown in Table 4A, obtained using CuKa radiation. In a particular embodiment, the polymorph can be characterized by one or more of the peaks taken from FIG. 9, as shown in Table 4A. For example, the polymorph can be characterized by one or two or three or four or five or six or seven or eight or nine of the peaks shown in Table 4A.

TABLE 4A

| Angle 2-Theta° | Intensity % |
| --- | --- |
| 6.2 | 28.9 |
| 6.5 | 38.0 |
| 7.5 | 29.5 |
| 18.6 | 25.0 |
| 19.0 | 34.8 |
| 19.4 | 58.8 |
| 19.9 | 100.0 |
| 22.9 | 31.0 |
| 24.7 | 36.9 |

In another embodiment, Form 4 can be characterized by the peaks identified at 2θ angles of 6.5, 19.0, 19.4, 19.9, and 24.7°. In a further embodiment, Form 4 can be characterized by the peaks are identified at 2θ angles of 6.5, 19.4, and 19.9°.

In another embodiment, Form 4 can be characterized by the differential scanning calorimetry profile (DSC) shown in FIG. 10. The DSC graph plots the heat flow as a function of temperature from a sample, the temperature rate change being about 10° C./min. The profile is characterized by a weak endothermic transition with an onset temperature of about 59.2° C. with a melt at about 85.5° C. and a strong endothermic transition with an onset temperature of about 205.2° C. with a melt at about 209.1° C.

In another embodiment, Form 4 can be characterized by thermal gravimetric analysis (TGA) shown in FIG. 10. The TGA profile graphs the percent loss of weight of the sample as a function of temperature, the temperature rate change being about 10° C./min. The weight loss represents a loss of about 1.8% of the weight of the sample as the temperature is changed from about 44.8° C. to 140.0° C.

Form 5

In one embodiment, a single crystalline form, Form 5, of the compound 1 is characterized by the X-ray powder diffraction (XRPD) pattern shown in FIG. 11, and data shown in Table 5, obtained using CuKa radiation. In a particular embodiment, the polymorph can be characterized by one or more of the peaks taken from FIG. 11, as shown in Table 5A. For example, the polymorph can be characterized by one or two or three or four or five or six or seven or eight or nine of the peaks shown in Table 5A.

TABLE 5A

| Angle 2-Theta° | Intensity % |
| --- | --- |
| 7.1 | 100.0 |
| 14.5 | 40.0 |
| 17.1 | 29.8 |
| 19.2 | 6.1 |
| 21.8 | 47.8 |
| 22.7 | 7.7 |
| 23.4 | 6.5 |
| 28.5 | 2.1 |
| 29.4 | 17.6 |

In one embodiment, Form 5 can be characterized by the peaks identified at 2θ angles of 7.1, 14.5, 17.1, and 21.8°. In a further embodiment, Form 5 can be characterized by the peaks are identified at 2θ angles of 7.1 and 21.8°.

In another embodiment, Form 5 can be characterized by the differential scanning calorimetry profile (DSC) shown in FIG. 12. The DSC graph plots the heat flow as a function of temperature from a sample, the temperature rate change being about 10° C./min. The profile is characterized by a weak endothermic transition with an onset temperature of about 50.1° C. with a melt at about 77.5° C. and a strong endothermic transition with an onset temperature of about 203.1° C. with a melt at about 208.2° C.

In another embodiment, Form 5 can be characterized by thermal gravimetric analysis (TGA) shown in FIG. 12. The TGA profile graphs the percent loss of weight of the sample as a function of temperature, the temperature rate change being about 10° C./min. The weight loss represents a loss of about 0.3% of the weight of the sample as the temperature is changed from about 36.0° C. to 120.0° C.

Form 6

In one embodiment, a single crystalline form, Form 6, of the compound 1 is characterized by the X-ray powder diffraction (XRPD) pattern shown in FIG. 13, and data shown in Table 6A, obtained using CuKa radiation. In a particular embodiment, the polymorph can be characterized by one or more of the peaks taken from FIG. 13, as shown in Table 6A. For example, the polymorph can be characterized by one or two or three or four or five or six or seven or eight or nine of the peaks shown in Table 6A.

TABLE 6A

| Angle 2-Theta° | Intensity % |
| --- | --- |
| 6.3 | 53.7 |
| 7.2 | 100.0 |
| 8.1 | 71.5 |
| 12.2 | 19.2 |
| 12.7 | 34.0 |
| 14.9 | 37.2 |
| 17.9 | 21.4 |
| 18.4 | 31.0 |
| 26.4 | 20.2 |

In another embodiment, Form 6 can be characterized by the peaks identified at 2θ angles of 6.3, 7.2, 8.1, 12.7, and 14.9°. In a further embodiment, Form 6 can be characterized by the peaks are identified at 2θ angles of 6.3, 7.2, and 8.1°.

In another embodiment, Form 6 can be characterized by the differential scanning calorimetry profile (DSC) shown in FIG. 14. The DSC graph plots the heat flow as a function of temperature from a sample, the temperature rate change being about 10° C./min. The profile is characterized by three weak endothermic transitions: with an onset temperature of about 61.7° C. with a melt at about 86.75° C., an onset temperature of about 140.0° C. with a melt at about 149.0° C., and an onset temperature of about 175.3° C. with a melt at about 192.1° C.

In another embodiment, Form 6 can be characterized by thermal gravimetric analysis (TGA) shown in FIG. 14. The TGA profile graphs the percent loss of weight of the sample as a function of temperature, the temperature rate change being about 10° C./min. The weight loss represents a loss of about 5.4% of the weight of the sample as the temperature is changed from about 31.8° C. to 150.0° C.

Form 7

In one embodiment, a single crystalline form, Form 7, of the compound 1 is characterized by the X-ray powder diffraction (XRPD) pattern shown in FIG. 15, and data shown in Table 7A, obtained using CuKa radiation. In a particular embodiment, the polymorph can be characterized by one or more of the peaks taken from FIG. 15, as shown in Table 7A. For example, the polymorph can be characterized by one or two or three or four or five or six or seven or eight or nine of the peaks shown in Table 7A.

TABLE 7A

| Angle 2-Theta° | Intensity % |
| --- | --- |
| 9.7 | 32.5 |
| 14.1 | 59.0 |
| 18.6 | 35.7 |
| 19.1 | 100.0 |
| 20.2 | 50.6 |
| 21.8 | 65.9 |
| 23.5 | 72.4 |
| 25.7 | 57.7 |
| 28.9 | 27.7 |

In another embodiment, Form 7 can be characterized by the peaks identified at 2θ angles of 14.1, 19.1, 21.8, 23.5, and 25.7°. In a further embodiment, Form 7 can be characterized by the peaks are identified at 2θ angles of 19.1, 21.8, and 23.5°.

In another embodiment, Form 7 can be characterized by the differential scanning calorimetry profile (DSC) shown in FIG. 16. The DSC graph plots the heat flow as a function of temperature from a sample, the temperature rate change being about 10° C./min. The profile is characterized by a strong endothermic transition with an onset temperature of about 213.6° C. with a melt at about 214.7° C.

In another embodiment, Form 7 can be characterized by thermal gravimetric analysis (TGA) shown in FIG. 16. The TGA profile graphs the percent loss of weight of the sample as a function of temperature, the temperature rate change being about 10° C./min. The weight loss represents a loss of about 0.01% of the weight of the sample as the temperature is changed from about 32.2° C. to 150.0° C.

Form 8

In one embodiment, a single crystalline form, Form 8, of the compound 1 is characterized by the X-ray powder diffraction (XRPD) pattern shown in FIG. 17, and data shown in Table 8A, obtained using CuKa radiation. In a particular embodiment, the polymorph can be characterized by one or more of the peaks taken from FIG. 17, as shown in Table 8A. For example, the polymorph can be characterized by one or two or three or four or five or six or seven or eight or nine of the peaks shown in Table 8A.

TABLE 8A

| Angle 2-Theta° | Intensity % |
| --- | --- |
| 9.0 | 38.7 |
| 9.2 | 39.6 |
| 14.1 | 12.0 |
| 16.8 | 21.9 |
| 19.9 | 53.4 |
| 21.9 | 100.0 |
| 22.1 | 65.9 |
| 24.2 | 56.6 |
| 24.6 | 66.7 |

In another embodiment, Form 8 can be characterized by the peaks identified at 2θ angles of 9.0, 9.2, 21.9, 22.1, 24.2, and 24.6°. In a further embodiment, Form 8 can be characterized by the peaks are identified at 2θ angles of 21.9, 22.1, 24.2, and 24.6°.

In another embodiment, Form 8 can be characterized by the differential scanning calorimetry profile (DSC) shown in FIG. 18. The DSC graph plots the heat flow as a function of temperature from a sample, the temperature rate change being about 10° C./min. The profile is characterized by a strong endothermic transition with an onset temperature of about 211.5° C. with a melt at about 212.8° C.

In another embodiment, Form 8 can be characterized by thermal gravimetric analysis (TGA) shown in FIG. 18. The TGA profile graphs the percent loss of weight of the sample as a function of temperature, the temperature rate change being about 10° C./min. The weight loss represents a loss of about 0.2% of the weight of the sample as the temperature is changed from about 31.2° C. to 150.0° C.

Form 9

In one embodiment, a single crystalline form, Form 9, of the compound 1 is characterized by the X-ray powder diffraction (XRPD) pattern shown in FIG. 19, and data shown in Table 9A, obtained using CuKa radiation. In a particular embodiment, the polymorph can be characterized by one or more of the peaks taken from FIG. 19, as shown in Table 9A. For example, the polymorph can be characterized by one or two or three or four or five or six or seven or eight or nine of the peaks shown in Table 9A.

TABLE 9A

| Angle 2-Theta° | Intensity % |
|---|---|
| 6.5 | 33.8 |
| 10.7 | 21.8 |
| 17.7 | 8.6 |
| 18.4 | 23.7 |
| 19.0 | 13.6 |
| 19.6 | 40.1 |
| 20.1 | 100.0 |
| 21.6 | 26.9 |
| 29.9 | 9.9 |

In another embodiment, Form 9 can be characterized by the peaks identified at 2θ angles of 6.5, 19.6, 20.1, and 21.6°. In a further embodiment, Form 9 can be characterized by the peaks are identified at 2θ angles of 19.6 and 20.1°.

In another embodiment, Form 9 can be characterized by the differential scanning calorimetry profile (DSC) shown in FIG. 20. The DSC graph plots the heat flow as a function of temperature from a sample, the temperature rate change being about 10° C./min. The profile is characterized by a strong endothermic transition with an onset temperature of about 172.3° C. with a melt at about 175.95° C. and an endothermic transition with an onset temperature of about 192.3° C. with a melt at about 202.1° C.

In another embodiment, Form 9 can be characterized by thermal gravimetric analysis (TGA) shown in FIG. 20. The TGA profile graphs the percent loss of weight of the sample as a function of temperature, the temperature rate change being about 10° C./min. The weight loss represents a loss of about 0.7% of the weight of the sample as the temperature is changed from about 24.7° C. to 150.0° C.

Form 10

In one embodiment, a single crystalline form, Form 10, of the compound 1 is characterized by the X-ray powder diffraction (XRPD) pattern shown in FIG. 21, and data shown in Table 10A, obtained using CuKa radiation. In a particular embodiment, the polymorph can be characterized by one or more of the peaks taken from FIG. 21, as shown in Table 10A. For example, the polymorph can be characterized by one or two or three or four or five or six or seven or eight or nine of the peaks shown in Table 10A.

TABLE 10A

| Angle 2-Theta° | Intensity % |
|---|---|
| 6.7 | 46.8 |
| 7.7 | 31.0 |
| 9.1 | 100.0 |
| 10.8 | 76.9 |
| 13.3 | 11.6 |
| 16.0 | 15.6 |
| 19.9 | 84.6 |
| 21.9 | 52.3 |
| 25.8 | 15.2 |

In another embodiment, Form 10 can be characterized by the peaks identified at 2θ angles of 6.7, 9.1, 10.8, 19.9, and 21.9°. In a further embodiment, Form 10 can be characterized by the peaks are identified at 2θ angles of 9.1, 10.8, and 19.9°.

In another embodiment, Form 10 can be characterized by the differential scanning calorimetry profile (DSC) shown in FIG. 22. The DSC graph plots the heat flow as a function of temperature from a sample, the temperature rate change being about 10° C./min. The profile is characterized by an endothermic transition with an onset temperature of about 139.9° C. with a melt at about 150.9° C. and an endothermic transition with an onset temperature of about 197.3° C. with a melt at about 201.3° C.

In another embodiment, Form 10 can be characterized by thermal gravimetric analysis (TGA) shown in FIG. 22. The TGA profile graphs the percent loss of weight of the sample as a function of temperature, the temperature rate change being about 10° C./min. The weight loss represents a loss of about 0.5% of the weight of the sample as the temperature is changed from about 31.0° C. to 120.0° C.

Form 11

In one embodiment, a single crystalline form, Form 11, of the compound 1 is characterized by the X-ray powder diffraction (XRPD) pattern shown in FIG. 23, and data shown in Table 11A, obtained using CuKa radiation. In a particular embodiment, the polymorph can be characterized by one or more of the peaks taken from FIG. 23, as shown in Table 11A. For example, the polymorph can be characterized by one or two or three or four or five or six or seven or eight or nine or ten or eleven of the peaks shown in Table 11A.

TABLE 11A

| Angle 2-Theta° | Intensity % |
|---|---|
| 6.3 | 53.1 |
| 7.7 | 32.8 |
| 16.3 | 40.2 |
| 17.2 | 16.8 |
| 20.0 | 74.6 |
| 20.2 | 100.0 |
| 20.5 | 79.2 |
| 21.2 | 89.4 |
| 23.2 | 21.4 |
| 26.5 | 56.0 |
| 28.1 | 17.2 |

In another embodiment, Form 11 can be characterized by the peaks identified at 2θ angles of 6.3, 20.0, 20.2, 20.5, 21.2, and 26.5°. In a further embodiment, Form 11 can be characterized by the peaks are identified at 2θ angles of 20.0, 20.2, 20.5, and 21.2°.

In another embodiment, Form 11 can be characterized by the differential scanning calorimetry profile (DSC) shown in FIG. 24. The DSC graph plots the heat flow as a function of temperature from a sample, the temperature rate change being about 10° C./min. The profile is characterized by an endothermic transition with an onset temperature of about 144.3° C. with a melt at about 154.5° C. and an endothermic transition with an onset temperature of about 193.4° C. with a melt at about 201.6° C.

In another embodiment, Form 11 can be characterized by thermal gravimetric analysis (TGA) shown in FIG. 25. The TGA profile graphs the percent loss of weight of the sample as a function of temperature, the temperature rate change being about 10° C./min. The weight loss represents a loss of about 3.0% of the weight of the sample as the temperature is changed from about 25.7° C. to 98.4° C.

Form 12

In one embodiment, a single crystalline form, Form 12, of the compound 1 is characterized by the X-ray powder diffraction (XRPD) pattern shown in FIG. 26, and data shown in Table 12A, obtained using CuKa radiation. In a particular embodiment, the polymorph can be characterized by one or more of the peaks taken from FIG. 26, as shown in Table 12A. For example, the polymorph can be characterized by one or two or three or four or five or six or seven or eight or nine of the peaks shown in Table 12A.

TABLE 12A

| Angle 2-Theta° | Intensity % |
| --- | --- |
| 7.2 | 75.7 |
| 7.4 | 100.0 |
| 8.0 | 61.3 |
| 8.2 | 52.4 |
| 13.2 | 9.4 |
| 16.5 | 27.2 |
| 18.6 | 32.7 |
| 20.2 | 23.6 |
| 20.8 | 18.7 |

In another embodiment, Form 12 can be characterized by the peaks identified at 2θ angles of 7.2, 7.4, 8.0, 8.2, 16.5, and 18.6°. In a further embodiment, Form 12 can be characterized by the peaks are identified at 2θ angles of 7.2, 7.4, 8.0, and 8.2°.

In another embodiment, Form 12 can be characterized by the differential scanning calorimetry profile (DSC) shown in FIG. 27. The DSC graph plots the heat flow as a function of temperature from a sample, the temperature rate change being about 10° C./min. The profile is characterized by an endothermic transition with an onset temperature of about 80.9° C. with a melt at about 106.3° C., an endothermic transition with an onset temperature of about 136.32° C. with a melt at about 150.3° C., and a strong endothermic transition with an onset temperature of about 199.0° C. with a melt at about 203.1° C.

In another embodiment, Form 12 can be characterized by thermal gravimetric analysis (TGA) shown in FIG. 27. The TGA profile graphs the percent loss of weight of the sample as a function of temperature, the temperature rate change being about 10° C./min. The weight loss represents a loss of about 6.4% of the weight of the sample as the temperature is changed from about 25.9° C. to 80.0° C., and a loss of about 7.2% of the weight of the sample as the temperature is changed from about 25.9° C. to 150.0° C.

Form 13

In one embodiment, a single crystalline form, Form 13, of the compound 1 is characterized by the X-ray powder diffraction (XRPD) pattern shown in FIG. 28, and data shown in Table 13A, obtained using CuKa radiation. In a particular embodiment, the polymorph can be characterized by one or more of the peaks taken from FIG. 28, as shown in Table 13A. For example, the polymorph can be characterized by one or two or three or four or five or six or seven or eight or nine of the peaks shown in Table 13A.

TABLE 13A

| Angle 2-Theta° | Intensity % |
| --- | --- |
| 6.3 | 100.0 |
| 12.7 | 30.1 |
| 14.9 | 14.1 |
| 18.0 | 8.4 |
| 19.1 | 10.8 |
| 20.3 | 24.3 |
| 20.8 | 15.2 |
| 22.0 | 7.2 |
| 26.5 | 18.2 |

In another embodiment, Form 13 can be characterized by the peaks identified at 2θ angles of 6.3, 12.7, 20.3, 20.8, and 26.5°. In a further embodiment, Form 13 can be characterized by the peaks are identified at 2θ angles of 6.3, 12.7, and 20.3°.

In another embodiment, Form 13 can be characterized by the differential scanning calorimetry profile (DSC) shown in FIG. 29. The DSC graph plots the heat flow as a function of temperature from a sample, the temperature rate change being about 10° C./min. The profile is characterized by a weak endothermic transition with an onset temperature of about 144.1° C. with a melt at about 152.4° C., and a strong endothermic transition with an onset temperature of about 198.1° C. with a melt at about 204.8° C.

In another embodiment, Form 13 can be characterized by thermal gravimetric analysis (TGA) shown in FIG. 29. The TGA profile graphs the percent loss of weight of the sample as a function of temperature, the temperature rate change being about 10° C./min. The weight loss represents a loss of about 4.1% of the weight of the sample as the temperature is changed from about 24.9° C. to 150.0° C.

Form 14

In one embodiment, a single crystalline form, Form 14, of the compound 1 is characterized by the X-ray powder diffraction (XRPD) pattern shown in FIG. 30, and data shown in Table 14A, obtained using CuKa radiation. In a particular embodiment, the polymorph can be characterized by one or more of the peaks taken from FIG. 30, as shown in Table 14A. For example, the polymorph can be characterized by one or two or three or four or five or six or seven or eight or nine of the peaks shown in Table 14A.

TABLE 14A

| Angle 2-Theta° | Intensity % |
| --- | --- |
| 6.6 | 100.0 |
| 8.7 | 26.9 |
| 10.3 | 6.7 |
| 13.3 | 30.8 |
| 15.1 | 26.5 |
| 17.5 | 49.6 |
| 20.8 | 54.8 |

TABLE 14A-continued

| Angle 2-Theta° | Intensity % |
|---|---|
| 23.3 | 49.1 |
| 26.8 | 33.4 |

In another embodiment, Form 14 can be characterized by the peaks identified at 2θ angles of 6.6, 17.5, 20.8 and 23.3°. In a further embodiment, Form 14 can be characterized by the peaks are identified at 2θ angles of 6.6 and 20.8°.

In another embodiment, Form 14 can be characterized by the differential scanning calorimetry profile (DSC) shown in FIG. 31. The DSC graph plots the heat flow as a function of temperature from a sample, the temperature rate change being about 10° C./min. The profile is characterized by a weak endothermic transition with an onset temperature of about 122.3° C. with a melt at about 134.5° C., and a strong endothermic transition with an onset temperature of about 207.6° C. with a melt at about 211.8° C.

In another embodiment, Form 14 can be characterized by thermal gravimetric analysis (TGA) shown in FIG. 31. The TGA profile graphs the percent loss of weight of the sample as a function of temperature, the temperature rate change being about 10° C./min. The weight loss represents a loss of about 5.71% of the weight of the sample as the temperature is changed from about 28.1° C. to 150.0° C.

Form 15

In one embodiment, a single crystalline form, Form 15, of the compound 1 is characterized by the X-ray powder diffraction (XRPD) pattern shown in FIG. 32, and data shown in Table 15A, obtained using CuKa radiation. In a particular embodiment, the polymorph can be characterized by one or more of the peaks taken from FIG. 32, as shown in Table 15A. For example, the polymorph can be characterized by one or two or three or four or five or six or seven or eight or nine of the peaks shown in Table 15A.

TABLE 15A

| Angle 2-Theta° | Intensity % |
|---|---|
| 6.4 | 100.0 |
| 11.5 | 9.2 |
| 12.9 | 18.0 |
| 19.5 | 8.0 |
| 20.2 | 12.4 |
| 21.6 | 5.0 |
| 23.2 | 10.2 |
| 26.1 | 19.0 |
| 29.4 | 3.2 |

In another embodiment, Form 15 can be characterized by the peaks identified at 2θ angles of 6.4, 12.9, 20.2, and 26.1°. In a further embodiment, Form 15 can be characterized by the peaks are identified at 2θ angles of 6.4, 12.9, and 26.1°.

In another embodiment, Form 15 can be characterized by the differential scanning calorimetry profile (DSC) shown in FIG. 33. The DSC graph plots the heat flow as a function of temperature from a sample, the temperature rate change being about 10° C./min. The profile is characterized by a weak endothermic transition with an onset temperature of about 136.5° C. with a melt at about 140.1° C., and a strong endothermic transition with an onset temperature of about 213.1° C. with a melt at about 215.2° C.

In another embodiment, Form 15 can be characterized by thermal gravimetric analysis (TGA) shown in FIG. 33. The TGA profile graphs the percent loss of weight of the sample as a function of temperature, the temperature rate change being about 10° C./min. The weight loss represents a loss of about 7.6% of the weight of the sample as the temperature is changed from about 28.7° C. to 150.0° C.

Form 16

In one embodiment, a single crystalline form, Form 16, of the compound 3 is characterized by the X-ray powder diffraction (XRPD) pattern shown in FIG. 34, and data shown in Table 16A, obtained using CuKa radiation. In a particular embodiment, the polymorph can be characterized by one or more of the peaks taken from FIG. 34, as shown in Table 16A. For example, the polymorph can be characterized by one or two or three or four or five or six or seven or eight or nine of the peaks shown in Table 16A.

TABLE 16A

| Angle 2-Theta° | Intensity % |
|---|---|
| 6.8 | 35.5 |
| 10.1 | 30.7 |
| 10.6 | 53.1 |
| 13.6 | 46.0 |
| 14.2 | 63.8 |
| 17.2 | 26.4 |
| 18.4 | 34.0 |
| 19.2 | 100.0 |
| 23.5 | 3.8 |

In another embodiment, Form 16 can be characterized by the peaks identified at 2θ angles of 6.8, 10.6, 13.6, 14.2, and 19.2°. In another embodiment, Form 16 can be characterized by the peaks identified at 2θ angles of 10.6, 14.2, and 19.2°.

In another embodiment, Form 16 can be characterized by the differential scanning calorimetry profile (DSC) shown in FIG. 35. The DSC graph plots the heat flow as a function of temperature from a sample, the temperature rate change being about 10° C./min. The profile is characterized by a strong endothermic transition with an onset temperature of about 169.7° C. with a melt at about 172.1° C.

In another embodiment, Form 16 can be characterized by thermal gravimetric analysis (TGA) shown in FIG. 36. The TGA profile graphs the percent loss of weight of the sample as a function of temperature, the temperature rate change being about 10° C./min. The weight loss represents a loss of about 0.1% of the weight of the sample as the temperature is changed from about 23.9° C. to 150.0° C.

Form 17

In one embodiment, a single crystalline form, Form 17, of the compound 3 is characterized by the X-ray powder diffraction (XRPD) pattern shown in FIG. 37, and data shown in Table 17A, obtained using CuKa radiation. In a particular embodiment, the polymorph can be characterized by one or more of the peaks taken from FIG. 37, as shown in Table 17A. For example, the polymorph can be characterized by one or two or three or four or five or six or seven or eight or nine of the peaks shown in Table 17A.

TABLE 17A

| Angle 2-Theta° | Intensity % |
|---|---|
| 7.2 | 53.3 |
| 10.1 | 26.7 |
| 11.5 | 20.5 |
| 13.6 | 100.0 |
| 18.5 | 72.0 |

TABLE 17A-continued

| Angle 2-Theta° | Intensity % |
|---|---|
| 19.3 | 46.9 |
| 20.3 | 39.4 |
| 21.9 | 55.4 |
| 23.5 | 77.5 |

In another embodiment, Form 17 can be characterized by the peaks identified at 2θ angles of 7.2, 13.6, 18.5, 19.3, 21.9, and 23.5°. In another embodiment, Form 17 can be characterized by the peaks identified at 2θ angles of 13.6, 18.5, and 23.5°.

Form 18

In one embodiment, a single crystalline form, Form 18, of the compound 3 is characterized by the X-ray powder diffraction (XRPD) pattern shown in FIG. 38, and data shown in Table 18A, obtained using CuKa radiation. In a particular embodiment, the polymorph can be characterized by one or more of the peaks taken from FIG. 38, as shown in Table 18A. For example, the polymorph can be characterized by one or two or three or four or five or six or seven or eight or nine of the peaks shown in Table 18A.

TABLE 18A

| Angle 2-Theta° | Intensity % |
|---|---|
| 6.4 | 45.4 |
| 8.4 | 84.0 |
| 9.8 | 100.0 |
| 16.1 | 26.0 |
| 16.9 | 22.7 |
| 17.8 | 43.6 |
| 19.7 | 40.4 |
| 21.1 | 20.5 |
| 26.1 | 15.9 |

In another embodiment, Form 18 can be characterized by the peaks identified at 2θ angles of 6.4, 8.4, 9.8, 17.8, and 19.7°. In another embodiment, Form 18 can be characterized by the peaks identified at 2θ angles of 8.4 and 9.8°.

Form 19

In one embodiment, a single crystalline form, Form 19, of the compound 3 is characterized by the X-ray powder diffraction (XRPD) pattern shown in FIG. 39, and data shown in Table 19A, obtained using CuKa radiation. In a particular embodiment, the polymorph can be characterized by one or more of the peaks taken from FIG. 39, as shown in Table 19A. For example, the polymorph can be characterized by one or two or three or four or five or six or seven or eight of the peaks shown in Table 19A.

TABLE 19A

| Angle 2-Theta° | Intensity % |
|---|---|
| 8.1 | 97.9 |
| 11.4 | 24.9 |
| 14.1 | 51.5 |
| 15.2 | 28.4 |
| 16.4 | 85.0 |
| 17.3 | 100.0 |
| 20.5 | 54.7 |
| 24.1 | 88.7 |

In another embodiment, Form 19 can be characterized by the peaks identified at 2θ angles of 8.1, 14.1, 16.4, 17.3, 20.5, and 24.1°. In another embodiment, Form 19 can be characterized by the peaks identified at 2θ angles of 8.1, 16.4, 17.3, and 24.1°.

Form 20

In one embodiment, a single crystalline form, Form 20, of the compound 1 is characterized by the X-ray powder diffraction (XRPD) pattern shown in FIG. 40, obtained using CuKa radiation. In a particular embodiment, the polymorph can be characterized by one or more of the peaks taken from FIG. 40.

In another embodiment, Form 20 can be characterized by thermal gravimetric analysis (TGA) shown in FIG. 41. The TGA profile graphs the percent loss of weight of the sample as a function of temperature, the temperature rate change being about 10° C./min.

In another embodiment, Form 20 is characterized by a DVS profile substantially similar to FIG. 42.

Form 21

In one embodiment, a single crystalline form, Form 21, of the compound 1 is characterized by the X-ray powder diffraction (XRPD) pattern shown in FIG. 43, obtained using CuKa radiation. In a particular embodiment, the polymorph can be characterized by one or more of the peaks taken from FIG. 43. For example, the polymorph can be characterized by one or two or three or four or five or six or seven or eight or nine of the peaks.

In another embodiment, Form 21 can be characterized by the differential scanning calorimetry profile (DSC) shown in FIG. 45. The DSC graph plots the heat flow as a function of temperature from a sample, the temperature rate change being about 10° C./min.

In another embodiment, Form 21 can be characterized by thermal gravimetric analysis (TGA) shown in FIG. 44. The TGA profile graphs the percent loss of weight of the sample as a function of temperature, the temperature rate change being about 10° C./min.

In another embodiment, Form 21 is characterized by a DVS profile substantially similar to FIG. 46.

Other embodiments are directed to a single crystalline form of compound 1 or compound 3 characterized by a combination of the aforementioned characteristics of any of the single crystalline forms discussed herein. The characterization may be by any combination of one or more of the XRPD, TGA, DSC, and DVS described for a particular polymorph. For example, the single crystalline form of compound 1 or compound 3 may be characterized by any combination of the XRPD results regarding the position of the major peaks in a XRPD scan; and/or any combination of one or more of parameters derived from data obtained from a XRPD scan. The single crystalline form of compound 1 or compound 3 may also be characterized by TGA determinations of the weight loss associated with a sample over a designated temperature range; and/or the temperature at which a particular weight loss transition begins. DSC determinations of the temperature associated with the maximum heat flow during a heat flow transition and/or the temperature at which a sample begins to undergo a heat flow transition may also characterize the crystalline form. Weight change in a sample and/or change in sorption/desorption of water per molecule of compound 1 or compound 3 as determined by water sorption/desorption measurements over a range of relative humidity (e.g., 0% to 90%) may also characterize a single crystalline form of compound 1 or compound 3.

The combinations of characterizations that are discussed above may be used to describe any of the polymorphs of compound 1 or compound 3 discussed herein, or any combination of these polymorphs.

EXAMPLES

Abbreviations
ca approximately
$CHCl_3$—chloroform
DCM—dichloromethane
DMF—dimethylformamide
$Et_2O$—diethyl ether
EtOH—ethyl alcohol
EtOAc—ethyl acetate
MeOH—methyl alcohol
MeCN—acetonitrile
PE—petroleum ether
THF—tetrahydrofuran
AcOH—acetic acid
HCl—hydrochloric acid
$H_2SO_4$—sulfuric acid
$NH_4Cl$—ammonium chloride
KOH—potassium hydroxide
NaOH—sodium hydroxide
$Na_2CO_3$—sodium carbonate
TFA—trifluoroacetic acid
$NaHCO_3$—sodium bicarbonate
DMSO dimethylsulfoxide
DSC differential scanning calorimetry
DVS dynamic vapor sorption
GC gas chromatography
h hours
HPLC high performance liquid chromatography
min minutes
m/z mass to charge
MS mass spectrum
NMR nuclear magnetic resonance
RT room temperature
TGA thermal gravimetric analysis
XRPD X-ray powder diffraction/X-ray powder diffractogram/X-ray powder diffractometer General Methods In the following examples, reagents may be purchased from commercial sources (including Alfa, Acros, Sigma Aldrich, TCI and Shanghai Chemical Reagent Company), and used without further purification. Nuclear magnetic resonance (NMR) spectra may be obtained on a Brucker AMX-400 NMR (Brucker, Switzerland). Chemical shifts are reported in parts per million (ppm, δ) downfield from tetramethylsilane. Mass spectra may be run with electrospray ionization (ESI) from a Waters LCT TOF Mass Spectrometer (Waters, USA).

For exemplary compounds, including crystalline forms thereof, disclosed in this section, the specification of a stereoisomer (e.g., an (R) or (S) stereoisomer) indicates a preparation of that compound such that the compound is enriched at the specified stereocenter by at least about 90%, 95%, 96%, 97%, 98%, or 99%.

The chemical name of each of the exemplary compound described below is generated by ChemDraw software.

X-Ray Powder Diffraction (XRPD) parameters: XRPD analysis was performed using a PANalytical Empyrean X-ray powder diffractometer (XRPD) with a 12-auto sample stage. The XRPD parameters used are listed in Table 20.

TABLE 20

| | Parameters for Reflection Mode |
|---|---|
| X-Ray wavelength | Cu, kα, |
| | Kα1 (Å): 1.540598, Kα2 (Å): 1.544426 |
| | Kα2/Kα1 intensity ratio: 0.50 |
| X-Ray tube setting | 45 kV, 40 mA |
| Divergence slit | Automatic |
| Scan mode | Continuous |
| Scan range (°2TH) | 3°-40° |
| Step size (°2TH) | 0.0170 |
| Scan speed (°/min) | About 10 |

For Form 3, XRPD analysis was performed using a LYNXEYE XE Detector (Bruker). The XRPD parameters used are listed in Table 21.

TABLE 21

| | Parameters for Reflection Mode |
|---|---|
| X-Ray wavelength | Cu, kα, |
| | Kα1 (Å): 1.54060, Kα2 (Å): 1.54439 |
| | Kα2/Kα1 intensity ratio: 0.50 |
| Scan range (°2TH) | 3°-40° |
| Step size (°2TH) | 0.012 |

Differential Scanning calorimetry (DSC) parameters: DSC analysis was performed using a TA Q100, or Q200/Q2000 DSC from TA Instruments. The temperature was ramped from room temperature to the desired temperature at a heating rate of 10° C./min using $N_2$ as the purge gas, with pan crimped.

Thermogravimetric Analysis (TGA) parameters: TGA analysis was performed using a TA Q500/Q5000 TGA from TA Instruments. The temperature was ramped from room temperature to the desired temperature at a heating rate of 10° C./min or 20° C./min using $N_2$ as the purge gas.

Dynamic Vapor Sorption (DVS) parameters: DVS was measured via a SMS (Surface Measurement Systems) DVS Intrinsic. The relative humidity at 25° C. were calibrated against deliquescence point of LiCl, $Mg(NO_3)_2$ and KCl. The DVS Parameters used are listed in Table 22.

TABLE 22

| | DVS |
|---|---|
| Temperature | 25° C. |
| Sample size | 10-20 mg |
| Gas and flow rate | $N_2$, 200 mL/min |
| dm/dt | 0.002%/min |
| Min. dm/dt stability duration | 10 min |
| Max. equilibrium time | 180 min |
| RH range | 60% RH-95% RH-0% RH-95% RH |
| RH step size | 10% (0% RH-90% RH, 90% RH--0% RH) |
| | 5% (90% RH-95% RH-90% RH) |

Example 1

Synthesis of Compound 3

Example 1

Step 1: preparation of 6-trifluoromethyl-pyridine-2-carboxylic acid

Diethyl ether (4.32 L) and hexanes (5.40 L) are added to the reaction vessel under $N_2$ atmosphere, and cooled to −75° C. to −65° C. Dropwise addition of n-Butyl lithium (3.78 L in 1.6 M hexane) under N₂ atmosphere at below −65° C. is followed by dropwise addition of dimethyl amino ethanol (327.45 g, 3.67 mol) and after 10 min. dropwise addition of 2-trifluoromethyl pyridine (360 g, 2.45 mol). The reaction is stirred under N₂ while maintaining the temperature below ϴ65° C. for about 2.0-2.5 hrs. The reaction mixture is poured over crushed dry ice under N₂, then brought to a temperature of 0 to 5° C. while stirring (approx. 1.0 to 1.5 h) followed by the addition of water (1.8 L). The reaction mixture is stirred for 5-10 mins and allowed to warm to 5-10° C. 6N HCl (900 mL) is added dropwise until the mixture reached pH 1.0 to 2.0, then the mixture is stirred for 10-20 min. at 5-10° C. The reaction mixture is diluted with ethyl acetate at 25-35° C., then washed with brine solution. The reaction is concentrated and rinsed with n-heptane and then dried to yield 6-trifluoromethyl-pyridine-2-carboxylic acid.

Example 1

Step 2: preparation of 6-trifluoromethyl-pyridine-2-carboxylic acid methyl ester Methanol is added to the reaction vessel under nitrogen atmosphere. 6-trifluoromethyl-pyridine-2-carboxylic acid (150 g, 0.785 mol) is added and dissolved at ambient temperature. Acetyl chloride (67.78 g, 0.863 mol) is added dropwise at a temperature below 45° C. The reaction mixture is maintained at 65-70° C. for about 2-2.5 h, and then concentrated at 35-45° C. under vacuum and cooled to 25-35° C. The mixture is diluted with ethyl acetate and rinsed with saturated NaHCO₃ solution then rinsed with brine solution. The mixture is concentrated at temp 35-45° C. under vacuum and cooled to 25-35° C., then rinsed with n-heptane and concentrated at temp 35-45° C. under vacuum, then degassed to obtain brown solid, which is rinsed with n-heptane and stirred for 10-15 minute at 25-35° C. The suspension is cooled to −40 to −30° C. while stirring, and filtered and dried to provide 6-trifluoromethyl-pyridine-2-carboxylic acid methyl ester.

Example 1

Step 3: preparation of 6-(6-Trifluoromethyl-pyridin-2-yl)-1H-1,3,5-triazine-2,4-dione 1 L absolute ethanol is charged to the reaction vessel under N₂ atmosphere and Sodium Metal (11.2 g, 0.488 mol) is added in portions under N₂ atmosphere at below 50° C. The reaction is stirred for 5-10 minutes, then heated to 50-55° C. Dried Biuret (12.5 g, 0.122 mol) is added to the reaction vessel under N₂ atmosphere at 50-55° C. temperature, and stirred 10-15 minutes. While maintaining 50-55° C. 6-trifluoromethyl-pyridine-2-carboxylic acid methyl ester (50.0 g, 0.244 mol) is added. The reaction mixture is heated to reflux (75-80° C.) and maintained for 1.5-2 hours. Then cooled to 35-40° C., and concentrated at 45-50° C. under vacuum. Water is added and the mixture is concentrated under vacuum then cooled to 35-40° C. more water is added and the mixture cooled to 0-5° C. pH is adjusted to 7-8 by slow addition of 6N HCl, and solid precipitated out and is centrifuged and rinsed with water and centrifuged again. The off white to light brown solid of 6-(6-Trifluoromethyl-pyridin-2-yl)-1H-1,3,5-triazine-2,4-dione is dried under vacuum for 8 to 10 hrs at 50° C. to 60° C. under 600 mm/Hg pressure to provide 6-(6-Trifluoromethyl-pyridin-2-yl)-1H-1,3,5-triazine-2,4-dione.

Example 1

Step 4: preparation of 2, 4-Dichloro-6-(6-trifluoromethyl-pyridin-2-yl)-1,3,5-triazine POCl₃ (175.0 mL) is charged into the reaction vessel at 20-35° C., and 6-(6-Trifluoromethyl-pyridin-2-yl)-1H-1,3,5-triazine-2,4-dione (35.0 g, 0.1355 mol) is added in portions at below 50° C. The reaction mixture is de-gassed 5-20 minutes by purging with N₂ gas. Phosphorous pentachloride (112.86 g, 0.542 mol) is added while stirring at below 50° C. and the resulting slurry is heated to reflux (105-110° C.) and maintained for 3-4 h. The reaction mixture is cooled to 50-55° C., and concentrated at below 55° C. then cooled to 20-30° C. The reaction mixture is rinsed with ethyl acetate and the ethyl acetate layer is slowly added to cold water (temperature ~5° C.) while stirring and maintaining the temperature below 10° C. The mixture is stirred 3-5 minutes at a temperature of between 10 to 20° C. and the ethyl acetate layer is collected. The reaction mixture is rinsed with sodium bicarbonate solution and dried over anhydrous sodium sulphate. The material is dried 2-3 h under vacuum at below 45° C. to provide 2, 4-Dichloro-6-(6-trifluoromethyl-pyridin-2-yl)-1,3,5-triazine.

Example 1

Step 5: preparation of 4-chloro-6-(6-(trifluoromethyl)pyridin-2-yl)-N-(2-(trifluoro-methyl)-pyridin-4-yl)-1,3,5-triazin-2-amine A mixture of THF (135 mL) and 2,4-Dichloro-6-(6-trifluoromethyl-pyridin-2-yl)-1,3,5-triazine (27.0 g, 0.0915 mol) are added to the reaction vessel at 20-35° C., then 4-amino-2-(trifluoromethyl)pyridine (16.31 g, 0.1006 mol) and sodium bicarbonate (11.52 g, 0.1372 mol) are added. The resulting slurry is heated to reflux (75-80° C.) for 20-24 h. The reaction is cooled to 30-40° C. and THF evaporated at below 45° C. under reduced pressure. The reaction mixture is cooled to 20-35° C. and rinsed with ethyl acetate and water, and the ethyl acetate layer collected and rinsed with 0.5 N HCl and brine solution. The organic layer is concentrated under vacuum at below 45° C. then rinsed with dichloromethane and hexanes, filtered and washed with hexanes and dried for 5-6 h at 45-50° C. under vacuum to provide 4-chloro-6-(6-(trifluoromethyl)pyridin-2-yl)-N-(2-(trifluoro-methyl)-pyridin-4-yl)-1,3,5-triazin-2-amine.

Example 1

Step 6: preparation of 2-methyl-1-(4-(6-(trifluoromethyl)pyridin-2-yl)-6-(2-(trifluoromethyl)-pyridin-4-ylamino)-1,3,5-triazin-2-ylamino)propan-2-ol THF (290 mL), 4-chloro-6-(6-(trifluoromethyl)pyridin-2-yl)-N-(2-(trifluoro-methyl)-pyridin-4-yl)-1,3,5-triazin-2-amine (29.0 g, 0.06893 mol), sodium bicarbonate (8.68 g, 0.1033 mol), and 1,1-dimethylaminoethanol (7.37 g, 0.08271 mol) are added to the reaction vessel at 20-35° C. The resulting slurry is heated to reflux (75-80° C.) for 16-20 h. The reaction is cooled to 30-40° C. and THF evaporated at below 45° C. under reduced pressure. The reaction mixture is cooled to 20-35° C. and rinsed with ethyl acetate and water, and the ethyl acetate layer collected. The organic layer is concentrated under vacuum at below 45° C. then rinsed with dichloromethane and hexanes, filtered and washed with hexanes and dried for 8-10 h at 45-50° C. under vacuum to provide 2-methyl-1-(4-(6-(trifluoromethyl)pyridin-2-yl)-6-(2-(trifluoromethyl)-pyridin-4-ylamino)-1,3,5-triazin-2-ylamino)propan-2-ol.

Example 2

Synthesis of Compound 1

Acetone (435.0 mL) and compound 3 (87.0 g, 0.184 mol) are added to the reaction vessel at 20-35° C. In a separate vessel, methanesulfonic acid is added over 10 minutes to cold (0-4° C.) acetone (191.4 mL) while stirring to prepare a methane sulfonic acid solution. While passing through a micron filter, the freshly prepared methanesulfonic acid solution is added dropwise to the reaction mixture. The resulting slurry is filtered using nutsche filter and washed with acetone. The filtered material is dried for 30-40 minutes using vacuum to provide compound 1.

Example 2A

Synthesis of Compound 3 Form 16

Example 2A

Step 1: preparation of 6-trifluoromethyl-pyridine-2-carboxylic acid

Diethyl ether (4.32 L) and hexanes (5.40 L) are added to the reaction vessel under $N_2$ atmosphere, and cooled to −75° C. to −65° C. Dropwise addition of n-Butyl lithium (3.78 L in 1.6 M hexane) under $N_2$ atmosphere at below −65° C. is followed by dropwise addition of dimethyl amino ethanol (327.45 g, 3.67 mol) and after 10 min. dropwise addition of 2-trifluoromethyl pyridine (360 g, 2.45 mol). The reaction is stirred under $N_2$ while maintaining the temperature below −65° C. for about 2.0-2.5 hrs. The reaction mixture is poured over crushed dry ice under $N_2$, then brought to a temperature of 0 to 5° C. while stirring (approx. 1.0 to 1.5 h) followed by the addition of water (1.8 L). The reaction mixture is stirred for 5-10 mins and allowed to warm to 5-10° C. 6N HCl (900 mL) is added dropwise until the mixture reached pH 1.0 to 2.0, then the mixture is stirred for 10-20 min. at 5-10° C. The reaction mixture is diluted with ethyl acetate at 25-35° C., then washed with brine solution. The reaction is concentrated and rinsed with n-heptane and then dried to yield 6-trifluoromethyl-pyridine-2-carboxylic acid.

Example 2A

Step 2: preparation of 6-trifluoromethyl-pyridine-2-carboxylic acid methyl ester Methanol is added to the reaction vessel under nitrogen atmosphere. 6-trifluoromethyl-pyridine-2-carboxylic acid (150 g, 0.785 mol) is added and dissolved at ambient temperature. Acetyl chloride (67.78 g, 0.863 mol) is added dropwise at a temperature below 45° C. The reaction mixture is maintained at 65-70° C. for about 2-2.5 h, and then concentrated at 35-45° C. under vacuum and cooled to 25-35° C. The mixture is diluted with ethyl acetate and rinsed with saturated $NaHCO_3$ solution then rinsed with brine solution. The mixture is concentrated at temp 35-45° C. under vacuum and cooled to 25-35° C., then rinsed with n-heptane and concentrated at temp 35-45° C. under vacuum, then degassed to obtain brown solid, which is rinsed with n-heptane and stirred for 10-15 minute at 25-35° C. The suspension is cooled to −40 to −30° C. while stirring, and filtered and dried to provide 6-trifluoromethyl-pyridine-2-carboxylic acid methyl ester.

Example 2A

Step 3: preparation of 6-(6-Trifluoromethyl-pyridin-2-yl)-1H-1,3,5-triazine-2,4-dione 1 L absolute ethanol is charged to the reaction vessel under $N_2$ atmosphere and Sodium Metal (11.2 g, 0.488 mol) is added in portions under $N_2$ atmosphere at below 50° C. The reaction is stirred for 5-10 minutes, then heated to 50-55° C. Dried Biuret (12.5 g, 0.122 mol) is added to the reaction vessel under $N_2$ atmosphere at 50-55° C. temperature, and stirred 10-15 minutes. While maintaining 50-55° C. 6-trifluoromethyl-pyridine-2-carboxylic acid methyl ester (50.0 g, 0.244 mol) is added. The reaction mixture is heated to reflux (75-80° C.) and maintained for 1.5-2 hours. Then cooled to 35-40° C., and concentrated at 45-50° C. under vacuum. Water is added and the mixture is concentrated under vacuum then cooled to 35-40° C. more water is added and the mixture cooled to 0-5° C. pH is adjusted to 7-8 by slow addition of 6N HCl, and solid precipitated out and is centrifuged and rinsed with water and centrifuged again. The off white to light brown solid of 6-(6-Trifluoromethyl-pyridin-2-yl)-1H-1,3,5-triazine-2,4-dione is dried under vacuum for 8 to 10 hrs at 50° C. to 60° C. under 600mm/Hg pressure to provide 6-(6-Trifluoromethyl-pyridin-2-yl)-1H-1,3,5-triazine-2,4-dione.

Example 2A

Step 4: preparation of 2, 4-Dichloro-6-(6-trifluoromethyl-pyridin-2-yl)-1,3,5-triazine $POCl_3$ (175.0 mL) is charged into the reaction vessel at 20-35° C., and 6-(6-Trifluoromethyl-pyridin-2-yl)-1H-1,3,5-triazine-2,4-dione (35.0 g, 0.1355 mol) is added in portions at below 50° C. The reaction mixture is de-gassed 5-20 minutes by purging with $N_2$ gas. Phosphorous pentachloride (112.86 g, 0.542 mol) is added while stirring at below 50° C. and the resulting slurry is heated to reflux (105-110° C.) and maintained for 3-4 h. The reaction mixture is cooled to 50-55° C., and concentrated at below 55° C. then cooled to 20-30° C. The reaction mixture is rinsed with ethyl acetate and the ethyl acetate layer is slowly added to cold water (temperature ~5° C.) while stirring and maintaining the temperature below 10° C. The mixture is stirred 3-5 minutes at a temperature of between 10 to 20° C. and the ethyl acetate layer is collected. The reaction mixture is rinsed with sodium bicarbonate solution and dried over anhydrous sodium sulphate. The material is dried 2-3 h under vacuum at below 45° C. to provide 2, 4-Dichloro-6-(6-trifluoromethyl-pyridin-2-yl)-1,3,5-triazine.

Example 2A

Step 5: preparation of 4-chloro-6-(6-(trifluoromethyl)pyridin-2-yl)-N-(2-(trifluoro-methyl)-pyridin-4-yl)-1,3,5-triazin-2-amine A mixture of THF (135 mL) and 2, 4-Dichloro-6-(6-trifluoromethyl-pyridin-2-yl)-1,3,5-triazine (27.0 g, 0.0915 mol) are added to the reaction vessel at 20-35° C., then 4-amino-2-(trifluoromethyl)pyridine (16.31 g, 0.1006 mol)

and sodium bicarbonate (11.52 g, 0.1372 mol) are added. The resulting slurry is heated to reflux (75-80° C.) for 20-24 h. The reaction is cooled to 30-40° C. and THF evaporated at below 45° C. under reduced pressure. The reaction mixture is cooled to 20-35° C. and rinsed with ethyl acetate and water, and the ethyl acetate layer collected and rinsed with 0.5 N HCl and brine solution. The organic layer is concentrated under vacuum at below 45° C. then rinsed with dichloromethane and hexanes, filtered and washed with hexanes and dried for 5-6 h at 45-50° C. under vacuum to provide 4-chloro-6-(6-(trifluoromethyl)pyridin-2-yl)-N-(2-(trifluoro-methyl)-pyridin-4-yl)-1,3,5-triazin-2-amine.

Example 2A

Step 6: preparation of2-methyl-1-(4-(6-(trifluoromethyl)pyridin-2-yl)-6-(2-(trifluoromethyl)-pyridin-4-ylamino)-1,3,5-triazin-2-ylamino)propan-2-ol compound 3

THF (290 mL), 4-chloro-6-(6-(trifluoromethyl)pyridin-2-yl)-N-(2-(trifluoro-methyl)-pyridin-4-yl)-1,3,5-triazin-2-amine (29.0 g, 0.06893 mol), sodium bicarbonate (8.68 g, 0.1033 mol), and 1,1-dimethylaminoethanol (7.37 g, 0.08271 mol) are added to the reaction vessel at 20-35° C. The resulting slurry is heated to reflux (75-80° C.) for 16-20 h. The reaction is cooled to 30-40° C. and THF evaporated at below 45° C. under reduced pressure. The reaction mixture is cooled to 20-35° C. and rinsed with ethyl acetate and water, and the ethyl acetate layer collected. The organic layer is concentrated under vacuum at below 45° C. then rinsed with dichloromethane and hexanes, filtered and washed with hexanes and dried for 8-10 h at 45-50° C. under vacuum to provide 2-methyl-1-(4-(6-(trifluoromethyl)pyridin-2-yl)-6-(2-(trifluoromethyl)-pyridin-4-ylamino)-1,3,5-triazin-2-ylamino)propan-2-ol.

Example 3A

Synthesis of Compound 3 Form 1

Method A:
Slurry conversion is conducted by suspending ca 10 mg of Form 3 in 0.5-1.0 mL of water. After the suspension is stirred at 50° C. for 48 h, the remaining solids are centrifuged to provide Form 1.

Method B:
9.61 mg of Form 3 is dissolved in 0.2 mL of ethanol. The solution is placed at ambient condition and ethanol is evaporated to get Form 1.

Method C:
6.93 mg of Form 3 is dissolved in 0.2 mL of isopropyl acetate. The solution is placed at ambient temperature and isopropyl acetate is evaporated to get Form 1.

Example 4A

Synthesis of Compound 3 Form 2

Method A:
Slurry conversion is conducted by suspending ca 10 mg of Form 3 in 0.5-1.0 mL of water. After the suspension is stirred at RT for 48 h, the remaining solids are centrifuged to provide Form 2.

Method B:
6.07 mg of Form 3 is suspended in 1.0 mL of water. The suspension is stirred at room temperature for about 24 hours. The solid is isolated to obtain Form 2.

Example 6A

Synthesis of Compound 1 Form 3

While stirring, acetone (961.1 ml) is added to reaction vessel. The reaction is agitated and cooled to 15° C. then methanesulfonic acid (28.3 g) is added and the reaction is aged for at least 10 minutes. Crystallization to Form 3 is accomplished via the following salt formation: 1) acetone (500 ml, 4.17 vol) is charged to the crystallizer, then the mixture is agitated (550 rpm) for 10 min., 2) compound 3 (120.0 g, 253.5 mmol) is charged into crystallizer via solid charger over 45 min., 3) the solid charger is rinsed with acetone (100 ml, 0.83 vol), 4) the reaction is stirred (550 rpm) and heated to 35° C. to obtain a clear solution (in 10 min), 5) a first portion (2%) of MSA/acetone solution (0.3 mol/L, 18.1 ml, 3.8 ml/min) is added over 5 min via a piston pump, then the pump pipeline is washed with acetone (5 ml, 0.04 vol), 6) the mixture is aged at 35° C. for 10 to15 min, while ensuring the solution remains clear, 7) compound 1 seed (2.4 g as generated in Example 5, 2 wt %) is added, to the clear solution, 8) a second portion (49%) of MSA/acetone solution (0.3 mom/L, 444 ml, 3.7 ml/min) is added over 2 hrs, 9) the mixture is aged at 35° C. for 30 min, 10) a third portion (49%) of MSA/acetone solution (0.3 mom/L, 444 ml, 7.4 ml/min) is added over 1 hr, 11) the mixture is aged at 35° C. for 2 hr, 12) the mixture is cooled to 20° C. for 1 hr, 13) the mixture is filtered and the cake washed with acetone (240 ml twice), 17) and dried under vacuum at 30° C.; to provide Form 3 crystals.

Example 7A

Synthesis of Compound 1 Form 4

Reactive crystallization is conducted by mixing compound 3 (0.1 mol/L) and methanesulfonic acid (0.1 mol/L) in MeCN to provide Form 4.

Example 8A

Synthesis of Compound 1 Form 5

Reactive crystallization is conducted by mixing compound 3 (0.1 mol/L) and methanesulfonic acid (0.1 mol/L) in isopropyl alcohol to provide Form 5.

Example 9A

Synthesis of Compound 1 Form 6

Slow evaporation is performed by dissolving ca 10 mg of Form 3 in 0.4-3.0 mL of solvent in a 3-mL glass vial. The vials are covered with foil with about 6 to 8 holes and the visually clear solutions are subjected to slow evaporation at RT to induce precipitation. Then the solids are isolated. Form 6 is provided when the solvent or solvent mixture is MeOH, EtOH, IPA, THF, MeOH/Toluene=3:1, MeOH/CAN=3:1, MeOH/IPAc=3:1, MeOH/H$_2$O=3:1, EtOH/Acetone=5:1, EtOH/DCM=5:1, MeOH/Dioxane=3:1, MeOH/MTBE=3:1, EtOH/Acetone=1:1, and THF/H$_2$O=3:1.

Example 10A

Synthesis of Compound 1 Form 7

Reactive crystallization is conducted by quickly adding methanesulfonic acid (0.1 mol/L) to compound 3 (0.1 mol/L) in acetone or MeCN to provide Form 7.

Example 11A

Synthesis of Compound 1 Form 8

Method A
Methanesulfonic acid (0.1 mol/L) is quickly added to compound 3 (0.1 mol/L) in acetone to provide Form 8.
Method B
Form 12 is heated to 155° C. in TGA and cooled to RT to provide Form 8.

Example 12A

Synthesis of Compound 1 Form 9 compound 3 (0.1 mol/L) and methanesulfonic acid (0.1 mol/L) is mixed in acetone, and Form 9 immediately precipitates out of solution.

Example 13A

Synthesis of Compound 1 Form 10

Form 10 is produced by either heating Form 12 to 80° C. at 10° C./min or keeping Form 12 under $N_2$ sweeping condition for 1 h in TGA.

Example 14A

Synthesis of Compound 1 Form 11

Form 11 is obtained by heating Form 6 to 80° C. or heating Form 13 to 100° C. in the XRPD.

Example 15A

Synthesis of Compound 1 Form 12

Method A
Slow cooling is conducted by dissolving ca 10 mg of Form 3 in 0.3-1.0 mL solvent or solvent mixture at 60° C. Suspensions are filtered at 60° C. and the filtrate is collected. The saturated solution is cooled from 60° C. to 5° C. in an incubator at a rate of 0.05° C./min. If no precipitation is observed, the solution is subjected to evaporation at RT to induce precipitation. The solids are isolated to provide Form 12 when the solvent or solvent mixture is MeOH/$H_2O$=3:1, n-PrOH/$H_2O$=3:1, or THF/MTBE=3:1.
Method B
Solution vapor diffusion is conducted in solvents at RT by dissolving ca 10 mg of Form 3 in MeOH to obtain a clear solution in a 3-mL vial. The vial is sealed into a 20-mL vial filled with ca 3 mL water, and kept at RT for 5 to 7 days, allowing sufficient time to precipitate. The solids are separated to provide Form 12.

Example 16A

Synthesis of Compound 1 Form 13

Method A:
Form 13 is obtained by heating Form 6 to 80° C. and cooling to RT.
Method B:
Slurry conversion is conducted starting from mixtures of Form 6 and Form 12 at water activity of 0.31 at RT.

Example 17A

Synthesis of Compound 1 Form 14

Solution vapor diffusion is conducted in solvents at RT by dissolving ca 10 mg of Form 3 in MeOH to obtain a clear solution in a 3-mL vial. The vial is sealed into a 20-mL vial filled with ca 3 mL heptane, and kept at RT for 5 to 7 days, allowing sufficient time to precipitate. The solids are separated to provide Form 14.

Example 18A

Synthesis of Compound 1 Form 15

Solution vapor diffusion is conducted in solvents at RT by dissolving ca 10 mg of Form 3 in EtOH to obtain a clear solution in a 3-mL vial. The vial is sealed into a 20-mL vial filled with ca 3 mL IPAc or MTBE, and kept at RT for 5 to 7 days, allowing sufficient time to precipitate. The solids are separated to provide Form 15.

Example 20A

Synthesis of Compound 3 Form 17

Method A:
10.26 mg of Form 16 is suspended in 0.4 mL heptane. The suspension is stirred at RT for about 24 hours. The solid is isolated to obtain Form 17.
Method B: 10.10 mg of Form 16 is suspended in 0.2 mL methyl tert-butyl ether. The suspension is stirred at RT for about 24 hours. The solid is isolated to obtain Form 17.

Example 21A

Synthesis of Compound 3 Form 18

8.17 mg of Form 16 is dissolved in 0.2 mL MeOH. The solution is kept at ambient RT and MeOH is evaporated to provide Form 18.

Example 22A

Synthesis of Compound 3 Form 19

905.61 mg of Form 16 is suspended in 5.0 mL of water. The suspension is stirred at RT for about 4 hours, and the solid is isolated to provide Form 19.

In Examples 3, 4, and 5 below, compound 1 may be amorphous, or a mixture of crystalline forms, or a single crystalline form.

Example 23A

Synthesis of Compound 1 Form 20

100 mg of compound 1 was suspended in 3 ml of EtOH/1PrOH 1:1 and stirred at 60° C. The hot suspension was filtered and poured into 15 ml of n-heptane (5° C.). The resulting suspension was stirred for 2 min and then the precipitate was filtered off and dried in air (5 min). NMR confirmed the product contained methanesulfonic acid and traces of the solvents. Drying did not induce any change in form. Form 20 may enclose easily various solvents without influence on the crystal structure.

Example 24A

Synthesis of Compound 1 Form 21

100 mg of compound 1 was dissolved in 2.5 ml of AcOH. The solvent was evaporated at r.t. under gentle $N_2$ flow (no flow control). NMR confirmed that the product, Form 21, was compound 1. TG-FTIR revealed Form 21 likely to be an AcOH solvate. (TG-FTIR: mass loss 7.6%). The DSC showed a first melting peak at 142° C., recrystallization at 149° C. and a broad second melting peak at 188°.

Example 3

In Vitro Experiments

In this Example 3, the dose strengths of compound 1 are intended to reflect the free-base equivalent strengths.

Compound 1 or Compound 3 Reduces Intracellular and Extracellular Levels of 2-HG in a Dose-Dependent Manner TF-1/IDH2 (R140Q) mutant cells are treated in vitro for 7 days with vehicle (dimethylsulfoxide; DMSO) or increasing levels of compound 1 or compound 3 (at concentrations of 1.6 to 5000 nM). The intracellular levels of 2-HG are reduced in the mutant cell line (from 15.5 mM with DMSO to 0.08 mM with 5 µM compound 1 or compound 3) and the reduction is concentration-dependent. With this dose titration, the intracellular $IC_{50}$ for 2-HG inhibition is calculated as 16 nM and the inhibitory concentration, 90% ($IC_{90}$) is 160 nM.

Compound 1 or Compound 3 Reduces Vimentin Levels Associated with Elevated Levels of 2-HG, Indicating a Reduction in Immature (Undifferentiated) Cell Lines Following 7 days of treatment with compound 1 or compound 3, vimentin expression, a stem cell marker, induced by IDH2 (R140Q) in TF-1 cells is reduced to baseline levels at 2-HG levels below 1 mM (i.e., compound 1 or compound 3 dose >200 nM).

The functional consequence of inhibiting IDH2 and thereby reducing intracellular 2-HG levels also is evaluated in the TF-1 IDH2 (R140Q) mutant cell model.

Compound 1 or Compound 3 Reduces IDH2 (R140Q)-Induced GM-CSF-Independent Growth in TF-1 Cells Upon treatment of TF-1 IDH2 (R140Q) cells with compound 1 or compound 3 (1 µM) for 7 days, 2-HG production is inhibited by >99% and GM-CSF independent growth conferred by the expression of TF-1 IDH2 (R140Q) is reversed.

Compound 1 or Compound 3 Reduces Histone Hypermethylation Associated with Elevated Levels of 2-HG Following treatment with compound 1 or compound 3, histone hypermethylation induced by IDH2 (R140Q) in TF-1 cells is reversed based on Western blot analysis. A concentration-dependent reduction in histone methylation is observed at all 4 histone marks (H3K4me3, H3K9me3, H3K27me3, and H3K36me3). This effect is most apparent at compound 1 or compound 3 concentrations known to reduce intracellular 2-HG levels below 1 mM (i.e., compound 1 or compound 3 dose >200 nM) in the TF-1 IDH2 (R140Q) mutant cell system). The $IC_{50}$ for histone demethylation at H3K4me3 following 7 days of treatment is calculated as 236 nM. This result is consistent with the requirement to dose at >$IC_{90}$ for compound 1 or compound 3 in order to alter histone hypermethylation and is consistent with the 200 nM dose of compound 3 needed to induce changes in histone methylation within the first 7 days.

Compound 1 or Compound 3 Reverses the Differentiation Block Induced by the IDH2 (R140Q) Mutation in TF-1 Erythroleukemia Cell Lines Treatment with compound 1 or compound 3 restores the EPO-induced expression of both hemoglobin gamma 1/2 and Kruppel-like factor 1(KLF-1), a transcription factor that regulates erythropoiesis, in TF-1 IDH2 (R140Q) mutant cells when the 2-HG levels fall below 1 mM.

Treatment of Primary Human AML Blast Cells with Compound 1 or Compound 3 Leads to an Increase in Cellular Differentiation IDH2 (R140Q) mutant patient samples are treated in an ex vivo assay with compound 1 or compound 3. Living cells are sorted and cultured in the presence or absence of compound 1 or compound 3 (500, 1000, and 5000 nM). Cells are counted at Days 3, 6, 9, and 13 and normalized to DMSO control. Upon compound treatment, a proliferative burst is seen starting at Day 6 consistent with the onset of cellular differentiation. Following 9 days of treatment ex vivo, the bone marrow blasts are analyzed for morphology and differentiation status in the presence or absence of compound 1 or compound 3; the cytologic analysis is blinded with regard to treatment. Cytology reveals that the percentage of blast cells decreases from 90% to 55% by Day 6 and is further reduced to 40% by Day 9 of treatment with compound 1 or compound 3. Furthermore, there is a clear increase in the population of more differentiated cells as noted by an increase in metamyelocytes.

In summary, ex vivo treatment of primary human IDH2 (R140Q) mutant AML cells with compound 1 or compound 3 results in a decrease in intracellular 2-HG and differentiation of the AML blasts through the macrophage and granulocytic lineages. These data demonstrate that inhibition of mutant IDH2 is able to relieve a block in differentiation present in this leukemic subset.

Example 4

In Vivo Experiments

In this Example 4, the dose strengths of compound 1 are intended to reflect the free-base equivalent strengths.

In Vivo Treatment with Compound 1 or Compound 3 in a Mouse Xenograft Model Led to a Reduction in Tumor 2-HG Concentrations Pharmacokinetic/pharmacodynamic (PK/PD) studies are conducted in female nude mice inoculated subcutaneously with U87MG IDH2 (R140Q) tumor. Animals receive vehicle or single or multiple oral doses of compound 1 or compound 3 at doses ranging from 10 to 150 mg/kg.

Tumor 2-HG concentration decreases rapidly following a single oral dose of compound 1 or compound 3. Tumor 2-HG concentration increases when the plasma concentration of compound 1 or compound 3 decreased below 1000 ng/mL.

In this model, tumor 2-HG levels decrease to baseline, as found in wild-type tissue, following 3 consecutive compound 1 or compound 3 doses of 25 mg/kg or above (twice daily, 12 hour dosing interval). The estimated area under the compound 1 or compound 3 concentration×time curve from 0 to 12 hours ($AUC_{0-12\ hr}$) that results in sustained 90% tumor 2-HG inhibition ($EAUC_{90[0-12\ hr]}$) and sustained 97% tumor 2-HG inhibition ($EAUC_{97[0-12\ hr]}$) are approximately 5000 and 15200 hr·ng/mL, respectively.

Effect of Treatment with Compound 1 or Compound 3 or Cytarabine on Survival, Tumor Burden, and Tumor Differentiation in Tumor Bearing Mice and Naïve Mice 40 NOD/SCID mice are engrafted on Day 1 with $2*10^6$/mouse of AMM7577-P2 (HuKemia® model, Crown BioScience Inc.) frozen cells that may be thawed out from liquid $N_2$. Peripheral blood samples are collected weekly for FACS analysis of human leukemia cells starting at Week 3 post-cell inoculation. Plasma and urine samples are collected weekly starting at Week 3 until the termination point. When the tumor growth is about 10% of human $CD45^+$ cell in peripheral blood samples, the engrafted mice may be randomly allocated into 5 groups using the treatment schedule denoted in Table 1.

TABLE 1

| Group# | Treatment* | n | Route | Treatment schedule | Survival at study termination |
|---|---|---|---|---|---|
| 1 | Vehicle | 9 | PO/BID 8/16 interval | Day 48-84 | 0/9 |
| 2 | compound 1 or compound 3 5 mg/kg | 9 | PO/BID 8/16 interval | Day 48-84 | 4/9 |
| 3 | compound 1 or compound 3 15 mg/kg | 9 | PO/BID 8/16 interval | Day 48-84 | 6/9 |
| 4 | compound 1 or compound 3 45 mg/kg | 9 | PO/BID 8/16 interval | Day 48-84 | 9/9 |
| 5 | cytarabine, 2 mg/kg | 4 | 5 Days | Day 48-52 | 0/4 |
| 6 | Age-matched naïve | 5 | — | No treatment | 5/5 |

*Compound 1 is provided as the free-base equivalent strength dose

As shown in Table 1, treatment with compound 3 in a mutant positive AML mouse model, resulted in a dose dependent survival advantage in comparison to cytarabine. In the group of mice receiving the highest dose of compound 3 (Group 4, 45 mg/kg) all 9 mice survived until the study was completed. A dose dependent decrease in leukemia and evidence of normal differentiation is seen in all compound 3 treated animals.

Example 5

The clinical study is a Phase 1, multicenter, open-label, dose-escalation, safety, PK/PD, and clinical activity evaluation of orally administered compound 1 in subjects with advanced hematologic malignancies, such as acute myelogenous leukemia (AML), myelodysplastic syndrome (MDS), chronic myelomonocytic leukemia (CMML), myeloid sarcoma, multiple myeloma, or lymphoma (e.g., T-cell lymphoma), that harbor an IDH2 mutation. In this Example 5, the dose strengths of compound 1 are intended to reflect the free-base equivalent strengths (e.g., when the dose strength of compound 1 is listed as 30 mg, this dose reflects 30 mg of free-base compound 3, which is equivalent to 36 mg of compound 1).

Primary study objectives include 1) assessment of the safety and tolerability of treatment with compound 1 administered continuously as a single agent dosed orally twice daily (approximately every 12 hours) on Days 1 to 28 of a 28-day cycle in subjects with advanced hematologic malignancies, and 2) determination of the maximum tolerated dose (MTD) and/or the recommended Phase 2 dose of compound 1 in subjects with advanced hematologic malignancies. Secondary study objectives include 1) description of the dose-limiting toxicities (DLTs) of compound 1 in subjects with advanced hematologic malignancies, 2) characterization of the pharmacokinetics (PK) of compound 1 and its metabolite 6-(6-(trifluoromethyl)pyridin-2-yl)-N2-(2-(trifluoromethyl)pyridin-4-yl)-1,3,5-triazine-2,4-diamine (compound 2) in subjects with advanced hematologic malignancies, 3) characterization of the PK/pharmacodynamic (PD) relationship of compound 1 and 2-hydroxygluturate (2-HG), and 4) characterization of the clinical activity associated with compound 1 in subjects with advanced hematologic malignancies.

Exploratory study objectives include 1) characterization of the PD effects of compound 1 in subjects with advanced hematologic malignancies by the assessment of changes in the patterns of cellular differentiation of isocitrate dehydrogenase-2 (IDH2)-mutated tumor cells and changes in histone and deoxyribonucleic acid (DNA) methylation in IDH2-mutated tumor cells, and 2) evaluation of gene mutation status, global gene expression profiles, and other potential prognostic markers (cytogenetics) in IDH2-mutated tumor cells, as well as subclonal populations of non-IDH2 mutated tumor cells, to explore predictors of anti-tumor activity and/or resistance, and 3) evaluation of changes in the metabolic profiles in IDH2-mutated tumor cells.

The study includes a dose escalation phase to determine MTD followed by expansion cohorts to further evaluate the safety and tolerability of the MTD. The dose escalation phase utilizes a standard "3+3" design. During the dose escalation phase, consented eligible subjects are enrolled into sequential cohorts of increasing doses of compound 1. Each dose cohort will enroll a minimum of 3 subjects. The first 3 subjects enrolled in each dosing cohort during the dose escalation portion of the study will receive a single dose of study drug on Day −3 (i.e., 3 days prior to the start of twice daily dosing) and undergo safety and PK/PD assessments over 72 hours to evaluate drug concentrations and 2-HG levels. The next dose of study drug is on Cycle 1 Day 1 (C1D1) at which time twice daily dosing begins. If there are multiple subjects in the screening process at the time the third subject within a cohort begins treatment, up to 2 additional subjects may be enrolled with approval of the Medical Monitor. For these additional subjects, the Day −3 through Day 1 PK/PD assessments are optional following discussion with the Medical Monitor.

Dose limiting toxicities are evaluated during Cycle 1 of treatment. Toxicity severity is graded according to the National Cancer Institute Common Terminology Criteria for Adverse Events (NCI CTCAE) Version 4.03. A DLT is defined as follows. Non-hematologic includes all clinically significant non-hematologic toxicities CTCAE≥Grade 3. (For example, alopecia is not considered a clinically significant event). Hematologic includes prolonged myelosuppression, defined as persistence of ≥3 Grade neutropenia or thrombocytopenia (by NCI CTCAE, version 4.03, leukemia-specific criteria, i.e., marrow cellularity <5% on Day 28 or later from the start of study drug without evidence of leukemia) at least 42 days after the initiation of Cycle 1 therapy. Leukemia-specific grading should be used for cytopenias (based on percentage decrease from baseline: 50 to 75%=Grade 3, >75%=Grade 4). Due to frequent co-morbidities and concurrent medications in the population under study, attribution of adverse events (AEs) to a particular drug is challenging. Therefore, all AEs that cannot clearly be determined to be unrelated to compound 1 are considered relevant to determining DLTs.

If, after the third subject completes the 28-day DLT evaluation period (i.e., Cycle 1), and no DLTs are observed, the study will proceed with dose escalation to the next cohort following safety review. If 1 of 3 subjects experiences a DLT during the first cycle, 3 additional subjects are enrolled in that cohort. If none of the additional 3 subjects experience a DLT, dose escalation may continue to the next cohort following safety review. If 2 or more subjects in a cohort experience DLTs during the first cycle, dose escalation is halted and the next lower dose level is declared the MTD. If the MTD cohort includes only 3 subjects, an additional 3 subjects are enrolled at that dose level to confirm that <2 of 6 subjects experience a DLT at that dose.

Increases in the dose of compound 1 for each dose cohort is guided by an accelerated titration design, where the dose is doubled (100% increase) from one cohort to the next until compound 1-related NCI CTCAE Grade 2 or greater toxicity is observed in any subject within the cohort. Subsequent increases in dose are 50% or less until the MTD is determined. The absolute percent increase in the dose is determined by the Clinical Study Team predicated on the type and severity of any toxicity seen in the prior dose cohorts. If warranted based on the emerging data, an alternative dosing schedule (e.g., once daily or three times daily) may be explored. The MTD is the highest dose that causes DLTs in <2 of 6 subjects.

If no DLTs are identified during the dose escalation phase, dose escalation may continue for 2 dose levels above the projected maximum biologically effective dose, as determined by an ongoing assessment of PK/PD and any observed clinical activity, to determine the recommended Phase 2 dose.

To optimize the number of subjects treated at a potentially clinically relevant dose, intra-subject dose escalation is permitted. Following determination of the recommended Phase 2 dose, 3 expansion cohorts (in specific hematologic malignancy indications) of approximately 12 subjects each are treated at that dose. The purpose of the expansion cohorts is to evaluate and confirm the safety and tolerability of the recommended Phase 2 dose in specific disease indications. Subjects enrolled in these cohorts will undergo the same procedures as subjects in the dose escalation cohorts with the exception that they will not be required to undergo the Day −3 through Day 1 PK/PD assessments.

The planned study doses of compound 1 are summarized in Table 2. The starting dose for this study is 30 mg (free-base equivalent strength) administered approximately every 12 hours. Based on evaluation of the safety, tolerability, and PK/PD data of the previous dose levels, it may also be decided that escalation will take place at an intermediate dose level not specified in Table 2.

TABLE 2

Dose Escalation Scheme

| Cohort Level | Compound 1 Dose[1]* | Number of Subjects |
|---|---|---|
| −1 | 15 mg[2] | 3 to 6 |
| 1 | 30 mg | 3 to 6 |
| 2 | 60 mg | 3 to 6 |
| 3 | 120 mg | 3 to 6 |
| 4 | 240 mg | 3 to 6 |
| 5, etc. | 480 mg[3] | 3 to 6 |
| Expansion Cohorts[3] | MTD[4] | 36[5] |

*Compound 1 is provided as 15, 30, 60, 120, 240, or 480 mg free-base equivalent strength doses (for example, in Cohort Level 1, 36 mg of compound 1 is equivalent to 30 mg of free-base compound 3)
[1]Administered as a single agent dosed orally twice daily (approximately every 12 hours) on Days 1 to 28 of a 28-day cycle. If warranted based on the emerging data, an alternative dosing schedule (e.g., once daily or three times daily) may be explored.
[2]If DLTs are observed at Dose Level 1 (30 mg), the dose for the second cohort is decreased to 15 mg (Dose Level −1).
[3]Continued doubling of the dose until compound 1-related NCI CTCAE ≥ Grade 2 toxicity is observed. Following evaluation of the event(s), subsequent increases in dose ≤ 50% until MTD is determined. The absolute percent increase in the dose is predicated on the type and severity of any toxicity seen in the prior dose cohorts. Dose escalation will never exceed 100%.
[4]Defined as the highest dose that causes DLTs in <2 of 6 subjects. If no DLTs are identified, dosing will continue for 2 dose levels above the projected maximum biologically effective dose, as determined by an ongoing assessment of PK/PD and any observed clinical activity to determine the recommended Phase 2 dose.
[5]To include 3 cohorts of 12 subjects each in specific hematologic malignancy indication.

If warranted based on the emerging data, an alternative dosing schedule (e.g., once daily or three times daily) may be explored as shown in Table 3.

TABLE 3

Dose Escalation Scheme

| Cohort Level | Compound 1 Dose* | Number of Subjects |
|---|---|---|
| 1 | 30 mg[1] | 3 to 6 |
| 2 | 50 mg[1] | 3 to 6 |
| 3 | 75 mg[1] | 3 to 6 |
| 4 | 100 mg[2] | 3 to 6 |
| 5 | 100 mg[1] | 3 to 6 |
| 6 | 150 mg[2] | 3 to 6 |

[1]Administered as a single agent dosed orally twice daily (approximately every 12 hours) on Days 1 to 28 of a 28-day cycle.
[2]Administered as a single agent dosed orally once daily on Days 1 to 28 of a 28-day cycle. A mean plasma half-life of greater than 40 hours, a favorable PK profile, led to the possibility of once daily dosing.
*Compound 1 is provided as 30, 50, 75, 100 or 150 mg free-base equivalent strength doses (for example, in Cohort Level 1, 36 mg of compound 1 is equivalent to 30 mg of free-base compound 3).

Subjects will undergo screening procedures within 28 days prior to the start of study drug treatment to determine eligibility. Screening procedures include medical, surgical, and medication history, confirmation of IDH2 mutation in leukemic blasts (if not documented previously), physical examination, vital signs, Eastern Cooperative Oncology Group (ECOG) performance status (PS), 12-lead electrocardiogram (ECG), evaluation of left ventricular ejection fraction (LVEF), clinical laboratory assessments (hematology, chemistry, coagulation, urinalysis, and serum pregnancy test), bone marrow biopsy and/or aspirate, and blood and urine samples for 2-HG measurement.

Three days prior to starting the twice daily dosing of compound 1 (Day −3), the first 3 subjects enrolled in each cohort in the dose escalation phase will receive a single dose of compound 1 in clinic and have serial blood and urine samples obtained for determination of blood and urine concentrations of compound 1, its metabolite, and 2-HG. A full 72-hour PK/PD profile is conducted: subjects are required to remain at the study site for 10 hours on Day −3 and return on Days −2, −1, and 1 for 24, 48, and 72 hour samples, respectively. During the in-clinic period on Day −3, clinical observation and serial 12-lead ECGs and vital signs assessments are conducted.

Twice daily treatment with compound 1 will begin on C1D1; for subjects who did not undergo the Day −3 PK/PD assessments, clinical observation and serial 12-lead ECGs and vital signs assessments are conducted over 8 hours following their first dose of compound 1 on C1D1. Safety assessments conducted during the treatment period include physical examination, vital signs, ECOG PS, 12-lead ECGs, evaluation of LVEF, and clinical laboratory assessments (hematology, chemistry, coagulation, and urinalysis).

All subjects will undergo PK/PD assessments over a 10-hour period on both C1D15 and C2D1. In addition, subjects will collect urine samples at home once every other week (starting on C1D8) prior to the morning dose for determination of 2-HG levels.

Subjects will have the extent of their disease assessed, including bone marrow biopsies and/or aspirates and peripheral blood, at screening, on Day 15, Day 29 and Day 57, and every 56 days thereafter while on study drug treatment, independent of dose delays and/or dose interruptions, and/or at any time when progression of disease is suspected. Response to treatment is determined by the Investigators based on modified International Working Group (IWG) response criteria for acute myelogenous leukemia (AML).

Subjects may continue treatment with compound 1 until disease progression, occurrence of a DLT, or development of other unacceptable toxicity. All subjects are to undergo an end of treatment assessment (within approximately 5 days of the last dose of study drug); in addition, a follow-up assessment is to be scheduled 28 days after the last dose.

It is estimated that approximately 57 subjects are enrolled in the study. This assumes that identification of the MTD requires the evaluation of 6 dose levels of compound 1 with only 3 subjects per dose level, with the exception of the MTD which required 6 subjects (n=21) with 12 subjects enrolled per cohort in the expansion phase (n=36). Additional subjects may be needed for cohort expansion during dose escalation, for the replacement of non-evaluable subjects, or for evaluation of alternative dosing regimens other than the planned escalation scheme or the MTD, to optimize the recommended Phase 2 dose.

A patient must meet all of the following inclusion criteria to be enrolled in the clinical study. 1) Subject must be ≥18 years of age; 2) Subjects must have advanced hematologic malignancy including: a) Relapsed and/or primary refractory AML as defined by World Health Organization (WHO) criteria, b) untreated AML, ≥60 years of age and are not candidates for standard therapy due to age, performance status, and/or adverse risk factors, according to the treating physician and with approval of the Medical Monitor, c) Myelodysplastic syndrome with refractory anemia with excess blasts (subtype RAEB-1 or RAEB-2), or considered high-risk by the Revised International Prognostic Scoring System (IPSS-R) (Greenberg et al. *Blood.* 2012; 120(12): 2454-65) that is recurrent or refractory, or the patient is intolerant to established therapy known to provide clinical benefit for their condition (i.e., patients must not be candidates for regimens known to provide clinical benefit), according to the treating physician and with approval of the Medical Monitor, and d) Subjects with other relapsed and/or primary refractory hematologic cancers, for example CMML, who fulfill the inclusion/excluding criteria may be considered on a case-by case basis; 3) subjects must have documented IDH2 gene-mutated disease based on local evaluation. Analysis of leukemic blast cells for IDH2 gene mutation is to be evaluated at screening (if not evaluated previously) by the site's local laboratory to determine subject eligibility for the study. If the site does not have local laboratory access for IDH2 gene mutation analysis, central laboratory evaluation is acceptable. A pretreatment tumor sample (from blood and/or bone marrow) is required for all screened subjects for central laboratory biomarker analysis. Gene mutation analysis of a tumor sample (from blood or bone marrow) is to be repeated at the End of Treatment visit and submitted to the central laboratory for biomarker analysis; 4) Subjects must be amenable to serial bone marrow biopsies, peripheral blood sampling, and urine sampling during the study (the diagnosis and evaluation of AML or MDS can be made by bone marrow aspiration when a corebiopsy is unobtainable and/or is not a part of the standard of care. A bone marrow biopsy is required in case of dry tap or failure (mainly dilution) with the aspiration); 5) Subjects or their legal representatives must be able to understand and sign an informed consent; 6) Subjects must have ECOG PS of 0 to 2; 7) Platelet count ≥20,000/μL, (Transfusions to achieve this level are allowed.) Subjects with a baseline platelet count of <20,000/μL, due to underlying malignancy are eligible with Medical Monitor approval; 8) Subjects must have adequate hepatic function as evidenced by: a) Serum total bilirubin ≤1.5×upper limit of normal (ULN), unless considered due to Gilbert's disease or leukemic organ involvement, and b) Aspartate aminotransferase, Alanine aminotransferase (ALT), and alkaline phosphatase (ALP) ≤3.0×ULN, unless considered due to leukemic organ involvement; 9) Subjects must have adequate renal function as evidenced by a serum creatinine ≤2.0× ULN or creatinine clearance >40 mL/min based on the Cockroft-Gault glomerular filtrationrate (GFR) estimation: (140−Age)×(weight in kg)×(0.85 if femaile)/72×serum creatinine; 10) Subjects must be recovered from any clinically relevant toxic effects of any prior surgery, radiotherapy, or other therapy intended for the treatment of cancer. (Subjects with residual Grade 1 toxicity, for example Grade 1 peripheral neuropathy or residual alopecia, are allowed with approval of the Medical Monitor.); and 11) Female subjects with reproductive potential must have a negative serum pregnancy test within 7 days prior to the start of therapy. Subjects with reproductive potential are defined as one who is biologically capable of becoming pregnant. Women of childbearing potential as well as fertile men and their partners must agree to abstain from sexual intercourse or to use an effective form of contraception during the study and for 90 days (females and males) following the last dose of compound 1.

Compound 1 is provided as 5, 10, 50, and 200 mg free-base equivalent strength tablets to be administered orally, twice daily or once daily. The tablets contain 6, 12, 60, and 240 mg of compound 1, respectively.

Alternatively, compound 1 may be provided as 25, 50, 100 and/or 150 mg free-base equivalent strength tablets. These tablets contain 30, 60, 120 and/or 180 mg of compound 1, respectively.

The first 3 subjects in each cohort in the dose escalation portion of the study will receive a single dose of study drug on Day −3; their next dose of study drug is administered on C1D1 at which time subjects will start dosing twice daily (approximately every 12 hours) on Days 1 to 28 in 28-day cycles. Starting with C1D1, dosing is continuous; there are no inter-cycle rest periods. Subjects who are not required to undergo the Day −3 PK/PD assessments will initiate twice daily dosing (approximately every 12 hours) with compound 1 on C1D1.

Subjects are required to fast (water is allowed) for 2 hours prior to study drug administration and for 1 hour following study drug administration.

The dose of compound 1 administered to a subject is dependent upon which dose cohort is open for enrollment when the subject qualifies for the study. The starting dose of compound 1 to be administered to the first cohort of subjects is 30 mg (free-base equivalent strength) administered orally twice a day.

Subjects may continue treatment with compound 1 until disease progression, occurrence of a DLT, or development of other unacceptable toxicity.

Criteria for Evaluation
Safety

A 12-lead electrocardiogram (ECG) is to be obtained at screening, on Days 8, 15, and 22 of Cycle 1, on Days 1 and 15 of Cycle 2, on Day 1 of each treatment cycle thereafter, at the End of Treatment visit, and at the Follow-up visit. Additionally, serial 12-lead ECGs are to be obtained following the first dose of study treatment (i.e., on Day −3 for subjects undergoing the 72-hour PK/PD profile or on C1D1 for subjects who do not attend the Day −3 assessment) at the following times: predose, and 30±10 minutes and 2, 4, 6, and 8 hours (±15 minutes) post dose following the morning administration of study drug. Serial ECGs should be obtained following vital signs assessments. Subjects should be instructed to take their dose of compound 1 in clinic on these days. The 12-lead ECGs should be obtained following 3 minutes of recumbency.

Subjects are to have left ventricular ejection fraction (LVEF) determined by echocardiogram (ECHO) or multiple gated acquisition scan (MUGA) within 28 days of C1D1; repeat assessments are to be conducted on C3D1, Day 1 of every other treatment cycle thereafter (e.g., C5D1, D7D1, etc), at the End of Treatment visit, and at the Follow-up visit. The same procedure to evaluate LVEF should be conducted throughout the study.

The following therapies are not permitted during the study: (1) other antineoplastic therapy (Hydroxyurea, is allowed prior to enrollment and for up to 28 days after the start of compound 1 dosing for the initial control of peripheral leukemic blasts in subjects with WBC >30,000/μL). If alternative therapy is required for treatment of the subject's disease, the subject should be discontinued from compound 1 treatment; (2) Corticosteroids, with the exception of topical cutaneous, ophthalmic, nasal, and inhalational steroids. (Short course steroid therapy is permitted to treat co-morbidities such as for example, differentiation syndrome.); (3) Medications that are known to prolong QT interval: amiodarone, arsenic trioxide, astemizole, azithromycin, bepridil, chloroquine, chlorpromazine, cisapride, citalopram, clarithromycin, disopyramide, dofetilide, domperidone, droperidol, erythromycin, escitalopram, flecainide, halofantrine, haloperidol, ibutilide, levomethadyl, mesoridazine, methadone, moxifloxacin, pentamidine, pimozide, probucol, procainamide, quinidine, sevoflurane, sotalol, sparfloxacin, terfenadine, thioridazine, or vandetanib; (4) Sensitive CYP substrate medications that have a narrow therapeutic range: paclitaxel (CYP2C8) warfarin, phenytoin (CYP2C9), S-mephenytoin (CYP2C19), thioridazine (CYP2D6), theophylline and tizanidine (CYP1A2). Co-administration of other CYP2C8, 2C9, 2C19, 2D6, and 1A2 substrates should be used only if medically necessary; and (5) P-pg and BCRP transporter-sensitive substrates digoxin and rosuvastatin. Co-administration of other P-gp or BCRP substrates should be used only if medically necessary.

The following consumables are not permitted within 7 days prior to dosing on Day 1 or during the study: (1) over-the-counter (OTC) medication (excluding routine vitamins), (2) fruit juices, (3) charbroiled meats, and (4) vegetables from the mustard green family (e.g., kale, broccoli, watercress, collard greens, kohlrabi, brussels sprouts, mustard).

The following consumables are not permitted within 14 days prior to dosing on Day 1 or during the study: (1) citrus fruits such as Seville oranges, grapefruit or grapefruit juice and/or pomelos, exotic citrus fruits, or grapefruit hybrids, and (2) red wine.

Consumption of St. John's Wort is not permitted within 28 days prior to dosing on Day 1 or during the study. Consumption of caffeine- or xanthene-containing food or beverages are not permitted for 48 hours prior to dosing until day 6 after dosing.

Medications and treatments other than those specified above are permitted during the study. All intercurrent medical conditions and complications of the underlying malignancy is treated according to standards of medical care. Subjects should receive analgesics, antiemetics, anti-infectives, antipyretics, and blood products as necessary. Additional permitted medications include (1) Growth factors (granulocyte colony-stimulating factor [G-CSF], granulocyte-macrophage colony-stimulating factor [GM-CSF]) can be used to support subjects who have developed dose-limiting Grade 4 neutropenia or Grade 3 neutropenia with fever and/or infection. The use of erythropoietin is permitted according to the American Society of Clinical Oncology Guidelines (Rizzo, et al. *Blood.* 2010; 116(20):4045-59); (2) Hydroxyurea is allowed prior to enrollment and for up to 28 days after the start of compound 1 dosing for the initial control of peripheral leukemic blasts in subjects with WBC >30,000/μL; and (3) steroids for the treatment of differentiation syndrome, if warranted, as standard of care.

Compound 1 may cause sensitivity to direct and indirect sunlight. The patients should be warned to avoid direct sun exposure. When exposure to sunlight is anticipated for longer than 15 minutes, the patient should be instructed to apply factor 30 or higher sunscreen to exposed areas and wear protective clothing and sunglasses.

AEs, including determination of DLTs, serious adverse events (SAEs), and AEs leading to discontinuation; safety laboratory parameters; physical examination findings; vital signs; 12-lead ECGs; LVEF; and ECOG PS are monitored during the clinical study. Determination of ECOG PS is performed at screening, on Day −3 (for subjects undergoing 72-hour PK/PD profile), on Days 1 and 15 of Cycle 1, on Day 1 of each treatment cycle thereafter, at the End of Treatment visit, and at the Follow-up visit. The severity of AEs is assessed by the NCI CTCAE, Version 4.03.

Monitoring of adverse events (AEs) is conducted throughout the study. Adverse events and severe adverse events (SAEs) are recorded in the electronic case report form (eCRF) from time of the signing informed consent through 28 days after the last study drug dose. In addition, SAEs that are assessed as possibly or probably related to study treatment that occur >28 days post-treatment also are to be reported. All AEs should be monitored until they are resolved or are clearly determined to be due to a subject's stable or chronic condition or intercurrent illness(es).

An adverse event (AE) is any untoward medical occurrence associated with the use of a drug in humans, whether or not considered drug related. An AE (also referred to as an adverse experience) can be any unfavorable and unintended sign (e.g., an abnormal laboratory finding), symptom, or disease temporally associated with the use of a drug, without any judgment about causality. An AE can arise from any use of the drug (e.g., off-label use, use in combination with another drug) and from any route of administration, formulation, or dose, including an overdose.

A suspected adverse reaction is any AE for which there is a reasonable possibility that the drug caused the AE. For the purposes of expedited safety reporting, 'reasonable possibility' means there is evidence to suggest a causal relationship between the drug and the AE. An unexpected AE is one for which the nature or severity of the event is not consistent with the applicable product information, e.g., the Investigator's Brochure. An AE or suspected adverse reaction is considered serious (SAE) if, in the view of either the Investigator or Sponsor, it results in any of the following outcomes: (a) death; (b) life-threatening (the subject was at immediate risk of death from the reaction as it occurred, i.e., it does not include a reaction which hypothetically might have caused death had it occurred in a more severe form), (c) in-patient ;hospitalization or prolongation of existing hospitalization (hospitalization admissions and/or surgical operations scheduled to occur during the study period, but planned prior to study entry are not considered AEs if the illness or disease existed before the subject was enrolled in the study, provided that it did not deteriorate in an unexpected manner during the study (e.g., surgery performed earlier than planned)); (d) a persistent or significant incapacity or substantial disruption of the ability to conduct normal life functions; (e) congenital anomaly/birth defect; or (f) an important medical event (an event that may not result in death, be life-threatening, or require hospitalization but may be considered an SAE when, based upon appropriate medical judgment, it may jeopardize the patient or subject and may require medical or surgical intervention to prevent one of the outcomes listed in the definitions for SAEs. Examples of such medical events include allergic bronchospasm requiring intensive treatment in an emergency room or at home, blood dyscrasias or convulsions that do not result in in-patient hospitalization, or the development of drug dependency or drug abuse).

Intensity of all AEs, including clinically significant treatment-emergent laboratory abnormalities, are graded according to the NCI CTCAE Version 4.03. Adverse events not listed by the CTCAE are graded as follows: (a) Mild: the event is noticeable to the subject but does not interfere with routine activity; (b) Moderate: the event interferes with routine activity but responds to symptomatic therapy or rest; (c) Severe: the event significantly limits the subject's ability to perform routine activities despite symptomatic therapy; (d) Life-threatening: an event in which the subject was at risk of death at the time of the event; or (e) Fatal: an event that results in the death of the subject.

Relationship to study drug administration is determined by the Investigator according to the following criteria: (a) Not Related: Exposure to the study treatment did not occur, or the occurrence of the AE is not reasonably related in time, or the AE is considered unlikely to be related to the study treatment; (b) Possibly Related: The study treatment and the AE were reasonably related in time, and the AE could be explained equally well by causes other than exposure to the study treatment.; or (c) Probably Related: The study treatment and the AE were reasonably related in time, and the AE was more likely explained by exposure to the study treatment than by other causes, or the study treatment was the most likely cause of the AE. For the purpose of safety analyses, all AEs that are classified as possible or probable are considered treatment-related AEs.

Examples of adverse events that may occur are leukocytosis (e.g., Grade 2 hyperleukocytosis, Grade 3 leukocytosis), disease-related differentiation syndrome, confusion (e.g., Grade 3 confusion), and respiratory failure (sepsis) (e.g., Grade 5 respiratory failure), anorexia (e.g., Grade 3 anorexia), nausea (e.g. Grade 1 nausea), pyrexia, diarrhea (e.g., Grade 3 diarrhea), thrombocytopenia, anemia, dizziness, neutropenia (e.g., febrile neutropenia), peripheral edema, sepsis, cough, fatigue, petechia, and rash.

Pharmacokinetics and Pharmacodynamics

Serial blood samples are evaluated for determination of concentration-time profiles of compound 1 and its metabolite compound 2. Urine samples are evaluated for determination of urinary excretion of compound 1 and its metabolite compound 2. Blood, bone marrow, and urine samples are evaluated for determination of 2-HG levels.

Pharmacokinetic Assessments:

Serial blood samples are drawn before and after dosing with compound 1 in order to determine circulating plasma concentrations of compound 1 (and, if technically feasible, the metabolite compound 2). The blood samples will also be used for the determination of 2-HG concentrations.

For the first 3 subjects enrolled in a cohort during the dose escalation phase, a single dose of compound 1 is administered on Day −3 (i.e., 3 days prior to their scheduled C1D1 dose). Blood samples are drawn prior to the single-dose administration of compound 1 and at the following time points after administration: 30 minutes and 1, 2, 3, 4, 6, 8, 10, 24, 48, and 72 hours. After 72 hours of blood sample collection, subjects begin oral twice daily dosing of compound 1 (i.e., C1D1). The PK/PD profile from Day −3 through Day 1 is optional for additional subjects enrolled in the dose escalation phase (i.e., for any subjects beyond the 3 initial subjects enrolled in a cohort) and is not required for subjects enrolled in the expansion cohorts.

All subjects undergo 10-hour PK/PD sampling on C1D15 and C2D1 (i.e., on Days 15 and 29 of twice daily dosing). For this profile, one blood sample is drawn immediately prior to that day's first dose of compound 1 (i.e., dosing with compound 1 occurs at the clinical site); subsequent blood samples are drawn at the following time points after dosing: 30 minutes, and 1, 2, 3, 4, 6, 8, and 10 hours. Additionally, one blood sample is drawn at the End of Treatment Visit.

The timing of blood samples drawn for compound 1 concentration determination may be changed if the emerging data indicates that an alteration in the sampling scheme is needed to better characterize compound 1's PK profile.

Circulating plasma concentrations of 2-HG for cohorts 1 and 2 of Table 4 and cohorts 1 to 6 of Table 7, are measured as described herein.

The mean inhibition may be calculated, for example, by determining the difference between (a) the mean level of 2-HG during the 10-hour sampling on C1D15 and C2D1 and (b) the level of 2-HG at baseline (Day −3 pretreatment), and then dividing the resulting level of 2-HG by the difference between (a) the level of 2-HG at baseline (Day −3 pretreatment) and (c) the level of 2-HG in a subject without IDH-2 gene mutated disease, thereby adjusting for baseline levels of 2-HG in subjects without IDH-2 gene mutated disease.

When adjusting for baseline levels of 2-HG in subjects without IDH-2 gene mutated disease, 10-hour sampling on C1D15 and C2D1 shows mean inhibition of 2-HG at greater than about 90% to up to 100% of baseline (Day −3 pretreatment) in patients with IDH2 R140Q mutations. For example, in Cohort 1 of Table 4, the mean inhibition of 2-HG is 86% on C1D15 (3 patients) and 95% on C2D1 (1 patient). In Cohort 1 of Table 7, the mean inhibition of 2-HG is 88% on C1D15 (4 patients) and 97% on C2D1 (2 patients). In Cohort 2 of Table 4, the mean inhibition of 2-HG is 98% on C1D15 (2 patients) and 100% on C2D1 (4 patients). In Cohort 2 of Table 7, the mean inhibition of 2-HG is 99% on C1D15 (3 patients) and 100% on C2D1 (4 patients). In Cohort 3 of Table 7, the mean inhibition of 2-HG is 103% on C1D15 (3 patients) and 81% on C2D1 (3 patients). In Cohort 4 of Table 7, the mean inhibition of 2-HG is 102% on C1D15 (3 patients) and 101% on C2D1 (2 patients). When adjusting for baseline levels of 2-HG in subjects without IDH-2 gene mutated disease, 10-hour sampling on C1D15 and C2D1 shows mean inhibition of 2-HG at up to 60% of baseline (Day −3 pretreatment) in two patients with IDH2 R172K mutations (Table 7). For example, about 50% inhibition of 2-HG is shown in patient number 5 of Table 4.

Alternatively, the mean inhibition may be calculated with no adjustment for baseline levels of 2-HG in subjects without IDH-2 gene mutated disease, by determining the difference between (a) the mean level of 2-HG during the 10-hour sampling on C1D15 and C2D1 and (b) the level of 2-HG at baseline (Day −3 pretreatment), and then dividing the resulting level of 2-HG by the level of 2-HG at baseline (Day −3 pretreatment). When the mean inhibition is calculated with no adjustment for subjects without IDH-2 gene mutated disease, 10-hour sampling on C1D15 and C2D1 shows mean inhibition of 2HG at up to 97% of baseline (Day −3 pretreatment) in 18 patients with IDH2 R140Q mutations. 10-hour sampling on C1D15 and C2D 1 shows mean inhibition of 2HG at up to 50% of baseline (Day −3 pretreatment) in 2 patients with IDH2 R172K mutations.

Circulating plasma concentrations of compound 1 for cohorts 1 and 2 of Table 4 and cohorts 1 to 6 of Table 7 are measured as described herein. For cohort 1 of Table 4, 10-hour sampling on Day −3 (post a single dose of compound 1), C1D15 and C2D1 shows increased compound 1 mean plasma exposure from 4.7 $AUC_{0-10\ hr}$(h*µg/mL) on Day −3 (4 patients) to 37.7 $AUC_{0-10\ hr}$(h*µg/mL) on C1D15 (3 patients), and 22.6 $AUC_{0-10\ hr}$(h*µg/mL) on C2D1 (1 patient). For cohort 1 of Table 7, 10-hour sampling on Day −3 (post a single dose of compound 1), C1D15 and C2D1 shows increased compound 1 mean plasma exposure from 4.5 $AUC_{0-10\ hr}$(h*µg/mL) on Day −3 (5 patients) to 41.0 $AUC_{0-10\ hr}$(h*µg/mL) on C1D15 (4 patients), and 47.2 $AUC_{0-10\ hr}$(h*µg/mL) on C2D1 (2 patients). For cohort 2 of Table 4, 10-hour sampling on Day −3 (post a single dose of compound 1), C1D15 and C2D1 shows increased compound 1 mean plasma exposure from 5.4 $AUC_{0-10\ hr}$(h*µg/mL) on Day −3 (4 patients) to 58.1 $AUC_{0-10\ hr}$(h*µg/mL) on C1D15 (3 patients), and 93.8 $AUC_{0-10\ hr}$(h*µg/mL) on C2D1 (4 patients). For cohort 2 of Table 7, 10-hour sampling on Day −3 (post a single dose of compound 1), C1D15 and C2D1 shows increased compound 1 mean plasma exposure from 5.4 $AUC_{0-10\ hr}$(h*µg/mL) on Day −3 (4 patients) to 64.1 $AUC_{0-10\ hr}$(h*µg/mL) on C1D15 (3 patients), and 97.0 $AUC_{0-10\ hr}$(h*µg/mL) on C2D1 (4 patients). For cohort 3 of Table 7, 10-hour sampling on Day −3 (post a single dose of compound 1), C1D15 and C2D1 shows increased compound 1 mean plasma exposure from 9.0 $AUC_{0-10\ hr}$(h*µg/mL) on Day −3 (4 patients) to 120 $AUC_{0-10\ hr}$(h*µg/mL) on C1D15 (3 patients), and 146 $AUC_{0-10\ hr}$(h*µg/mL) on C2D1 (3 patients). For cohort 4 of Table 7, 10-hour sampling on Day −3 (post a single dose of compound 1), C1D15 and C2D1 shows increased compound 1 mena plasma exposure from 8.2 $AUC_{0-10\ hr}$(h*µg/mL) on Day −3 (4 patients) to 72.6 $AUC_{0-10\ hr}$(h*µg/mL) on C1D15 (3 patients), and 87.1 $AUC_{0-10\ hr}$(h*µg/mL) on C2D1 (2 patients).

For the first 3 subjects enrolled in a cohort during the dose escalation phase, urine is collected on Day −3 prior to and over the first 72 hours following a single dose of compound 1 to provide a preliminary estimate of the extent to which compound 1 (and, if technically feasible, metabolite compound 2) is eliminated unchanged in the urine. Samples also are analyzed for 2-HG concentrations and for urinary creatinine concentration.

Five urine collections are obtained during this 72-hour period. An initial urine collection is made prior to compound 1 dosing (at least 20 mL). The 2nd urine collection is obtained over approximately 10 hours following compound 1 administration, and a subsequent 8-hour urine collection is obtained between discharge from the clinic and the return visit on the following day (for the 24-hour blood draw). The 4th and 5th urine collections are obtained at approximately the 48-hour and 72-hour blood draws. Additionally, a urine collection (at least 20 mL) occurs at the End of Treatment Visit.

Urine sampling from Day −3 through Day 1 is optional for additional subjects enrolled in the dose escalation phase (i.e., for any subjects beyond the 3 initial subjects enrolled in a cohort) and is not required for subjects enrolled in the expansion cohorts.

The volume of each collection is measured and recorded and sent to a central laboratory for determination of the urinary compound 1 concentration.

Pharmacokinetic Drug Interactions:

Human enzyme phenotyping indicates the routes of metabolism for compound 1 are via multiple cytochrome P450s and uridine diphosphate (UDP)-glucuronosyltransferase (UGTs). Cytochrome P450s (CYPs) 1A2, 2C8, 2C9 and 3A4 and UGTs 1A1, 1A3, 2B7, 2B15 all appear to contribute to the metabolism of compound 1, though at low levels as all metabolite peaks are at or below the limits of quantitation.

Compound 1 and compound 2, are weak inducers of human CYP3A4. Induction of CYP1A2 or CYP2B6 was not observed for either compound. When used as a marker substrate, neither compound appears to be a victim of strong CYP3A4 inducers such as rifampicin. This is consistent with the low turnover seen in the enzyme phenotyping experiments.

Compound 1 is a moderate direct inhibitor of CYP2C8 ($IC_{50}$=3.9 to 4.4 µM), CYP2C9 ($IC_{50}$=3.7 µM), CYP2C19 ($IC_{50}$=6.3 µM) and CYP 2D6 ($IC_{50}$=21 µM) while compound 2 is a moderate direct inhibitor of CYP1A2 ($IC_{50}$=0.43 µM), 2C8 ($IC_{50}$=5.3 µM) and CYP 2C9 ($IC_{50}$=30 µM). Neither compound shows time-dependent or metabolism-dependent inhibition of CYP enzymes.

Compound 1 is characterized as an inhibitor of UGT1A1. Its inhibition of the UGT1A1 *1/*28 and *28/*28 Gilbert's syndrome genotypes are evaluated. The $IC_{50}$s for UGT1A1 by genotype are 1.9, 3.5 and 10 µM for the *1/*1, *1/*28 and *28/*28 genotypes, respectively.

In a Caco-2 cell assay, compound 1 showed excellent permeability (Papp >17.9×10$^{+6}$ cm/sec). The efflux ratio of B→A/A→B is <3 suggesting the active transport of compound 1 across Caco-2 cells is unlikely and thus does not appear to be a substrate for human P-glycoprotein (P-gp) or breast cancer resistance protein (BCRP) in vitro. However, compound 1 is a strong inhibitor of both P-gp (87% and 99% at 5 and 100 μM, respectively) and BCRP (100% at 5 and 100 μM).

Pharmakodynamic Assessments:

Serial blood samples are drawn before and after dosing with compound 1 in order to determine circulating concentrations of 2-HG. Samples collected for PK assessments also are used to assess 2-HG levels. In addition, subjects have blood drawn for determination of 2-HG levels at the screening assessment.

The timing of blood samples drawn for 2-HG concentration determination may be changed if the emerging data indicate that an alteration in the sampling scheme is needed to better characterize the 2-HG response to compound 1 treatment.

Bone marrow also is assessed for 2-HG levels.

Urine is collected before and after dosing with compound 1 for the determination of concentrations of 2-HG. Samples collected for PK assessments on Day −3 is also used to assess 2-HG levels. In addition, subjects have urine sample collected for determination of 2-HG levels at the screening assessment and the End of Treatment visit.

In addition, after initiating twice daily compound 1 treatment, all subjects collect urine samples at home once every two weeks (starting on C1D8) prior to the morning dose. At least 20 mL of urine is collected for each sample. Subjects are instructed on how to store the urine and to bring all samples collected to the clinic at the next visit.

The volume of each collection is measured and recorded and sent to a central laboratory for determination of urinary 2-HG concentration. An aliquot from each collection is analyzed for urinary creatinine concentration.

Clinical Activity

Serial blood and bone marrow sampling is evaluated during the clinical study to determine response to treatment based on modified IWG response criteria in AML. The clinical activity of compound 1 is evaluated by assessing response to treatment according to the 2006 modified IWG criteria for MDS, MDS/myeloproliferative neoplasms (MPN) or AML (Cheson B D, et al. *J Clin Oncol.* 2003; 21(24):4642-9, Cheson B D, et al. *Blood.* 2006; 108(2):419-25).

Disease response to treatment is assessed through the evaluation of bone marrow aspirates and biopsies, along with complete blood counts and examination of peripheral blood films. Subjects have the extent of their disease assessed and recorded at screening, on Days 15, 29, and 57, every 56 days thereafter while on study drug treatment, independent of dose-delays and/or dose interruptions, and/or at any time when progression of disease is suspected. An assessment also is conducted at the End of Treatment visit for subjects who discontinue the study due to reasons other than disease progression.

Bone marrow aspirates and biopsies are to be obtained at screening, Day 15, Day 29, Day 57, every 56 days thereafter independent of dose delays and/or interruptions, at any time when progression of disease is suspected, and at the End of Treatment visit. Bone marrow aspirates and core sampling should be performed according to standard of care and analyzed at the local site's laboratory in accordance with the International Council for Standardization in Hematology (ICSH) Guidelines (Lee S H, et al. *Int J Lab Hematol.* 2008; 30(5):349-64). Bone marrow core biopsies and aspirate are to be evaluated for morphology, flow cytometry, and for karyotype to assess potential clinical activity. Aliquots of the bone marrow and/or peripheral blood blast cells also are evaluated at central laboratories for 2-HG levels, gene expression profiles, histone and DNA methylation patterns, and metabolomic profiling. Peripheral blood for the evaluation of leukemic blast cells is to be obtained at screening, Day 15, Day 29, Day 57, every 56 days thereafter independent of dose delays and/or interruptions, at any time when progression of disease is suspected, and at the End of Treatment visit. Cell counts and flow cytometry are used to assess the state of differentiation of blast cells collected from bone marrow and peripheral blood. Side scatter also is analyzed to determine the complexity of the blast cells in response to compound 1.

Subject demographic data, including gender, date of birth, age, race, and ethnicity, are obtained during screening. Table 4 illustrates clinical activity for ten AML, patients between the ages of 53 and 74 (median age 62.5) with ECOG Performance status of grade 0 or grade 1.

TABLE 4

Clinical Activity

| Cohort[1] (dose*) | Patient number | Tumor Genetics[2] | Characteristics of Prior Therapy | Response[3] (Cycle) |
|---|---|---|---|---|
| 1 (30 mg) | 1 | R140Q, FLT3-ITD, CEPBA | Induction → CR → Consolidation → Relapse → Reinduction → FLT-3 inhibitor → Persistent Disease | NE |
|  | 2 | R140Q | Primary Induction Failure | NE |
|  | 3 | R140Q | Induction → CR → Consolidation → Relapse → Reinduction → Persistent Disease | NE |
|  | 4 | R140Q, NPM1 | Primary Induction Failure | CR (4) |
|  | 5 | R172K, DNMT3A, CEBPA, ASXL1 | Induction → CR → Consolidation → transplant → Relapse → Decitabine → Persistent Disease → MEC → Persistent Disease | CRp (5) |
| 2 (50 mg) | 6 | R140Q | Induction → CR → Consolidation → Relapse → 5-aza → Clofarabine | PD |
|  | 7 | R140Q, NPM1 | Induction → CR → Consolidation → Relapse → 5-aza | CR (3) |
|  | 8 | R140Q, NPM1 | Induction → CR → Consolidation → Relapse | CR (2) |
|  | 9 | R172K | Primary Induction Failure | PR (2) |
|  | 10 | R140Q, NPM1 | Induction → CR → Consolidation → Relapse | CRp (2) |

*Compound 1 is provided as 30 mg or 50 mg free-base equivalent strength doses (for example, in Cohort Level 1, 36 mg of compound 1 is equivalent to 30 mg of free-base compound 3)
[1]Compound 1 is administered as a single agent dosed orally twice daily (approximately every 12 hours) on Days 1 to 28 of a 28-day cycle.
[2]R140Q mutation in IDH2, R172K mutation in IDH2, FLT3-ITD: Fms-related tyrosine kinase 3 (FLT3) internal tandem duplication (ITD), CEPBA: CCAAT/enhancer binding protein alpha, NPM1: nucleophosmin (neucleolar phosphoprotein B23), DNMT3A: DNA (cytosine-5-)methyltransferase 3 alpha, ASXL1: additional sex combs like 1
[3]Response Criteria evaluated as defined in Table 5. CR: Complete Remission, CRp: Complete Remission, Incomplete Platelet Recovery, PR: Partial Remission, PD: Disease Progression, NE: not evaluable.

AML treatment is typically divided into two chemotherapy phases (1) remission induction, which is aimed at eliminating all visible leukemia, and (2) consolidation (post-remission therapy), which is aimed at treating any remaining leukemia cells and preventing a relapse. Reinduction may be pursued following a patient relapse.

The intensity of induction treatment depends upon the patient's age and health. In younger patients, such as those under 60, induction often involves treatment with 2 chemo drugs, cytarabine (ara-C) and an anthracycline drug such as daunorubicin (daunomycin) or idarubicin. Sometimes a third drug, cladribine (Leustatin, 2-CdA), is given as well. Patients with poor heart function cannot be treated with anthracyclines, and so may be treated with another chemo drug, such as fludarabine (Fludara) or topotecan. In rare cases where the leukemia has spread to the brain or spinal cord, chemo may be given into the cerebrospinal fluid (CSF) as well.

Induction destroys most of the normal bone marrow cells as well as the leukemia cells. Most patients develop dangerously low blood counts, and the patient may be very ill. Most patients need antibiotics and blood product transfusions. Drugs to raise white blood cell counts may also be used. Blood counts tend to stay down for weeks. Usually, the patient stays in the hospital during this time.

One to two weeks after chemotherapy treatment, bone marrow biopsies are taken, and should show a reduced number of bone marrow cells and fewer than 10% blasts, otherwise more chemotherapy may be given. Sometimes a stem cell transplant is recommended at this point.

If the bone marrow biopsy shows a reduced number of bone marrow cells and fewer than 10% blasts, within a few weeks normal bone marrow cells return and start making new blood cells. When the blood cell counts recover, a bone marrow sample is taken to see if the leukemia is in remission. Remission induction usually does not destroy all the leukemia cells, and a small number often persist. Without consolidation treatment, the leukemia is likely to return within several months.

Induction is considered successful if remission is achieved. Further treatment, consolidation, is then given to try to destroy any remaining leukemia cells and help prevent a relapse. For younger patients, the main options for AML consolidation therapy are several cycles of high-dose cytarabine (ara-C) (sometimes known as HiDAC), allogeneic (donor) stem cell transplant, or an autologous (patient's own) stem cell transplant. Prior to a stem cell transplant, patients receive very high doses of chemotherapy to destroy all bone marrow cells, followed by stem cell transplant to restore blood cell production. Stem cell transplants have been found to reduce the risk of leukemia coming back more than standard chemotherapy, but they are also more likely to have serious complications, including an increased risk of death from treatment.

Older patients or those in poor health may not be able to tolerate such intensive consolidation treatment. Often, giving them more intensive therapy raises the risk of serious side effects (including treatment-related death) without providing much more of a benefit. These patients may be treated with 1 or 2 cycles of higher dose cytarabine (usually not quite as high as in younger patients), or intermediate-dose Ara-C (MEC), decitabine, 5-azacytidine, clofarabine, 1 or 2 cycles of standard dose cytarabine, possibly along with idarubicin or daunorubicin, or non-myeloablative stem cell transplant (mini-transplant).

The following criteria outlined in Table 5 and Table 6 are used to assess response to treatment.

TABLE 5

Proposed Modified International Working Group Response Criteria for Altering Natural History of MDS

| Category | Response criteria (Responses must last at least 4 weeks) |
|---|---|
| Complete remission | Bone marrow: ≤5% myeloblasts with normal maturation of all cell lines* |
| | Persistent dysplasia is noted*† |
| | Peripheral blood‡ |
| | Hgb ≥ 11 g/dL |
| | Platelets ≥ 100 × 10$^9$/L |
| | Neutrophils ≥ 1.0 × 10$^9$/L† |
| | Blasts = 0% |
| Partial remission | All CR criteria if abnormal before treatment except: |
| | Bone marrow blasts decreased by ≥50% over pretreatment but still >5% |
| | Cellularity and morphology not relevant |
| Marrow CR† | Bone marrow: ≤5% myeloblasts and decrease by ≥50% over pretreatment† |
| | Peripheral blood: if HI responses, they are noted in addition to marrow CR† |
| Stable disease | Failure to achieve at least PR, but no evidence of progression for > 8 wks |
| Failure | Death during treatment or disease progression characterized by worsening of cytopenias, increase in percentage of bone marrow blasts, or progression to a more advanced MDS FAB subtype than pretreatment |
| Relapse after CR or PR | At least 1 of the following: |
| | Return to pretreatment bone marrow blast percentage |
| | Decrement of ≥ 50% from maximum remission/response levels in granulocytes or platelets |
| | Reduction in Hgb concentration by ≥1.5 g/dL or transfusion dependence |
| Cytogenetic response | Complete: Disappearance of the chromosomal abnormality without appearance of new ones |
| | Partial: At least 50% reduction of the chromosomal abnormality |

TABLE 5-continued

Proposed Modified International Working Group Response Criteria for Altering Natural History of MDS

| Category | Response criteria (Responses must last at least 4 weeks) |
|---|---|
| Disease progression | For patients with:<br>Less than 5% blasts: ≥50% increase in blasts to >5% blasts<br>5%-10% blasts: ≥50% increase to >10% blasts<br>10%-20% blasts: ≥50% increase to >20% blasts<br>20%-30% blasts: ≥50% increase to >30% blasts<br>Any of the following:<br>At least 50% decrement from maximum remission/response in granulocytes or platelets<br>Reduction in Hgb by ≥2 g/dL<br>Transfusion dependence |
| Survival | Endpoints:<br>Overall: death from any cause<br>Event free: failure or death from any cause<br>PFS: disease progression or death from MDS<br>DFS: time to relapse<br>Cause-specific death: death related to MDS |

Source: Cheson, et al. *Blood.* 2006; 108(2): 419-25
Abbreviations:
MDS = myelodysplastic syndromes;
CR = complete remission;
Hgb = hemoglobin;
HI = hematologic improvement;
PR = partial remission;
FAB = French-American-British;
AML = acute myeloid leukemia;
PFS = progression-free survival;
DFS = disease-free survival.
Note:
Deletions to IWG response criteria are not shown.
Note:
To convert hemoglobin from g/L to g/dL, divide g/L by 10.
*Dysplastic changes should consider the normal range of dysplastic changes (modification).
†Modification to IWG response criteria (Cheson, et al. *J Clin Oncol.* 2003; 21(24): 4642-9).
‡In some circumstances, protocol therapy may require the initiation of further treatment (e.g., consolidation, maintenance) before the 4-week period. Such subjects can be included in the response category into which they fit at the time the therapy is started. Transient cytopenias during repeated chemotherapy courses should not be considered as interrupting durability of response, as long as they recover to the improved counts of the previous course.

TABLE 6

Proposed Modified International Working Group Response Criteria for Hematologic Improvement

| Hematologic improvement* | Response criteria (Responses must last at least 8 weeks)† |
|---|---|
| Erythroid response (pretreatment, <11 g/dL) | Hgb increase by ≥1.5 g/dL<br>Relevant reduction of units of RBC transfusions by an absolute number of at least 4 RBC transfusions/8 wk compared with the pretreatment transfusion number in the previous 8 wk. Only RBC transfusions given for a Hgb of ≤9.0 g/dL pretreatment counts in the RBC transfusion response evaluation† |
| Platelet response (pretreatment, <100 × $10^9$/L) | Absolute increase of ≥30 × $10^9$/L for patients starting with >20 × $10^9$/L platelets<br>Increase from <20 × $10^9$/L to >20 × $10^9$/L and by at least 100%† |
| Neutrophil response (pretreatment, <1.0 × $10^9$/L) | At least 100% increase and an absolute increase > 0.5 × $10^9$/L† |

TABLE 6-continued

Proposed Modified International Working Group Response Criteria for Hematologic Improvement

| Hematologic improvement* | Response criteria (Responses must last at least 8 weeks)† |
|---|---|
| Progression or relapse after HI‡: | At least 1 of the following: At least 50% decrement from maximum response levels in granulocytes or platelets<br>Reduction in Hgb by >1.5 g/dL<br>Transfusion dependence |

Source: Cheson, et al. *Blood.* 2006; 108(2): 419-25
Abbreviations:
Hgb indicates hemoglobin;
RBC: red blood cell;
HI: hematologic improvement.
Note:
Deletions to the IWG response criteria are not shown.
Note:
To convert hemoglobin from g/L to g/dL, divide g/L by 10.
*Pretreatment counts averages of at least 2 measurements (not influenced by transfusions) ≥ 1 week apart (modification).
†Modification to IWG response criteria (Cheson, et al. *J Clin Oncol.* 2003; 21(24): 4642-9)
‡In the absence of another explanation, such as acute infection, repeated courses of chemotherapy (modification), gastrointestinal bleeding, hemolysis, and so forth. It is recommended that the 2 kinds of erythroid and platelet responses be reported overall as well as by the individual response pattern.

TABLE 8

Cytogenetic classification according to the IPSS and the new 5-group classification

| Classification/ prognostic group | Abnormalities | | |
|---|---|---|---|
| | Single | Double | Complex |
| IPSS | | | |
| Good | Normal; −Y; del(5q); del(20q) | — | — |
| Intermediate | Other | Any | — |
| Poor | 7* | — | ≥3† |
| 5-group | | | |
| Very good | −Y; del(11q) | — | — |
| Good | Normal; del(5q); del(20q); del(12p) | Including del(5q) | — |
| Intermediate | del(7q); +8; i(17q); +19; any other | Any other | — |
| Poor | −7; Inv(3)/t(3q)/del(3q) | Including −7/del(7q) | 3† |
| Very poor | — | — | >3† |

Greenberg P, et al. International scoring system for evaluating prognosis in myelodysplastic syndromes [erratum appears in Blood. 1998; 91(3): 1100]. Blood 1997; 89(6): 2079-2088.
Schanz J, et al. Coalesced multicentric analysis of 2351 patients with myelodysplastic syndromes indicates an underestimation of poor-risk cytogenetics of myelodysplastic syndromes in the international prognostic scoring system. J Clin Oncol 2011; 29(15): 1963-1970.
— indicates not applicable
*Any chromosome 7 abnormality
†Number of clonal abnormalities Table 7 illustrates clinical activity for 14 patients of a total 35 patients with an advanced hematological malignancy characterized by the presence of a mutant allele of IDH2 between the ages of 48 and 81 (median age 68) with ECOG Performance status of grades 0, 1, or 2 (5 with stable disease, 6 with progressive disease, 10 not evaluable patients are not included in Table 7). Neutrophil counts increase by cycle 1 day 15. White blood cell counts and neutrophil counts are in normal range by cycle 2 day 15 in patients with a response.

TABLE 7

Clinical Activity

| Cohort (dose†) | Patient Disease (Cytogenetics) | Tumor Genetics[3] | Characteristics of Prior Therapy | Response[4] (Cycle)[5] |
|---|---|---|---|---|
| 1 (30 mg)[1] | AML (Normal) | R140Q, FLT3 | Relapse 1 → Re-induction Failure | CR (4) |
| | AML (Normal) | R172K, DNMT3A, ASXL1, FLT3 | Relapse (Post-allo-transplant) → Re-induction Failure | CRp (5) |
| | MDS, prior AML (Normal) | R140Q, FLT3 | No prior therapy for MDS | CR (1) |
| | AML, prior MPD (Monosomy 7) | R140Q | Primary Induction Failure | PR (2) |

TABLE 7-continued

Clinical Activity

| Cohort (dose†) | Patient Disease (Cytogenetics) | Tumor Genetics[3] | Characteristics of Prior Therapy | Response[4] (Cycle)[5] |
|---|---|---|---|---|
| 2 (50 mg)[1] | AML (Trisomy 8, t(17;18)) | R140Q | Relapse 1 → Re-induction Failure | CR* (3) |
| | AML (Trisomy 8) | R140Q | Relapse 1 | CR (2) |
| | AML (Normal) | R172K | Primary Induction Failure | PR (2) |
| | AML (Normal) | R140Q, NPM1 | Relapse 1 | Cri (2) |
| | AML (t(1;13)) | R140Q | Primary Induction Failure → Relapse (Post-allo transplant) | CR** (1) |
| 3 (75 mg)[1] | CMML (Normal) | R140Q | Relapse 1 → Relapse 2 | PR (2) |
| 4 (100 mg)[2] | AML, prior MDS/ CMML (Normal) | R140Q, NPM1, FLT3 | Primary Induction Failure → Re-induction Failure | CR (1) |
| 5 (100 mg)[1] | MDS (Trisomy 11) | R140Q, DNMT3A, ASXL1 | Refractory 1 | CRp (2) |
| | MDS (Normal) | R140Q | Refractory 1 | PR (2) |
| 6 (150 mg)[2] | MDS (Normal) | R140Q | No prior therapy for MDS | PR (1) |

†Compound 1 is provided as 30, 50, 75, 100 or 150 mg free-base equivalent strength doses (for example, in Cohort Level 1, 36 mg of compound 1 is equivalent to 30 mg of free-base compound 3)
*Bone marrow blasts 7% at cycle 5 day 1. Dose escalated to 75 mg (free-base equivalent) as a single agent dosed orally twice daily (approximately every 12 hours)
**Bone marrow blast increase 11% at cycle 3 day 1. Dose escalated to 75 mg (free-base equivalent) as a single agent dosed orally twice daily (approximately every 12 hours)
[1]Compound 1 administered as a single agent dosed orally twice daily (approximately every 12 hours) on Days 1 to 28 of a 28-day cycle.
[2]Compound 1 administered as a single agent dosed orally once daily on Days 1 to 28 of a 28-day cycle.
[3]Tumor genetics based on local assessment. R140Q mutation in IDH2, R172K mutation in IDH2, FLT3-ITD: Fms-related tyrosine kinase 3 (FLT3) internal tandem duplication (ITD), CEPBA: CCAAT/enhancer binding protein alpha, NPM1: nucleophosmin (neucleolar phosphoprotein B23), DNMT3A: DNA (cytosine-5-) methyltransferase 3 alpha, ASXL1: additional sex combs like 1
[4]Response Criteria evaluated as defined in Tables 5 and 6. CR: Complete Remission, CRp: Complete Remission, Incomplete Platelet Recovery, CRi: Complete Remission, incomplete hematologic recovery, PR: Partial Remission, PD: Disease Progression, NE: not evaluable.
[5]Five patients with complete remission have a duration of greater than 2.5 months, with a range of one to four months.

Statistical Analysis

Statistical analyses is primarily descriptive in nature since the goal of the study is to determine the MTD of compound 1. Tabulations are produced for appropriate disposition, demographic, baseline, safety, PK, PD, and clinical activity parameters and are presented by dose level and overall. Categorical variables are summarized by frequency distributions (number and percentages of subjects) and continuous variables are summarized by descriptive statistics (mean, standard deviation, median, minimum, and maximum).

Adverse events are summarized by Medical Dictionary for Regulatory Activities (MedDRA) system organ class and preferred term. Separate tabulations are produced for all treatment-emergent AEs (TEAEs), treatment-related AEs (those considered by the Investigator as at least possibly drug related), SAEs, discontinuations due to AEs, and AEs of at least Grade 3 severity. By-subject listings are provided for deaths, SAEs, DLTs, and AEs leading to discontinuation of treatment.

Descriptive statistics are provided for clinical laboratory, ECG interval, LVEF, and vital signs data, presented as both actual values and changes from baseline relative to each on-study evaluation and to the last evaluation on study. Shift analyses are conducted for laboratory parameters and ECOG PS.

Descriptive statistics (i.e., number of subjects, mean, standard deviation, geometric mean and coefficient of variation, median, minimum, and maximum) are used to summarize PK parameters for each dose group and, where appropriate, for the entire population. Such parameters include (but are not limited to) $C_{max}$, time to maximum concentration ($T_{max}$), AUC, elimination half-life, and the fraction of drug excreted unchanged in the urine. The relationships between dose and both $C_{max}$, and AUC is explored graphically for dose-proportionality.

Response to treatment as assessed by the site Investigators using modified IWG is tabulated. Two-sided 90% confidence intervals on the response rates is calculated for each dose level and overall. Data is summarized by type of malignancy for subjects in the cohort expansion phase.

Example 6

5 mg and 10 mg dose strength tablets (free-base equivalent) may be prepared using a dry blend process described in Table A.

TABLE A

| Component | Weight Composition | 5 mg tablet* Amount per tablet (mg) | 10 mg tablet* Amount per tablet (mg) |
|---|---|---|---|
| Compound 1 | 6% | 6.0 | 12.0 |
| Microcrystalline Cellulose | 80% | 80.0 | 160.0 |

TABLE A-continued

| Component | Weight Composition | 5 mg tablet* Amount per tablet (mg) | 10 mg tablet* Amount per tablet (mg) |
|---|---|---|---|
| Hydroxypropyl Cellulose | 2% | 2.0 | 4.0 |
| Sodium Starch Glycolate | 8% | 8.0 | 16.0 |
| Sodium Lauryl Sulfate | 1% | 1.0 | 2.0 |
| Hypromellose Acetate Succinate (Hydroxypropyl Methyl cellulose Acetate Succinate) | 1% | 1.0 | 2.0 |
| Colloidal Silicon Dioxide | 1% | 1.0 | 2.0 |
| Magnesium Stearate | 1% | 1.0 | 2.0 |
| TOTAL | 100% | 100.0 | 200.0 |

*Free-base equivalent 50 mg and 200 mg dose strength tablets (free-base equivalent) may be prepared using a dry granulation process described in Table B

TABLE B

| | Component | Weight Composition | 50 mg tablet* Amount per tablet (mg) | 200 mg tablet* Amount per tablet (mg) |
|---|---|---|---|---|
| Intragranule | Compound 1 | 40% | 60.0 | 240.0 |
| | Microcrystalline Cellulose | 35% | 52.5 | 210.0 |
| | Hydroxypropyl Cellulose | 2% | 3.0 | 12.0 |
| | Sodium Starch Glycolate | 6% | 9.0 | 36.0 |
| | Sodium Lauryl Sulfate | 1% | 1.5 | 6.0 |
| | Hypromellose Acetate Succinate | 1% | 1.5 | 6.0 |
| | Colloidal Silicon Dioxide | 1.50% | 2.25 | 9.0 |
| | Magnesium Stearate | 0.75% | 1.125 | 4.5 |
| Extragranule | Microcrystalline Cellulose | 9.50% | 14.25 | 57.0 |
| | Sodium Starch Glycolate | 2% | 3.0 | 12.0 |
| | Colloidal Silicon Dioxide | 0.50% | 0.75 | 3.0 |
| | Magnesium Stearate | 0.75% | 1.125 | 4.5 |
| | TOTAL | 100% | 150.0 | 600.0 |

*Free-base equivalent 25 mg, 50 mg, 100 mg and 150 mg dose strength tablets (free-base equivalent) may be prepared using a dry granulation common blend as described in Table C.

TABLE C

| Component | Weight Composition | 100 mg tablet* Amount per tablet (mg) | 150 mg tablet* Amount per tablet (mg) |
|---|---|---|---|
| Compound 1 | 30% | 120.0 | 180.0 |
| Microcrystalline Cellulose | 45% | 180.0 | 270.0 |
| Hydroxypropyl Cellulose | 2% | 8.0 | 12.0 |
| Sodium Starch Glycolate | 6% | 24.0 | 36.0 |
| Sodium Lauryl Sulfate | 1% | 4.0 | 6.0 |
| Hypromellose Acetate Succinate | 1% | 4.0 | 6.0 |
| Colloidal Silicon Dioxide | 1.50% | 6.0 | 9.0 |
| Magnesium Stearate | 0.75% | 3.0 | 4.5 |
| Microcrystalline Cellulose | 9.50% | 38.0 | 57.0 |
| Sodium Starch Glycolate | 2% | 8.0 | 12.0 |
| Colloidal Silicon Dioxide | 0.50% | 2.0 | 3.0 |
| Magnesium Stearate | 0.75% | 3.0 | 4.5 |
| TOTAL | 100% | 400.0 | 600.0 |

*Free-base equivalent

While the foregoing invention has been described in some detail for purposes of clarity and understanding, these particular embodiments are to be considered as illustrative and not restrictive. It will be appreciated by one skilled in the art from a reading of this disclosure that various changes in form and detail can be made without departing from the true scope of the invention, which is to be defined by the appended claims rather than by the specific embodiments.

The patent and scientific literature referred to herein establishes knowledge that is available to those with skill in the art. Unless otherwise defined, all technical and scientific terms used herein have the same meaning as commonly understood by one of ordinary skill in the art to which this invention belongs. The issued patents, applications, and references that are cited herein are hereby incorporated by reference to the same extent as if each was specifically and individually indicated to be incorporated by reference. In the case of inconsistencies, the present disclosure, including definitions, will control.

The invention claimed is:

1. A pharmaceutical composition comprising a crystalline form of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol mesylate and at least one pharmaceutically acceptable carrier or adjuvant, wherein the crystalline form is characterized by an X-ray powder diffraction pattern substantially similar to FIG. 40.

2. The pharmaceutical composition of claim 1 for oral administration.

3. The pharmaceutical composition of claim 2, wherein the composition is a tablet.

4. A pharmaceutical composition comprising a crystalline form of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol mesylate and at least one pharmaceutically acceptable carrier or adjuvant, wherein the crystalline form is characterized by an X-ray powder diffraction pattern substantially similar to FIG. 43.

5. The pharmaceutical composition of claim 4 for oral administration.

6. The pharmaceutical composition of claim 5, wherein the composition is a tablet.

7. A method of treating an advanced hematologic malignancy in a subject, wherein the advanced hematologic malignancy is selected from acute myelogenous leukemia, myelodysplastic syndrome, chronic myelomonocytic leukemia, myeloid sarcoma, multiple myeloma, and lymphoma, each characterized by the presence of a mutant allele of IDH2, comprising administering to the subject the pharmaceutical composition of claim 1.

8. The method of claim 7, wherein the advanced hematologic malignancy is acute myelogenous leukemia.

9. The method of claim 8, wherein the acute myelogenous leukemia is relapsed or primary refractory.

10. A method of treating an advanced hematologic malignancy in a subject, wherein the advanced hematologic malignancy is selected from acute myelogenous leukemia, myelodysplastic syndrome, chronic myelomonocytic leukemia, myeloid sarcoma, multiple myeloma, and lymphoma, each characterized by the presence of a mutant allele of IDH2, comprising administering to the subject the pharmaceutical composition of claim 4.

11. The method of claim 10, wherein the advanced hematologic malignancy is acute myelogenous leukemia.

12. The method of claim 11, wherein the acute myelogenous leukemia is relapsed or primary refractory.

\* \* \* \* \*